US012799186B2

(12) United States Patent
Klein et al.

(10) Patent No.: US 12,799,186 B2
(45) Date of Patent: Nov. 17, 2026

(54) ANTIBODIES AGAINST INFECTIOUS PATHOGENS AND METHOD FOR PRODUCTION THEREOF

(71) Applicants: Universität zu Köln, Cologne (DE); Yeda Research and Development Co., Ltd. Weizmann Institute of Science, Rehovot (IL)

(72) Inventors: Florian Klein, Cologne (DE); Matthias Zehner, Bonn (DE); Stefanie Lichtenthäler, Weyerbusch (DE); Ron Diskin, Rehovot (IL)

(73) Assignees: Universität zu Köln, Cologne (DE); Yeda Research and Development Co., Ltd. Weizmann Institute of Science, Rehovot (IL)

( * ) Notice: Subject to any disclaimer, the term of this patent is extended or adjusted under 35 U.S.C. 154(b) by 1184 days.

(21) Appl. No.: 17/766,705

(22) PCT Filed: Oct. 7, 2020

(86) PCT No.: PCT/EP2020/078109
§ 371 (c)(1),
(2) Date: Apr. 5, 2022

(87) PCT Pub. No.: WO2021/069487
PCT Pub. Date: Apr. 15, 2021

(65) Prior Publication Data
US 2024/0075139 A1 Mar. 7, 2024

(30) Foreign Application Priority Data
Oct. 7, 2019 (EP) .................................... 19201736

(51) Int. Cl.
*C07K 16/10* (2026.01)
*A61K 39/00* (2006.01)
(Continued)

(52) U.S. Cl.
CPC .............. *C07K 16/10* (2013.01); *A61K 39/42* (2013.01); *A61P 37/04* (2018.01); *A61K 2039/505* (2013.01); *A61K 2039/55* (2013.01)

(58) Field of Classification Search
None
See application file for complete search history.

(56) References Cited

PUBLICATIONS

Paul, W.E. Fundamental Immunology. Third Edition. Chapter 9, pp. 292-295. 1993. ISBN 0-7817-0022-1. (Year: 1993).*
(Continued)

*Primary Examiner* — Thomas J. Visone
(74) *Attorney, Agent, or Firm* — Eversheds-Sutherland (US) LLP

(57) ABSTRACT

The present invention relates to a method for obtaining monoclonal human antibodies directed against an infectious pathogen, monoclonal human antibodies or binding fragments thereof which are directed against an infectious pathogen as obtained by the method of the invention, a pharmaceutical composition comprising such monoclonal human antibodies, a kit comprising such antibodies, and the monoclonal antibodies or binding fragments thereof and the pharmaceutical composition and the kit for use as a medicament and in the treatment or prevention of a disease caused by the infectious pathogen.

12 Claims, 5 Drawing Sheets

Specification includes a Sequence Listing.

(51) Int. Cl.
*A61K 39/42* (2006.01)
*A61P 37/04* (2006.01)

(56) References Cited

PUBLICATIONS

PCT International Search Report and Written Opinion for PCT/EP2020/078109, mailed Jan. 13, 2021 (22 pages).
European Search Report for EP19201736, date search completed Mar. 30, 2020 (18 pages).
James W Larrick et al: "Characterization of human hybridomas secreting antibody to tetanus toxoid", Proc. Natl. Acad. Sci. USA, vol. 80, Oct. 1, 1983 (Oct. 1, 1983), pp. 6376-6380.
Carlo M Croce et al: "Production of human hybridomas secreting antibodies to measles virus", Nature, Macmillan Journals Ltd., Etc.!, London, vol. 288, No. 5790, Dec. 1, 1980 (Dec. 1, 1980), pp. 488-489.
Huttner Angela et al: "Determinants of antibody persistence across doses and continents after single-dose rVSV-ZEBOV vaccination for Ebola virus disease: an observational cohort study", Lancet Infectious Diseases, Elsevier Ltd, US, vol. 18, No. 7, Apr. 5, 2018 (Apr. 5, 2018), pp. 738-748.
K Sikora et al: "Human hybridomas from patients with malignant disease", British Journal of Cancer, vol. 47, No. 1, Jan. 1, 1983 (Jan. 1, 1983), pp. 135-145.
Kozbor D et al: "The production of monoclonal antibodies from human lymphocytes", Immunology Today, Elsevier Publications, Cambridge, GB, vol. 4, No. 3, Mar. 1, 1983 (Mar. 1, 1983), pp. 72-79.
Andrew I. Flyak et al: "Mechanism of Human Antibody-Mediated Neutralization of Marburg Virus", Cell, vol. 160, No. 5, Feb. 1, 2015 (Feb. 1, 2015), pp. 893-903.
Pramila Rijal et al: "Therapeutic Monoclonal Antibodies for Ebola Virus Infection Derived from Vaccinated Humans", Cell Reports vol. 27, No. 1, Apr. 1, 2019 (Apr. 1, 2019), pp. 172-186.e7.
Chad E. Mire et al: "Therapeutic treatment of Marburg and Ravn virus infection in nonhuman primates with a human monoclonal antibody", Science Translational Medicine, vol. 9, No. 384, Apr. 5, 2017 (Apr. 5, 2017), p. eaai8711.
Liam B. King et al: "The Marburgvirus-Neutralizing Human Monoclonal Antibody MR191 Targets a Conserved Site to Block Virus Receptor Binding", Cell Host & Microbe, vol. 23, No. 1, Jan. 1, 2018 (Jan. 1, 2018), pp. 101-109.e4.
Xuelian Zhao et al: "Immunization-Elicited Broadly Protective Antibody Reveals Ebolavirus Fusion Loop as a Site of Vulnerability", Cell, vol. 169, No. 5, May 1, 2017 (May 1, 2017), pp. 891-904.e15.
Kelly L Warfield et al: "Role of Antibodies in Protection Against Ebola Virus in Nonhuman Primates Immunized With Three Vaccine Platforms", Journal of Infectious Diseases. JID, vol. 218, No. suppl_5, Jun. 25, 2018 (Jun. 25, 2018), pp. S553-S564.
Jennifer M. Brannan et al: "Post-exposure immunotherapy for two ebolaviruses and Marburg virus in nonhuman primates", Nature Communications, vol. 10, No. 1, Jan. 10, 2019 (Jan. 10, 2019), p. 894-898.
Katie A. Howell et al: "Antibody Treatment of Ebola and Sudan Virus Infection via a Uniquely Exposed Epitope within the Glycoprotein Receptor-Binding Site", Cell Reports vol. 15, No. 7, May 1, 2016 (May 1, 2016), pp. 1514-1526.
Anna Z. Wec et al: "Antibodies from a Human Survivor Define Sites of Vulnerability for Broad Protection against Ebolaviruses", Cell, vol. 169, No. 5, May 1, 2017 (May 1, 2017), pp. 878-890.e15.
Sivapalsingam, S. et al The Lancet Infectious Diseases 18, 884-893, doi:10.1016/s1473-3099(18=30397-9 (2018).
Gaudinski, M.r. et al. The Lancet, doi:10.1016/(s0140-6736(19)30036-4 (2019).
Davey, R.T., Jr. et al. N Engl J Med 375, 1448-1456, doi:10.1056/NEJMoa1604330 (2016).
Tiller, T. et al. Journal of Immunological Methods, 329, 112-124 (2008).
Von Boehmer, L. et al. Nat Protoc 11, 1908-1923 (2016).
Lefranc et al., NAR 27:209-212 (1999).
Karlin and Altschul (Proc. Natl. Acad. Sci. USA (1993) 90: 5873-5877).
Altschul et al. (J. Mol. Biol. (1990) 215: 403-410).
Cutts et al. Scientific Reports (2019) 9:6590, https://doi.org/10.1038/s41598-019-42386-5.
Bornholdt, Z. A., et al. (2016). "Isolation of potent neutralizing antibodies from a survivor of the 2014 Ebola virus outbreak." Science 351(6277): 1078-1083.
Corti, D., et al. (2016). "Protective monotherapy against lethal Ebola virus infection by a potently neutralizing antibody." Science 351(6279): 1339-1342.
Gaebler, C., et al. (2013). "Isolation of HIV-1-reactive antibodies using cell surface-expressed gp160Deltac(BaL.)." J Immunol Methods 397(1-2): 47-54.
Maruyama, T., et al. (1999). "Ebola Virus can be effectively neutralized by antibody produced in natural human infection." J Virol.
Mittler, E., et al. (2018). "A Fluorescently Labeled Marburg Virus Glycoprotein as a New Tool to Study Viral Transport and Assembly." J Infect Dis 218(suppl_5): S318-S326.
Ye, J., et al. (2013). "IgBLAST: an immunoglobulin variable domain sequence analysis tool." Nucleic Acids Res 41 (Web Server issue): W34-40.

* cited by examiner a b

SEQUENCE LISTING

```
<160> NUMBER OF SEQ ID NOS: 158

<210> SEQ ID NO 1
<211> LENGTH: 117
<212> TYPE: PRT
<213> ORGANISM: Homo sapiens
<220> FEATURE:
<223> OTHER INFORMATION: Heavy chain of antibody 1T0129

<400> SEQUENCE: 1

Gln Val Gln Leu Val Gln Ser Gly Ala Glu Ala Lys Lys Pro Gly Ala
1               5                   10                  15

Ser Val Arg Val Ser Cys Gln Thr Ser Gly Tyr Thr Phe Thr Gly His
            20                  25                  30

Tyr Leu His Trp Val Arg Gln Ala Pro Gly Gln Gly Leu Glu Trp Leu
        35                  40                  45

Gly Trp Ile Asn Pro Ser Thr Gly Gly Thr Phe Tyr Ala Pro Lys Phe
    50                  55                  60
```

```
Lys Asp Arg Val Asp Met Thr Arg Asp Thr Ser Thr Thr Thr Ala Tyr
65                  70                  75                  80

Met Asn Leu Ser Ser Leu Thr Ser Asp Asp Thr Ala Val Tyr Tyr Cys
                85                  90                  95

Gly Thr Gly Ile Pro Ser Asp Ile Asp Tyr Trp Gly Gln Gly Thr Leu
            100                 105                 110

Val Thr Val Ser Ser
        115
```

<210> SEQ ID NO 2
<211> LENGTH: 108
<212> TYPE: PRT
<213> ORGANISM: Homo sapiens
<220> FEATURE:
<223> OTHER INFORMATION: Light chain of antibody 1T0129

<400> SEQUENCE: 2

```
Asp Ile Val Met Thr Gln Phe Pro Asp Phe Val Ala Val Ser Pro Gly
1               5                   10                  15

Glu Arg Ala Thr Ile Ser Cys Glu Ser Ser Gln Ser Val Leu Tyr Gln
            20                  25                  30

Ser Val Ala Trp Tyr Gln His Lys Pro Gly Gln Pro Pro Lys Leu Ile
        35                  40                  45

Ile Ser Trp Ala Ser Arg Arg Gly Ser Gly Val Pro Asn Arg Phe Ser
    50                  55                  60

Gly Ser Gly Ser Gly Thr Asn Phe Ser Leu Thr Ile Ser Ser Leu Arg
65                  70                  75                  80

Pro Glu Asp Val Ala Val Tyr Tyr Cys Gln Gln Tyr Tyr Asn Thr Pro
                85                  90                  95

Arg Thr Phe Gly Gln Gly Thr Lys Leu Glu Ile Lys
            100                 105
```

<210> SEQ ID NO 3
<211> LENGTH: 123
<212> TYPE: PRT
<213> ORGANISM: Homo sapiens
<220> FEATURE:
<223> OTHER INFORMATION: Heavy chain of antibody 1T0139

<400> SEQUENCE: 3

```
Gln Val Gln Leu Gln Glu Ser Gly Pro Gly Leu Val Lys Pro Ser Glu
1               5                   10                  15

Thr Leu Ser Leu Thr Cys Ile Val Ser Gly Gly Ser Leu Ser Ser Tyr
            20                  25                  30

Tyr Trp Ser Trp Val Arg Gln Pro Ala Gly Lys Gly Leu Gln Trp Ile
        35                  40                  45

Gly His Ile Tyr Thr Thr Gly Ser Thr Asn Tyr Asn Pro Ser Leu Lys
    50                  55                  60

Ser Arg Val Thr Met Ser Ile Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Ser Tyr Arg Tyr Asn Ala Tyr Asp Ile His Pro Phe Asp Tyr
            100                 105                 110

Trp Gly Gln Gly Thr Leu Val Thr Val Ser Ser
        115                 120
```

```
<210> SEQ ID NO 4
<211> LENGTH: 106
<212> TYPE: PRT
<213> ORGANISM: Homo sapiens
<220> FEATURE:
<223> OTHER INFORMATION: Light chain of antibody 1T0139

<400> SEQUENCE: 4

Ser Tyr Glu Leu Thr Gln Ser Ser Ser Val Ser Val Ser Pro Gly Gln
1               5                   10                  15

Thr Ala Ser Ile Thr Cys Ser Gly Asp Lys Leu Gly Asp Asn Tyr Val
            20                  25                  30

Cys Trp Tyr Gln Gln Lys Pro Gly Gln Ser Pro Thr Leu Val Ile Tyr
        35                  40                  45

Gln Asp Asn Arg Arg Pro Ser Gly Ile Pro Glu Arg Phe Ser Gly Ser
    50                  55                  60

Asn Ser Gly Asn Thr Ala Thr Leu Thr Ile Arg Gly Thr Gln Ala Leu
65                  70                  75                  80

Asp Glu Ala Asp Tyr Tyr Cys Gln Ala Trp Ala Ser Asn Thr Val Val
                85                  90                  95

Phe Gly Gly Gly Thr Lys Leu Thr Val Leu
            100                 105


<210> SEQ ID NO 5
<211> LENGTH: 124
<212> TYPE: PRT
<213> ORGANISM: Homo sapiens
<220> FEATURE:
<223> OTHER INFORMATION: Heavy chain of antibody 1T0201

<400> SEQUENCE: 5

Glu Val Gln Leu Val Glu Ser Gly Gly Gly Leu Val Lys Pro Gly Gly
1               5                   10                  15

Ser Leu Arg Leu Ser Cys Ala Ala Ala Gly Phe Ser Phe Ser Lys Ala
            20                  25                  30

Trp Met Asn Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Thr Ala
    50                  55                  60

Pro Val Lys Gly Arg Phe Ile Ile Ser Arg Asp Asp Ser Lys Asn Met
65                  70                  75                  80

Leu Tyr Leu Gln Met Asn Ser Leu Lys Ala Glu Asp Thr Ala Val Tyr
                85                  90                  95

Trp Cys Thr Thr Arg Val Asp Met Glu Trp Gly Lys Tyr Gly Thr Asp
            100                 105                 110

Val Trp Gly Gln Gly Thr Thr Val Thr Val Ser Ser
        115                 120


<210> SEQ ID NO 6
<211> LENGTH: 112
<212> TYPE: PRT
<213> ORGANISM: Homo sapiens
<220> FEATURE:
<223> OTHER INFORMATION: Light chain of antibody 1T0201

<400> SEQUENCE: 6

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30
```

```
Tyr Asp Val His Trp Tyr Gln Lys Leu Pro Gly Thr Ala Pro Lys Leu
        35                  40                  45

Leu Ile Tyr Asp Lys Asn Ile Arg Pro Ser Gly Val Pro Asp Arg Phe
    50                  55                  60

Ser Gly Ser Lys Ser Gly Val Ser Ala Ser Leu Ala Ile Thr Gly Leu
65                  70                  75                  80

Gln Ala Glu Asp Glu Ala Asp Tyr Tyr Cys Gln Ser Tyr Asp Ser Arg
                85                  90                  95

Leu Ser Asp Ser Trp Val Phe Gly Gly Gly Thr Lys Leu Thr Val Leu
            100                 105                 110


<210> SEQ ID NO 7
<211> LENGTH: 121
<212> TYPE: PRT
<213> ORGANISM: Homo sapiens
<220> FEATURE:
<223> OTHER INFORMATION: Heavy chain of antibody 1T0221

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr His Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Asn Arg Asn Thr Lys Phe Ala Gln Asn Phe
    50                  55                  60

Gln Gly Arg Val Thr Leu Thr Thr Asp Thr Ser Thr Ser Thr Ala Tyr
65                  70                  75                  80

Leu Glu Leu Arg Ser Leu Arg Ser Asp Asp Thr Ala Val Tyr Tyr Cys
                85                  90                  95

Ala Arg His Val Thr Met Ile Leu Asp Gly Trp Phe Asp Pro Trp Gly
            100                 105                 110

Gln Gly Thr Leu Val Thr Val Ser Ser
        115                 120


<210> SEQ ID NO 8
<211> LENGTH: 108
<212> TYPE: PRT
<213> ORGANISM: Homo sapiens
<220> FEATURE:
<223> OTHER INFORMATION: Light chain of antibody 1T0221

<400> SEQUENCE: 8

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Asn Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Ser Cys Gln Gln Tyr Gly Ser Ser Pro
                85                  90                  95

Leu Thr Phe Gly Gly Gly Thr Lys Val Glu Ile Lys
```

```
            100                 105


<210> SEQ ID NO 9
<211> LENGTH: 118
<212> TYPE: PRT
<213> ORGANISM: Homo sapiens
<220> FEATURE:
<223> OTHER INFORMATION: Heavy chain of antibody 1T0225

<400> SEQUENCE: 9

Gln Val Gln Leu Gln Glu Ser Gly Ser Gly Leu Val Lys Pro Ser Gln
1               5                   10                  15

Thr Leu Ser Leu Thr Cys Ala Val Ser Gly Gly Ala Ile Thr Ser Gly
            20                  25                  30

Gly Phe Ser Trp Ser Trp Ile Arg Gln Pro Pro Gly Lys Gly Leu Glu
        35                  40                  45

Trp Ile Gly Tyr Ile Tyr Pro Ser Gly Ser Ala Tyr Tyr Asn Pro Ser
    50                  55                  60

Leu Lys Ser Arg Val Thr Met Ser Val Asp Thr Ser Lys Lys Gln Phe
65                  70                  75                  80

Ser Leu Lys Leu Asn Ser Val Thr Ala Ala Asp Thr Ala Val Tyr Tyr
                85                  90                  95

Cys Ala Arg Asp Pro Gly Gly Pro Phe Asp His Trp Gly Gln Gly Thr
            100                 105                 110

Leu Val Thr Val Ser Ser
        115


<210> SEQ ID NO 10
<211> LENGTH: 109
<212> TYPE: PRT
<213> ORGANISM: Homo sapiens
<220> FEATURE:
<223> OTHER INFORMATION: Light chain of antibody 1T0225

<400> SEQUENCE: 10

Gln Ser Ala Leu Thr Gln Pro Ala Ser Val Ser Gly Ser Pro Gly Gln
1               5                   10                  15

Ser Ile Thr Ile Ser Cys Thr Ala Thr Ser Ser Asp Leu Asp Asp Tyr
            20                  25                  30

Asn Tyr Val Ser Trp Tyr Gln Gln His Pro Gly Lys Gly Pro Arg Leu
        35                  40                  45

Ile Phe Tyr Asp Val Asn Asn Arg Pro Ser Gly Val Ser Asn Arg Phe
    50                  55                  60

Ser Gly Ser Lys Ser Gly Asp Thr Ala Ser Leu Thr Ile Ser Gly Leu
65                  70                  75                  80

Gln Pro Glu Asp Glu Ala Asp Tyr Tyr Cys Ser Ser Tyr Thr Ser Asn
                85                  90                  95

Phe Ser Val Val Phe Gly Gly Gly Thr Lys Leu Thr Val
            100                 105


<210> SEQ ID NO 11
<211> LENGTH: 124
<212> TYPE: PRT
<213> ORGANISM: Homo sapiens
<220> FEATURE:
<223> OTHER INFORMATION: Heavy chain of antibody 1T0227

<400> SEQUENCE: 11

Glu Val Gln Leu Val Glu Ser Gly Gly Gly Leu Val Lys Pro Gly Gly
1               5                   10                  15
```

Ser Leu Arg Leu Ser Cys Ala Ala Ser Gly Phe Thr Phe Arg Asn Ala
20 25 30

Trp Met Asn Trp Val Arg Gln Ala Pro Gly Lys Gly Leu Glu Trp Val
35 40 45

Gly Arg Ile Lys Ser Arg Ala Asp Gly Gly Pro Thr Asp Tyr Ala Ala
50 55 60

Pro Val Lys Gly Arg Phe Thr Ile Ser Arg Asp Asp Ser Lys Asn Thr
65 70 75 80

Leu Tyr Leu Gln Met Asn Ser Leu Lys Ser Glu Asp Thr Ala Val Tyr
85 90 95

Tyr Cys Thr Thr His Val Pro Asp Tyr Asn Ser Ala Tyr Tyr Trp Val
100 105 110

Tyr Trp Gly Gln Gly Thr Leu Val Thr Val Ser Ser
115 120

<210> SEQ ID NO 12
<211> LENGTH: 112
<212> TYPE: PRT
<213> ORGANISM: Homo sapiens
<220> FEATURE:
<223> OTHER INFORMATION: Light chain of antibody 1T0227

<400> SEQUENCE: 12

Gln Ser Val Leu Thr Gln Pro Pro Ser Val Ser Gly Ala Pro Gly Gln
1 5 10 15

Arg Val Thr Ile Ser Cys Thr Gly Ser Ser Ser Asn Ile Gly Ala Gly
20 25 30

Tyr Asp Val Tyr Trp Tyr Gln Gln Leu Pro Gly Thr Ala Pro Lys Leu
35 40 45

Ile Ile Tyr Gly Asn Asn Asn Arg Pro Ser Gly Val Pro Asp Arg Phe
50 55 60

Ser Ala Ser Lys Ser Gly Pro Ser Ala Ser Leu Ala Ile Thr Gly Leu
65 70 75 80

Gln Ala Glu Asp Glu Ala Asp Tyr Tyr Cys Gln Ser Tyr Asp Ile Arg
85 90 95

Leu Ser Asp Asn Tyr Val Phe Gly Thr Gly Thr Lys Val Thr Val Leu
100 105 110

<210> SEQ ID NO 13
<211> LENGTH: 123
<212> TYPE: PRT
<213> ORGANISM: Homo sapiens
<220> FEATURE:
<223> OTHER INFORMATION: Heavy chain of antibody 1T0248

<400> SEQUENCE: 13

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Met Phe Asn Asn Asp
20 25 30

Ala Met Ser Trp Val Arg Gln Ala Pro Gly Lys Gly Leu Glu Trp Val
35 40 45

Ser Gly Ile Ser Gly Gly Gly Thr Ile Thr His Tyr Ala Asp Ser Val
50 55 60

Lys Gly Arg Phe Thr Ile Ser Arg Asp Asn Ser Asn Asn Thr Leu Tyr
65 70 75 80

Leu Gln Met Asn Ser Leu Arg Ala Glu Asp Thr Ala Ile Tyr Tyr Cys

```
                85                  90                  95

Ala Lys Asp Lys Gly Pro Arg Ala Thr Leu Gly Ala Ile Leu Asp Ser
            100                 105                 110

Trp Gly Gln Gly Thr Leu Val Thr Val Ser Ser
        115                 120


<210> SEQ ID NO 14
<211> LENGTH: 113
<212> TYPE: PRT
<213> ORGANISM: Homo sapiens
<220> FEATURE:
<223> OTHER INFORMATION: Light chain of antibody 1T0248

<400> SEQUENCE: 14

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Asn
            20                  25                  30

Ser Asp Asn Lys Asn Tyr Leu Ala Trp Tyr Gln Gln Arg Pro Gly Leu
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Gly Thr Pro Leu Thr Phe Gly Pro Gly Thr Lys Val Asp Ile
            100                 105                 110

Lys


<210> SEQ ID NO 15
<211> LENGTH: 123
<212> TYPE: PRT
<213> ORGANISM: Homo sapiens
<220> FEATURE:
<223> OTHER INFORMATION: Heavy chain of antibody 1T0321

<400> SEQUENCE: 15

Gln Val Gln Leu Val Gln Ser Gly Ala Asp Val Lys Lys Pro Gly Ala
1               5                   10                  15

Ser Val Lys Val Ser Cys Arg Ala Ser Gly Tyr Lys Phe Thr Asp Phe
            20                  25                  30

Tyr Ile His Trp Val Arg Gln Ala Pro Gly Gln Gly Leu Glu Trp Met
        35                  40                  45

Gly Trp Ile Asn Pro Asn Ser Gly Ala Thr Asn Phe Pro Gln Lys Phe
    50                  55                  60

Gln Gly Arg Val Ala Met Thr Arg Asp Thr Ser Ile Ser Thr Ala Tyr
65                  70                  75                  80

Leu Glu Leu Ser Arg Leu Arg Ser Asp Asp Thr Ala Val Tyr Tyr Cys
                85                  90                  95

Ala Thr Pro Thr Met Thr Thr Arg Ser Tyr Tyr Tyr His Met Asp Val
            100                 105                 110

Trp Gly Gln Gly Thr Thr Val Thr Val Ser Ser
        115                 120


<210> SEQ ID NO 16
<211> LENGTH: 112
<212> TYPE: PRT
```

<213> ORGANISM: Homo sapiens
<220> FEATURE:
<223> OTHER INFORMATION: Light chain of antibody 1T0321

<400> SEQUENCE: 16

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Gly Tyr Asn Tyr Leu Asp Trp Tyr Leu Gln Lys Pro Gly Gln Ser
35 40 45

Pro Gln Leu Leu Ile Tyr Leu Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met His Ala
85 90 95

Leu Gln Thr Pro Trp Thr Phe Gly Gln Gly Thr Lys Val Glu Ile Lys
100 105 110

<210> SEQ ID NO 17
<211> LENGTH: 123
<212> TYPE: PRT
<213> ORGANISM: Homo sapiens
<220> FEATURE:
<223> OTHER INFORMATION: Heavy chain of antibody 1T0325

<400> SEQUENCE: 17

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Pro Phe Arg Asn Tyr
20 25 30

Ala Met Asn Trp Val Arg Gln Ala Pro Gly Lys Gly Leu Glu Trp Val
35 40 45

Ala Ser Ile Ser Gly Ser Gly Asn Arg Thr His Tyr Ala Asp Ala Leu
50 55 60

Lys Gly Arg Phe Thr Ile Ser Arg Asp Asn Phe Lys Asn Thr Leu Phe
65 70 75 80

Leu Gln Met Asn Ser Leu Arg Ala Asp Asp Thr Ala Val Tyr Tyr Cys
85 90 95

Ala Lys Glu Arg Glu Val Ala Phe Val Pro Gly Ala Val Phe Asn Tyr
100 105 110

Trp Gly Gln Gly Thr Leu Val Thr Val Ser Ser
115 120

<210> SEQ ID NO 18
<211> LENGTH: 113
<212> TYPE: PRT
<213> ORGANISM: Homo sapiens
<220> FEATURE:
<223> OTHER INFORMATION: Light chain of antibody 1T0325

<400> SEQUENCE: 18

Asp Ile Val Met Thr Gln Ser Pro Asp Ser Leu Ala Val Ser Leu Gly
1 5 10 15

Glu Arg Ala Thr Ile Asn Cys Lys Ser Ser Gln Arg Ile Leu Tyr Ser
20 25 30

Ser Asn Asn Lys Asn Tyr Leu Thr Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Gln
85 90 95

Tyr Tyr Ser Leu Pro Leu Thr Phe Gly Gly Gly Thr Lys Val Glu Ile
100 105 110

Lys

<210> SEQ ID NO 19
<211> LENGTH: 117
<212> TYPE: PRT
<213> ORGANISM: Homo sapiens
<220> FEATURE:
<223> OTHER INFORMATION: Heavy chain of antibody 1T0371

<400> SEQUENCE: 19

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Arg Phe
20 25 30

Ser Ile Ser Trp Val Arg Gln Ala Pro Gly Gln Gly Leu Glu Trp Met
35 40 45

Gly Arg Ile Ile Pro Thr Leu Gly Ile Ala Asn Tyr Ala Gln Lys Phe
50 55 60

Gln Gly Arg Ala Thr Leu Thr Ala Asp Lys Ser Thr Ser Thr Ala Phe
65 70 75 80

Met Glu Leu Thr Ser Leu Arg Ser Glu Asp Thr Ala Val Tyr Tyr Cys
85 90 95

Ala Thr Leu Glu Met Ala Thr Leu Phe Ala Trp Gly Gln Gly Thr Leu
100 105 110

Val Thr Val Ser Ser
115

<210> SEQ ID NO 20
<211> LENGTH: 107
<212> TYPE: PRT
<213> ORGANISM: Homo sapiens
<220> FEATURE:
<223> OTHER INFORMATION: Light chain of antibody 1T0371

<400> SEQUENCE: 20

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Thr Asn Tyr
20 25 30

Leu Ala Trp Phe Gln Gln Lys Pro Gly Lys Ala Pro Lys Ser Leu Ile
35 40 45

Tyr Ala Ala Ser Ser Leu Gln Ser Gly Val Pro Ser Lys Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Ser Tyr Pro Phe
85 90 95

Thr Phe Gly Gly Gly Thr Lys Val Glu Ile Lys
100 105

<210> SEQ ID NO 21
<211> LENGTH: 121
<212> TYPE: PRT
<213> ORGANISM: Homo sapiens
<220> FEATURE:
<223> OTHER INFORMATION: Heavy chain of antibody 1T0451

<400> SEQUENCE: 21

```
Gln Val Gln Leu Val Gln Ser Gly Ala Glu Val Lys Lys Pro Gly Ala
1               5                   10                  15

Ser Val Lys Ile Ser Cys Glu Ala Ser Gly Tyr Asn Phe Asn Gly Tyr
            20                  25                  30

Val Ile Asp Trp Val Arg Gln Ala Pro Gly Gln Arg Leu Glu Trp Met
        35                  40                  45

Gly Trp Ile Asn Pro Gly Asn Gly Asn Thr Lys Phe Ser Pro Lys Phe
    50                  55                  60

Gln Gly Arg Val Thr Phe Thr Arg Ala Ala Ser Ala Ser Thr Ala Tyr
65                  70                  75                  80

Met Glu Leu Ser Ser Leu Thr Ser Glu Asp Thr Ala Leu Tyr Phe Cys
                85                  90                  95

Ala Arg Gly Arg Gly Thr Ser Tyr Tyr Tyr Ala Phe Asp Val Trp Gly
            100                 105                 110

Gln Gly Thr Thr Val Thr Val Ser Ser
        115                 120
```

<210> SEQ ID NO 22
<211> LENGTH: 108
<212> TYPE: PRT
<213> ORGANISM: Homo sapiens
<220> FEATURE:
<223> OTHER INFORMATION: Light chain of antibody 1T0451

<400> SEQUENCE: 22

```
Asp Ile Gln Met Thr Gln Phe Pro Ser Ser Leu Ser Ala Ser Val Gly
1               5                   10                  15

Asp Arg Val Thr Ile Ser Cys Arg Ala Ser Gln Asn Ile Ser Asn Tyr
            20                  25                  30

Leu Asn Trp Tyr Gln Gln Lys Pro Gly Lys Ala Pro Lys Phe Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Gly Phe Thr Leu Thr Ile Ser Asn Leu Gln Pro
65                  70                  75                  80

Glu Asp Phe Ala Ile Tyr Tyr Cys Gln Gln Thr Tyr Arg Ser Pro Leu
                85                  90                  95

Tyr Thr Phe Gly Gln Gly Thr Lys Leu Glu Ile Lys
            100                 105
```

<210> SEQ ID NO 23
<211> LENGTH: 114
<212> TYPE: PRT
<213> ORGANISM: Homo sapiens
<220> FEATURE:
<223> OTHER INFORMATION: Heavy chain of antibody 1T0455

<400> SEQUENCE: 23

```
Glu Val Gln Leu Val Glu Ser Gly Gly Gly Leu Val Lys Pro Gly Glu
1               5                   10                  15
```

Ser Leu Arg Leu Ser Cys Ala Val Ser Gly Leu Thr Phe Ser Asn Ala
20 25 30

Trp Met Asn Trp Val Arg Gln Ala Pro Gly Lys Gly Leu Glu Trp Val
35 40 45

Gly Arg Ile Lys Ser Lys Ser Asp Gly Gly Ala Ala Asp Tyr Ala Ala
50 55 60

Pro Val Asn Ala Arg Phe Thr Ile Ser Arg Asp Asp Ser Lys Lys Thr
65 70 75 80

Leu Tyr Leu Gln Met Asn Ser Leu Lys Thr Glu Asp Thr Gly Phe Tyr
85 90 95

Tyr Cys Thr Thr Leu Tyr His Ser Gly Gln Gly Thr Leu Val Thr Val
100 105 110

Ser Ser

<210> SEQ ID NO 24
<211> LENGTH: 112
<212> TYPE: PRT
<213> ORGANISM: Homo sapiens
<220> FEATURE:
<223> OTHER INFORMATION: Light chain of antibody 1T0455

<400> SEQUENCE: 24

Gln Ser Val Leu Thr Gln Pro Pro Ser Val Ser Gly Ala Pro Gly Gln
1 5 10 15

Arg Val Thr Ile Ser Cys Thr Gly Ser Ser Ser Asn Ile Gly Ala Gly
20 25 30

Tyr Asp Val His Trp Tyr Gln Gln Leu Pro Gly Thr Ala Pro Lys Phe
35 40 45

Val Ile Tyr Gly Asn Asn Asn Arg Pro Ser Gly Val Pro Asp Arg Phe
50 55 60

Ser Gly Ser Lys Ser Gly Thr Ser Ala Ser Leu Ala Ile Thr Gly Leu
65 70 75 80

Gln Val Glu Asp Glu Gly Asp Tyr Tyr Cys Gln Ser Tyr Asp Ser Arg
85 90 95

Leu Ser Asp His Val Val Phe Gly Gly Gly Thr Lys Leu Thr Val Leu
100 105 110

<210> SEQ ID NO 25
<211> LENGTH: 121
<212> TYPE: PRT
<213> ORGANISM: Homo sapiens
<220> FEATURE:
<223> OTHER INFORMATION: Heavy chain of antibody 1T0465

<400> SEQUENCE: 25

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Arg Phe
20 25 30

Gly Ile Asn Trp Val Arg Gln Ala Pro Gly Gln Gly Leu Glu Trp Met
35 40 45

Gly Trp Ile Ser Val Tyr Asn Gly Lys Thr Asp Tyr Ala Gln Asn Val
50 55 60

Gln Gly Arg Val Thr Met Thr Thr Asp Thr Ala Thr Ser Thr Ala Tyr
65 70 75 80

Met Glu Leu Arg Ser Leu Arg Ser Asp Asp Thr Ala Val Tyr Tyr Cys
85 90 95

```
Ala Arg Asp Ile Thr Met Val Arg Gly Gly Trp Leu Asp Tyr Trp Gly
            100                 105                 110

Gln Gly Thr Leu Ile Thr Val Ser Ser
        115                 120


<210> SEQ ID NO 26
<211> LENGTH: 106
<212> TYPE: PRT
<213> ORGANISM: Homo sapiens
<220> FEATURE:
<223> OTHER INFORMATION: Light chain of antibody 1T0465

<400> SEQUENCE: 26

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Asp Thr Asn
            20                  25                  30

Leu Ala Trp Tyr Gln Gln Lys Pro Gly Gln Ala Pro Arg Leu Leu Ile
        35                  40                  45

Tyr Tyr Ala Ser Thr Arg Ala Thr Gly Thr Pro Ala Arg Phe Ser Gly
    50                  55                  60

Ser Gly Ser Gly Thr Glu Phe Ala Leu Thr Ile Ser Ser Leu Gln Ser
65                  70                  75                  80

Glu Asp Phe Ala Val Tyr Tyr Cys Gln Gln Tyr Asn Thr Trp Ala Thr
                85                  90                  95

Phe Gly Gln Gly Thr Lys Leu Glu Ile Lys
            100                 105


<210> SEQ ID NO 27
<211> LENGTH: 126
<212> TYPE: PRT
<213> ORGANISM: Homo sapiens
<220> FEATURE:
<223> OTHER INFORMATION: Heavy chain of antibody 1T0473

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Ser Tyr
            20                  25                  30

Glu Ile Asn Trp Val Arg Gln Ala Thr Gly Gln Gly Leu Glu Trp Met
        35                  40                  45

Gly Trp Met Asp Pro Lys Ser Gly Lys Thr Gly Tyr Ala Gln Lys Phe
    50                  55                  60

Gln Gly Arg Val Thr Met Thr Arg Asn Pro Ser Ile Ser Thr Ala Tyr
65                  70                  75                  80

Leu Glu Leu Ser Ser Leu Arg Ser Glu Asp Ser Ala Val Tyr Tyr Cys
                85                  90                  95

Ala Arg Gly Asn Gln Trp Phe Gly Glu Leu Leu Ser Ser Tyr Tyr Gly
            100                 105                 110

Leu Asp Val Trp Gly Gln Gly Thr Thr Val Thr Val Ser Ser
        115                 120                 125


<210> SEQ ID NO 28
<211> LENGTH: 108
<212> TYPE: PRT
<213> ORGANISM: Homo sapiens
<220> FEATURE:
<223> OTHER INFORMATION: Light chain of antibody 1T0473
```

<400> SEQUENCE: 28

```
Glu Ile Val Leu Thr Gln Ser Pro Gly Thr Leu Ser Leu Ser Pro Gly
1               5                   10                  15

Glu Gly Ala Thr Leu Ser Cys Arg Ala Ser Gln Ser Val Ser Ser Ser
            20                  25                  30

Phe Leu Thr Trp Tyr His Gln Lys Pro Gly Gln Ala Pro Arg Leu Leu
        35                  40                  45

Ile Tyr Gly Ala Ser Asn Arg Ala Thr Gly Val Pro Asp Arg Phe Ser
    50                  55                  60

Gly Gly Gly Ser Gly Thr Asp Phe Thr Leu Thr Ile Ser Arg Leu Glu
65                  70                  75                  80

Pro Glu Asp Phe Gly Val Tyr Tyr Cys Gln Gln Tyr Gly Ser Ser Leu
                85                  90                  95

Ile Thr Phe Gly Pro Gly Thr Lys Val Asp Ile Lys
            100                 105
```

<210> SEQ ID NO 29
<211> LENGTH: 120
<212> TYPE: PRT
<213> ORGANISM: Homo sapiens
<220> FEATURE:
<223> OTHER INFORMATION: Heavy chain of antibody 1T0552

<400> SEQUENCE: 29

```
Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ser Asn Phe
            20                  25                  30

Pro Met Ser Trp Val Arg Gln Ala Pro Gly Lys Gly Leu Glu Trp Val
        35                  40                  45

Ala Ala Ile Ser Gly Ser Gly Ala Ser Ile Tyr Tyr Ala Glu Ser Val
    50                  55                  60

Arg Gly Arg Phe Thr Ile Phe Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Lys Phe Ser Gln Leu Phe Gly Tyr Ala Phe Asp Ile Trp Gly Gln
            100                 105                 110

Gly Thr Met Val Thr Val Ser Ser
        115                 120
```

<210> SEQ ID NO 30
<211> LENGTH: 108
<212> TYPE: PRT
<213> ORGANISM: Homo sapiens
<220> FEATURE:
<223> OTHER INFORMATION: Light chain of antibody 1T0552

<400> SEQUENCE: 30

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Arg Ser
            20                  25                  30

Trp Phe Ala Trp Tyr Gln Gln Lys Pro Gly Gln Ala Pro Arg Leu Leu
        35                  40                  45

Ile Tyr Gly Ala Ser Asn Arg Ala Pro Gly Ile Pro Asp Arg Phe Ser
    50                  55                  60
```

Gly Ser Gly Ser Gly Ala Asp Phe Thr Leu Thr Ile Ser Gly Leu Glu
65 70 75 80

Pro Glu Asp Phe Ala Val Tyr Tyr Cys Gln Gln Tyr Gly Asn Ser Pro
85 90 95

Trp Thr Phe Gly Gln Gly Thr Lys Val Glu Ile Lys
100 105

<210> SEQ ID NO 31
<211> LENGTH: 128
<212> TYPE: PRT
<213> ORGANISM: Homo sapiens
<220> FEATURE:
<223> OTHER INFORMATION: Heavy chain of antibody 1T0655

<400> SEQUENCE: 31

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Tyr Met His Trp Val Arg Gln Val Pro Gly Gln Gly Leu Glu Trp Met
35 40 45

Gly Ile Ile Lys Ala Gly Asn Gly Gly Thr Asn Tyr Ala Gln Asn Phe
50 55 60

Gln Gly Arg Ile Thr Val Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Asp Arg Gln Trp Leu Pro Leu Asn Gly Tyr Ser Tyr Phe Asn
100 105 110

Tyr Gly Met Asp Val Trp Gly Gln Gly Thr Thr Val Thr Val Ser Ser
115 120 125

<210> SEQ ID NO 32
<211> LENGTH: 107
<212> TYPE: PRT
<213> ORGANISM: Homo sapiens
<220> FEATURE:
<223> OTHER INFORMATION: Light chain of antibody 1T0655

<400> SEQUENCE: 32

Asp Ile Gln Met Thr Gln Ser Pro Ser Ser Leu Ser Ala Ser Val Gly
1 5 10 15

Asp Lys Ile Thr Ile Thr Cys Arg Ala Ser Gln Ser Ile Ser Thr Tyr
20 25 30

Leu Asn Trp Tyr Gln Gln Arg Pro Gly Arg Ala Pro Lys Leu Leu Ile
35 40 45

Phe Gly Ala Ser Ser Leu Gln Ser Gly Val Pro Ser Arg Phe Ser Gly
50 55 60

Ser Gly Ser Gly Thr Val Phe Thr Leu Ser Ile Ser Ser Leu Gln Pro
65 70 75 80

Asp Asp Phe Gly Ser Phe Tyr Cys Gln Gln Ser Phe Ser Ser Pro Arg
85 90 95

Thr Phe Gly Gln Gly Thr Lys Val Glu Ile Lys
100 105

<210> SEQ ID NO 33
<211> LENGTH: 126
<212> TYPE: PRT
<213> ORGANISM: Homo sapiens
<220> FEATURE:
<223> OTHER INFORMATION: Heavy chain of antibody 3T0123

<400> SEQUENCE: 33

Gln Val Gln Leu Val Gln Ser Gly Ser Glu Val Lys Lys Pro Gly Ala
1               5                   10                  15

Ser Val Lys Val Ser Cys Gln Ala Ser Gly Tyr Arg Phe Ala Asn Tyr
            20                  25                  30

Gly Ile Ser Trp Val Arg Gln Ala Pro Gly Gln Gly Leu Glu Trp Met
        35                  40                  45

Gly Trp Ile Ser Pro Leu Lys Arg Asp Pro Asp Tyr Ala Gln Asn Phe
    50                  55                  60

Gln Gly Arg Val Thr Met Ser Arg Asp Thr Ser Thr Asn Thr Ala Tyr
65                  70                  75                  80

Met Glu Leu Arg Gly Leu Thr Ser Gly Asp Thr Ala Val Tyr Phe Cys
                85                  90                  95

Ala Arg Gly Leu Gly Asp Ser Tyr Ser Asn Ala Trp Phe Val Tyr Val
            100                 105                 110

Phe Asp Tyr Trp Gly Gln Gly Ser Pro Val Thr Val Ser Ser
        115                 120                 125

<210> SEQ ID NO 34
<211> LENGTH: 106
<212> TYPE: PRT
<213> ORGANISM: Homo sapiens
<220> FEATURE:
<223> OTHER INFORMATION: Light chain of antibody 3T0123

<400> SEQUENCE: 34

Glu Ile Val Met Thr Gln Ser Pro Ala Thr Leu Ser Val Ser Pro Gly
1               5                   10                  15

Glu Arg Val Thr Leu Ser Cys Arg Thr Ser Gln Arg Ile His Thr Asn
            20                  25                  30

Leu Ala Trp Tyr Gln Gln Lys Ser Gly Gln Ala Pro Arg Leu Val Met
        35                  40                  45

Tyr Asp Ala Phe Thr Arg Ala Pro Gly Val Pro Ala Arg Phe Ser Gly
    50                  55                  60

Gly Gly Ser Glu Thr Glu Phe Thr Leu Thr Ile Ser Ser Leu Gln Ser
65                  70                  75                  80

Glu Asp Phe Ala Leu Tyr Tyr Cys Gln Gln Tyr Ser Gln Arg Pro Thr
                85                  90                  95

Phe Gly Leu Gly Thr Lys Leu Glu Ile Lys
            100                 105

<210> SEQ ID NO 35
<211> LENGTH: 118
<212> TYPE: PRT
<213> ORGANISM: Homo sapiens
<220> FEATURE:
<223> OTHER INFORMATION: Heavy chain of antibody 3T0202

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Lys Phe Arg Ser Tyr
            20                  25                  30

Asp Met His Trp Val Arg Gln Arg Ser Gly Glu Gly Leu Glu Trp Val
        35                  40                  45

```
Ala Ala Ile Gly Thr Ala Ala Asp Thr Tyr Tyr Leu Gly Ser Val Arg
    50                  55                  60

Gly Arg Phe Thr Ile Ser Arg Glu Asn Ala Lys Asn Ser Leu Tyr Leu
65                  70                  75                  80

Gln Met Asp Ser Leu Gly Ala Gly Asp Thr Ala Val Tyr Tyr Cys Ala
                85                  90                  95

Arg Ala Ala Phe Gly Ala Val Phe Phe Asp Tyr Trp Gly Gln Gly Thr
            100                 105                 110

Leu Val Thr Val Ser Ser
        115


<210> SEQ ID NO 36
<211> LENGTH: 108
<212> TYPE: PRT
<213> ORGANISM: Homo sapiens
<220> FEATURE:
<223> OTHER INFORMATION: Light chain of antibody 3T0202

<400> SEQUENCE: 36

Glu Ile Val Leu Thr Gln Ser Pro Gly Thr Leu Ser Leu Ser Ser Gly
1               5                   10                  15

Glu Arg Ala Thr Leu Ser Cys Arg Ala Ser Gln Ser Ile Ser Ser Ser
            20                  25                  30

Tyr Leu Val Trp Tyr Gln Gln Lys Leu Gly Gln Ala Pro Arg Leu Leu
        35                  40                  45

Ile Tyr Gly Ala Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asn Ser Pro
                85                  90                  95

Ile Thr Phe Gly Gln Gly Thr Arg Leu Glu Ile Lys
            100                 105


<210> SEQ ID NO 37
<211> LENGTH: 122
<212> TYPE: PRT
<213> ORGANISM: Homo sapiens
<220> FEATURE:
<223> OTHER INFORMATION: Heavy chain of antibody 3T0215

<400> SEQUENCE: 37

Glu Val Gln Leu Val Glu Ser Gly Gly Gly Ser Ile Gln Pro Gly Gly
1               5                   10                  15

Ser Leu Arg Leu Ser Cys Thr Ala Ser Gly Phe Pro Phe Ser Ala His
            20                  25                  30

Ser Phe Asn Trp Val Arg Gln Ala Pro Gly Lys Gly Leu Glu Trp Ile
        35                  40                  45

Ser Tyr Ile Asn Ser Ser Arg Thr Ser Ile Lys Tyr Ala Asp Ser Val
    50                  55                  60

Lys Gly Arg Phe Thr Val Ser Arg Asp Asn Ala Lys Gln Ser Leu Tyr
65                  70                  75                  80

Leu Gln Met Asn Ser Leu Gly Val Glu Asp Thr Ala Leu Tyr Tyr Cys
                85                  90                  95

Ala Arg Asp Thr Leu Glu Ala Gly Ser Trp Tyr Pro Phe Asp Lys Trp
            100                 105                 110

Gly His Gly Thr Leu Val Thr Val Ser Ser
        115                 120
```

<210> SEQ ID NO 38
<211> LENGTH: 108
<212> TYPE: PRT
<213> ORGANISM: Homo sapiens
<220> FEATURE:
<223> OTHER INFORMATION: Light chain of antibody 3T0215

<400> SEQUENCE: 38

```
Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Gln Lys Tyr Val
            20                  25                  30

Tyr Trp Tyr Gln Gln Lys Ser Val Gln Ala Pro Val Leu Val Ile Tyr
        35                  40                  45

Glu Asp Ser Lys Arg Pro Ser Gly Ile Pro Glu Arg Phe Ser Gly Ser
    50                  55                  60

Ser Ser Gly Thr Leu Ala Thr Leu Arg Ile Ser Gly Ala Gln Val Glu
65                  70                  75                  80

Asp Glu Ala Asp Tyr Tyr Cys Tyr Ser Thr Asp Ser Ser Gly Thr Gln
                85                  90                  95

Arg Val Phe Gly Gly Gly Thr Lys Leu Thr Val Leu
            100                 105
```

<210> SEQ ID NO 39
<211> LENGTH: 120
<212> TYPE: PRT
<213> ORGANISM: Homo sapiens
<220> FEATURE:
<223> OTHER INFORMATION: Heavy chain of antibody 3T0245

<400> SEQUENCE: 39

```
Glu Val Gln Leu Val Glu Ser Gly Gly Asp Leu Val Lys Pro Gly Gly
1               5                   10                  15

Ser Leu Arg Leu Ser Cys Glu Ala Ser Gly Phe Thr Phe Thr Asn Ala
            20                  25                  30

Trp Met Asn Trp Val Arg Gln Ser Pro Gly Lys Gly Leu Glu Trp Ile
        35                  40                  45

Gly Arg Val Lys Ser Lys Ser Asp Gly Gly Ala Ala Asp Tyr Ala Ala
    50                  55                  60

Pro Val Lys Gly Arg Phe Thr Ile Ser Arg Asp Asp Ser Lys Asn Ser
65                  70                  75                  80

Val Phe Leu Gln Met Arg Ser Leu Lys Pro Glu Asp Thr Gly Val Tyr
                85                  90                  95

Tyr Cys Ala Thr Arg Val His Tyr Asn Gly Met Asp Val Trp Gly Arg
            100                 105                 110

Gly Thr Thr Val Thr Val Ser Ser
        115                 120
```

<210> SEQ ID NO 40
<211> LENGTH: 111
<212> TYPE: PRT
<213> ORGANISM: Homo sapiens
<220> FEATURE:
<223> OTHER INFORMATION: Light chain of antibody 3T0245

<400> SEQUENCE: 40

```
Gln Ser Val Leu Thr Gln Pro Pro Ser Val Ser Gly Ala Pro Gly Gln
1               5                   10                  15
```

```
Arg Val Thr Ile Ser Cys Ala Gly Ser Gly Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Ala Asn His Asn Arg Pro Ser Gly Val Pro Asp Arg Phe
    50                  55                  60

Ser Gly Ser Lys Ser Gly Ser Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Arg Asp Ala Cys Val Phe Gly Gly Gly Thr Lys Leu Thr Val
            100                 105                 110


<210> SEQ ID NO 41
<211> LENGTH: 119
<212> TYPE: PRT
<213> ORGANISM: Homo sapiens
<220> FEATURE:
<223> OTHER INFORMATION: Heavy chain of antibody 3T0253

<400> SEQUENCE: 41

Glu Val Gln Leu Val Glu Ser Gly Gly Gly Leu Val Lys Pro Gly Arg
1               5                   10                  15

Ser Leu Arg Ile Ser Cys Ala Ala Ser Gly Ile Thr Phe Asn Lys Ala
            20                  25                  30

Trp Met Asn Trp Val Arg Leu Ala Pro Gly Lys Gly Leu Glu Trp Val
        35                  40                  45

Gly Arg Ile Lys Ser Asn Gly Asp Gly Gly Lys Arg Asp Tyr Ala Ala
    50                  55                  60

Pro Val Thr Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Phe Arg Thr Thr Arg His His Arg Gly Met Asp Val Trp Gly Gln Gly
            100                 105                 110

Thr Thr Val Thr Val Ser Ser
        115


<210> SEQ ID NO 42
<211> LENGTH: 112
<212> TYPE: PRT
<213> ORGANISM: Homo sapiens
<220> FEATURE:
<223> OTHER INFORMATION: Light chain of antibody 3T0253

<400> SEQUENCE: 42

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln His Leu Pro Gly Ala Ala Pro Lys Leu
        35                  40                  45

Leu Ile Tyr Gly Asp Gly Ser Arg Pro Ser Gly Val Pro Asp Arg Phe
    50                  55                  60

Ser Ala Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95
```

Leu Ser Asp Ala Val Val Phe Gly Gly Gly Thr Lys Leu Thr Val Leu
100 105 110

<210> SEQ ID NO 43
<211> LENGTH: 119
<212> TYPE: PRT
<213> ORGANISM: Homo sapiens
<220> FEATURE:
<223> OTHER INFORMATION: Heavy chain of antibody 3T0258

<400> SEQUENCE: 43

Gln Val Gln Leu Val Gln Ser Gly Ala Glu Val Lys Gln Pro Gly Ala
1 5 10 15

Ser Val Lys Val Thr Cys Lys Ala Ser Gly Ser Thr Arg Ser Ser Tyr
20 25 30

Asp Leu Ile Trp Val Arg Gln Ala Pro Gly Gln Gly Leu Glu Leu Met
35 40 45

Gly Arg Val Asn Thr His Asn Gly Asn Thr Asp Tyr Ala Gln Lys Phe
50 55 60

Gln Gly Arg Val Thr Met Thr Thr Asp Thr Ser Thr Thr Thr Ala His
65 70 75 80

Met Glu Leu Arg Asn Leu Arg Ser Asp Asp Thr Ala Val Tyr Tyr Cys
85 90 95

Ala Trp Arg Arg Ser Ser Trp Phe Ala Phe Asp Val Trp Gly Gln Gly
100 105 110

Thr Ala Val Thr Val Ser Ser
115

<210> SEQ ID NO 44
<211> LENGTH: 108
<212> TYPE: PRT
<213> ORGANISM: Homo sapiens
<220> FEATURE:
<223> OTHER INFORMATION: Light chain of antibody 3T0258

<400> SEQUENCE: 44

Glu Ile Val Leu Thr Gln Ser Pro Gly Thr Leu Ser Leu Ser Pro Gly
1 5 10 15

Glu Arg Gly Thr Leu Ser Cys Arg Ala Ser Gln Ser Ile Ser Gly Asn
20 25 30

Tyr Leu Gly Trp Tyr Gln Gln Ser Pro Gly Gln Ala Pro Arg Leu Leu
35 40 45

Ile Tyr Gly Ala Ser Asn Arg Ala Thr Gly Val Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Val Ser Ser Pro
85 90 95

Tyr Thr Phe Gly Gln Gly Thr Lys Leu Glu Ile Lys
100 105

<210> SEQ ID NO 45
<211> LENGTH: 117
<212> TYPE: PRT
<213> ORGANISM: Homo sapiens
<220> FEATURE:
<223> OTHER INFORMATION: Heavy chain of antibody 3T0265

<400> SEQUENCE: 45

```
Glu Val Gln Leu Val Glu Ser Gly Gly Asn Leu Ala Lys Pro Gly Gly
1               5                   10                  15

Ser Leu Arg Leu Ser Cys Ala Ala Ser Gly Phe Thr Phe Ser Asp Ala
            20                  25                  30

Trp Met Thr Trp Val Arg Gln Ala Pro Gly Lys Gly Leu Glu Trp Val
        35                  40                  45

Gly Arg Ile Lys Ser Asn Ala Asp Gly Gly Ala Thr Glu Tyr Ala Ala
    50                  55                  60

Pro Val Arg Gly Arg Phe Thr Ile Ser Arg Asp Asp Ser Arg Ser Ser
65                  70                  75                  80

Leu Phe Leu Gln Met Asn Ser Leu Lys Thr Glu Asp Thr Ala Val Tyr
                85                  90                  95

Tyr Cys Leu Thr Pro Pro Pro Arg Arg Tyr Trp Gly Gln Gly Ile Leu
            100                 105                 110

Val Thr Val Ser Ser
        115
```

<210> SEQ ID NO 46
<211> LENGTH: 111
<212> TYPE: PRT
<213> ORGANISM: Homo sapiens
<220> FEATURE:
<223> OTHER INFORMATION: Light chain of antibody 3T0265

<400> SEQUENCE: 46

```
Gln Ser Val Leu Thr Gln Pro Pro Ser Val Ser Gly Ala Pro Gly Gln
1               5                   10                  15

Arg Val Ala Ile Ser Cys Thr Gly Ser Tyr Ser Asn Ile Gly Ala Gly
            20                  25                  30

Tyr Asp Val His Trp Tyr Gln Gln Phe Pro Gly Ala Ala Pro Lys Leu
        35                  40                  45

Leu Ile Tyr Ala Tyr Thr Asn Arg Pro Ala Gly Val Pro Asp Arg Phe
    50                  55                  60

Ser Gly Ser Lys Ser Gly Ser Ser Ala Ser Leu Val Ile Ser Gly Leu
65                  70                  75                  80

Gln Ala Asp Asp Glu Ala Asp Tyr Tyr Cys Gln Ser Tyr Asp Ala Arg
                85                  90                  95

Leu Arg Asp Gly Glu Val Phe Gly Gly Gly Thr Lys Leu Thr Val
            100                 105                 110
```

<210> SEQ ID NO 47
<211> LENGTH: 121
<212> TYPE: PRT
<213> ORGANISM: Homo sapiens
<220> FEATURE:
<223> OTHER INFORMATION: Heavy chain of antibody 3T0331

<400> SEQUENCE: 47

```
Glu Val Gln Leu Leu Glu Ser Gly Gly Gly Leu Val Gln Pro Gly Gly
1               5                   10                  15

Ser Leu Arg Leu Ser Cys Glu Ala Ser Gly Phe Pro Leu Arg Asp Tyr
            20                  25                  30

Ala Met Ser Trp Val Arg Gln Ala Pro Gly Arg Gly Leu Gln Trp Val
        35                  40                  45

Ser Thr Ile Gly Gly Asn Asp Asn Ala Ala Asn Tyr Ala Asp Ser Val
    50                  55                  60

Lys Gly Arg Phe Thr Val Ser Arg Asp Asn Ser Lys Ser Thr Ile Tyr
65                  70                  75                  80
```

```
Leu Gln Met Asn Ser Leu Arg Ala Glu Asp Thr Ala Leu Tyr Phe Cys
                85                  90                  95

Ala Lys Ser Val Arg Leu Ser Arg Pro Ser Pro Phe Asp Leu Trp Gly
            100                 105                 110

Gln Gly Ser Leu Val Thr Val Ser Ser
        115                 120


<210> SEQ ID NO 48
<211> LENGTH: 107
<212> TYPE: PRT
<213> ORGANISM: Homo sapiens
<220> FEATURE:
<223> OTHER INFORMATION: Light chain of antibody 3T0331

<400> SEQUENCE: 48

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Thr Tyr
            20                  25                  30

Leu Ala Trp Tyr Gln His Gln Pro Gly Gln Ala Pro Arg Leu Leu Ile
        35                  40                  45

Tyr Glu Ala Ser Asn Arg Ala Thr Gly Ile Pro Ala Arg Phe Ser Gly
    50                  55                  60

Ser Gly Ser Gly Thr Glu Phe Thr Leu Thr Ile Ser Ser Leu Glu Pro
65                  70                  75                  80

Glu Asp Val Ala Val Tyr Tyr Cys Gln Gln Arg Ala Ser Trp Pro Leu
                85                  90                  95

Thr Phe Gly Gly Gly Thr Lys Val Glu Ile Lys
            100                 105


<210> SEQ ID NO 49
<211> LENGTH: 125
<212> TYPE: PRT
<213> ORGANISM: Homo sapiens
<220> FEATURE:
<223> OTHER INFORMATION: Heavy chain of antibody 3T0338

<400> SEQUENCE: 49

Glu Val Gln Leu Val Glu Ser Gly Gly Ala Leu Val Lys Pro Gly Gly
1               5                   10                  15

Ser Leu Arg Leu Ser Cys Ala Ala Ser Gly Phe Ser Phe Lys Thr Ala
            20                  25                  30

Trp Met Asn Trp Val Arg Gln Ala Pro Gly Lys Gly Leu Glu Trp Val
        35                  40                  45

Gly Arg Ile Lys Ser Arg Ala Asp Gly Gly Thr Ser Asp Tyr Ser Ala
    50                  55                  60

Ser Val Lys Gly Arg Phe Thr Phe Ser Arg Asp Asp Ser Lys Asn Thr
65                  70                  75                  80

Leu Tyr Leu Gln Met Thr Ser Leu Lys Thr Glu Asp Thr Gly Met Tyr
                85                  90                  95

Tyr Cys Thr Thr Leu Asn Leu Gly Gly Gly Phe Pro Gly Glu Trp Arg
            100                 105                 110

Ser Val Trp Gly Gln Gly Thr Thr Val Thr Val Ser Ser
        115                 120                 125


<210> SEQ ID NO 50
<211> LENGTH: 112
<212> TYPE: PRT
```

<213> ORGANISM: Homo sapiens
<220> FEATURE:
<223> OTHER INFORMATION: Light chain of antibody 3T0338

<400> SEQUENCE: 50

Gln Ser Val Leu Thr Gln Pro Pro Ser Val Ser Gly Ala Pro Gly Gln
1 5 10 15

Arg Val Thr Ile Ser Cys Thr Gly Ser Tyr Ser Asn Ile Gly Ser Gly
20 25 30

Tyr Asp Val Leu Trp Tyr Gln Gln Leu Pro Gly Ala Ala Pro Lys Leu
35 40 45

Leu Ile Tyr Gly Asn Asn Asn Arg Pro Ser Gly Val Pro Asp Arg Phe
50 55 60

Ser Gly Ser Lys Ser Gly Thr Ser Ala Ser Leu Ala Ile Thr Glu Leu
65 70 75 80

Gln Ala Glu Asp Glu Gly Asp Tyr Tyr Cys Gln Ser Tyr Asp Ser Arg
85 90 95

Leu Arg Asp Ser Trp Val Phe Gly Gly Gly Thr Arg Leu Thr Val Leu
100 105 110

<210> SEQ ID NO 51
<211> LENGTH: 122
<212> TYPE: PRT
<213> ORGANISM: Homo sapiens
<220> FEATURE:
<223> OTHER INFORMATION: Heavy chain of antibody 3T0350

<400> SEQUENCE: 51

Glu Val Gln Leu Leu Glu Ser Gly Gly Gly Leu Val Gln Pro Gly Gly
1 5 10 15

Ser Leu Arg Leu Ser Cys Thr Ala Ser Gly Phe Ala Phe Gly Asn Tyr
20 25 30

Ala Met Asn Trp Val Arg Gln Ala Pro Gly Lys Gly Leu Ala Trp Val
35 40 45

Ala Gly Val Thr Gly Ser Gly Gly Thr Thr Ile Tyr Ala Asp Ser Val
50 55 60

Lys Gly Arg Phe Thr Ile Ser Lys Asp Ile Ser Lys Asn Thr Val Tyr
65 70 75 80

Leu Gln Met Ser Ser Leu Arg Ala Glu Asp Thr Ala Val Tyr Tyr Cys
85 90 95

Ala Lys Asp Leu Lys Gly Asn Trp Asn Asp Gly Pro Phe Asp Tyr Trp
100 105 110

Gly Gln Gly Ala Leu Val Thr Val Ser Ser
115 120

<210> SEQ ID NO 52
<211> LENGTH: 112
<212> TYPE: PRT
<213> ORGANISM: Homo sapiens
<220> FEATURE:
<223> OTHER INFORMATION: Light chain of antibody 3T0350

<400> SEQUENCE: 52

Gln Ser Val Leu Thr Gln Pro Pro Ser Val Ser Ala Ala Pro Gly Gln
1 5 10 15

Lys Val Thr Ile Ser Cys Ser Gly Ser Arg Ser Asn Ile Gly Thr Asn
20 25 30

Tyr Val Ser Trp Tyr Gln Gln Leu Pro Gly Thr Ala Pro Lys Leu Leu
35 40 45

```
Ile Tyr Asp Asn Asp Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Glu Tyr Tyr Cys Gly Thr Trp Gly Asn Ser Leu
                85                  90                  95

Ser Gly Pro Glu Trp Val Phe Gly Gly Gly Thr Arg Val Thr Val Leu
            100                 105                 110


<210> SEQ ID NO 53
<211> LENGTH: 117
<212> TYPE: PRT
<213> ORGANISM: Homo sapiens
<220> FEATURE:
<223> OTHER INFORMATION: Heavy chain of antibody 3T0405

<400> SEQUENCE: 53

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Ala
        35                  40                  45

Ala Val Ile Leu Tyr Asp Gly Ser Lys Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asn Tyr Arg Asp Ser Glu Leu Glu Trp Gly Gln Gly Thr Leu
            100                 105                 110

Val Thr Val Ser Ser
        115


<210> SEQ ID NO 54
<211> LENGTH: 112
<212> TYPE: PRT
<213> ORGANISM: Homo sapiens
<220> FEATURE:
<223> OTHER INFORMATION: Light chain of antibody 3T0405

<400> SEQUENCE: 54

Asp Val Val Met Thr Gln Ser Pro Leu Ser Leu Thr Val Thr Leu Gly
1               5                   10                  15

Gln Pro Ala Ser Ile Ser Cys Arg Ser Ser Gln Ser Leu Leu His Ser
            20                  25                  30

Asp Gly Asn Thr Tyr Leu Asn Trp Phe His Gln Arg Pro Gly Gln Ser
        35                  40                  45

Pro Arg Arg Leu Ile Phe Lys Val Ser Asp Arg Asp Ser Gly Val Pro
    50                  55                  60

Glu Arg Phe Ser Gly Arg Gly Ser Asp Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Leu Trp Pro Trp Thr Phe Gly Gln Gly Thr Lys Val His Val Lys
            100                 105                 110
```

<210> SEQ ID NO 55
<211> LENGTH: 113
<212> TYPE: PRT
<213> ORGANISM: Homo sapiens
<220> FEATURE:
<223> OTHER INFORMATION: Heavy chain of antibody 3T0415

<400> SEQUENCE: 55

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ala Phe Ser Thr Tyr
            20                  25                  30

Ala Met Ser Trp Val Arg Gln Ala Pro Gly Lys Gly Leu Glu Trp Val
        35                  40                  45

Ser Ala Val Gly Gly Gly Gly Thr Asn Thr His Tyr Ala Asp Ser Val
    50                  55                  60

Lys Gly Arg Phe Thr Ile Ser Arg Asp Asn Ser Gln Asn Thr Leu Tyr
65                  70                  75                  80

Leu Gln Met Asp Ser Leu Arg Val Asp Asp Thr Ala Val Tyr Tyr Cys
                85                  90                  95

Ala Ile Asn Gly Gly Val Trp Gly Gln Gly Thr Ala Val Thr Val Ser
            100                 105                 110

Ser
```

<210> SEQ ID NO 56
<211> LENGTH: 113
<212> TYPE: PRT
<213> ORGANISM: Homo sapiens
<220> FEATURE:
<223> OTHER INFORMATION: Light chain of antibody 3T0415

<400> SEQUENCE: 56

```
Asp Ile Val Met Thr Gln Ser Pro Asp Ser Leu Thr Val Ser Leu Gly
1               5                   10                  15

Glu Arg Ala Thr Ile Thr Cys Lys Ser Ser Arg Ser Val Phe Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Ser Trp Ala Ser Thr Arg Glu Ser Gly Val
    50                  55                  60

Pro Asp Arg Phe Ser Gly Ser Gly Ser Gly Thr Glu Phe Ser Leu Thr
65                  70                  75                  80

Ile Ser Ser Leu Gln Ala Glu Asp Val Ala Val Tyr Tyr Cys Gln Gln
                85                  90                  95

His Tyr Ala Thr Arg Val Thr Phe Gly Gly Gly Thr Lys Val Glu Ile
            100                 105                 110

Lys
```

<210> SEQ ID NO 57
<211> LENGTH: 118
<212> TYPE: PRT
<213> ORGANISM: Homo sapiens
<220> FEATURE:
<223> OTHER INFORMATION: Heavy chain of antibody 3T0468

<400> SEQUENCE: 57

```
Glu Val Gln Leu Val Glu Ser Gly Gly His Leu Ile Gln Pro Gly Gly
1               5                   10                  15

Ser Leu Arg Leu Ser Cys Ala Ala Ser Gly Phe Thr Phe Arg Ile Tyr
```

```
            20                  25                  30

Asp Met His Trp Val Arg Gln Gly Arg Arg Lys Gly Leu Glu Trp Val
        35                  40                  45

Ser Ala Ile Gly Ala Ala Gly Asp Thr Tyr Tyr Ser Asp Ser Val Lys
    50                  55                  60

Gly Arg Phe Thr Ile Ser Arg Glu Asn Ala Lys Ser Ser Leu Tyr Leu
65                  70                  75                  80

Gln Met Asn Ser Leu Ser Val Gly Asp Thr Ala Val Tyr Tyr Cys Ala
                85                  90                  95

Arg Ala Ala Phe Gly Ala Val Tyr Tyr Asp Asn Trp Gly Gln Gly Ile
            100                 105                 110

Leu Val Thr Val Ser Ser
        115


<210> SEQ ID NO 58
<211> LENGTH: 108
<212> TYPE: PRT
<213> ORGANISM: Homo sapiens
<220> FEATURE:
<223> OTHER INFORMATION: Light chain of antibody 3T0468

<400> SEQUENCE: 58

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Glu Asn Val Asp Ser Arg
            20                  25                  30

Phe Leu Val Trp Tyr Gln Gln Lys Val Gly Gln Ala Pro Arg Leu Leu
        35                  40                  45

Ile Tyr Gly Ala Ser Arg Arg Ala Thr Gly Ile Pro Asp Arg Phe Ser
    50                  55                  60

Gly Ser Gly Ser Gly Thr Asp Phe Ala Leu Thr Ile Ser Arg Leu Glu
65                  70                  75                  80

Pro Glu Asp Leu Ala Val Tyr Tyr Cys Gln Gln Tyr Gly Arg Ser Pro
                85                  90                  95

Ile Thr Phe Gly Gln Gly Thr Arg Leu Glu Ile Lys
            100                 105


<210> SEQ ID NO 59
<211> LENGTH: 123
<212> TYPE: PRT
<213> ORGANISM: Homo sapiens
<220> FEATURE:
<223> OTHER INFORMATION: Heavy chain of antibody 3T0478

<400> SEQUENCE: 59

Val Gln Leu Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Asn Trp Ile Arg Gln Ser Pro Gly Lys Gly Leu Glu Trp Met
        35                  40                  45

Gly Tyr Ile Tyr Tyr Thr Gly Ser Thr Asn Tyr Asn Pro Ser Leu Lys
    50                  55                  60

Ser Arg Val Thr Ile Ser Val Asp Leu Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95
```

```
Arg Asp Lys Arg Tyr Tyr Asp Ser Ser Gly Tyr Ser His Phe Asp Tyr
            100                 105                 110

Trp Gly Gln Gly Ile Leu Val Thr Val Ser Ser
        115                 120


<210> SEQ ID NO 60
<211> LENGTH: 110
<212> TYPE: PRT
<213> ORGANISM: Homo sapiens
<220> FEATURE:
<223> OTHER INFORMATION: Light chain of antibody 3T0478

<400> SEQUENCE: 60

Gln Ser Val Leu Thr Gln Pro Pro Ser Ala Ser Gly Thr Pro Gly Gln
1               5                   10                  15

Arg Val Thr Ile Phe Cys Ser Gly Ser Ser Phe Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Glu Arg Pro Ser Gly Val Pro Asp Arg Phe Ser
    50                  55                  60

Gly Ser Lys Ser Gly Thr Ser Ala Ser Leu Asp Ile Ser Gly Leu Arg
65                  70                  75                  80

Ser Glu Asp Glu Ala Asp Tyr Ser Cys Ala Ala Trp Asp Gly Ser Leu
                85                  90                  95

Ser Gly Pro Val Phe Gly Gly Gly Thr Lys Leu Thr Val Leu
            100                 105                 110


<210> SEQ ID NO 61
<211> LENGTH: 127
<212> TYPE: PRT
<213> ORGANISM: Homo sapiens
<220> FEATURE:
<223> OTHER INFORMATION: Heavy chain of antibody 3T0553

<400> SEQUENCE: 61

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Thr Thr Cys
            20                  25                  30

Ala Met His Trp Val Arg Gln Ala Pro Gly Lys Gly Leu Glu Trp Val
        35                  40                  45

Ser Val Met Trp Tyr Asp Gly Ser Arg Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Glu Met Gln Ser Leu Arg Ala Glu Asp Thr Ala Val Tyr Tyr Cys
                85                  90                  95

Ala Arg Gly Gly Asp Leu Leu Val Glu Val Asp Ser Thr Asp Tyr Tyr
            100                 105                 110

Gly Leu Asp Val Trp Gly Gln Gly Thr Thr Val Thr Val Ser Ser
        115                 120                 125


<210> SEQ ID NO 62
<211> LENGTH: 107
<212> TYPE: PRT
<213> ORGANISM: Homo sapiens
<220> FEATURE:
<223> OTHER INFORMATION: Light chain of antibody 3T0553
```

<400> SEQUENCE: 62

```
Asp Ile Gln Met Thr Gln Ser Pro Ser Ala Met Ser Ala Ser Val Gly
1               5                   10                  15

Asp Arg Val Thr Ile Thr Cys Arg Ala Ser Gln Gly Ile Ser His Ser
            20                  25                  30

Leu Ala Trp Phe Gln Gln Lys Pro Gly Lys Val Pro Lys Arg Leu Ile
        35                  40                  45

Tyr Ser Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Arg Tyr Pro Trp
                85                  90                  95

Thr Phe Gly Gln Gly Thr Lys Val Glu Ile Lys
            100                 105
```

<210> SEQ ID NO 63
<211> LENGTH: 121
<212> TYPE: PRT
<213> ORGANISM: Homo sapiens
<220> FEATURE:
<223> OTHER INFORMATION: Heavy chain of antibody 3T0611

<400> SEQUENCE: 63

```
Glu Val Gln Leu Val Glu Ser Gly Gly Asn Leu Val Gln Pro Gly Gly
1               5                   10                  15

Ser Leu Arg Leu Ser Cys Ala Ala Ser Gly Phe Thr Phe Arg Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ala Ser Ile Ile His Tyr Ala Glu Ser Val
    50                  55                  60

Gln Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Gly Ile Leu Asp Asp Tyr Arg Asp Tyr Gly Tyr Asp Tyr Trp Gly
            100                 105                 110

Gln Gly Thr Leu Val Thr Val Ser Ser
        115                 120
```

<210> SEQ ID NO 64
<211> LENGTH: 109
<212> TYPE: PRT
<213> ORGANISM: Homo sapiens
<220> FEATURE:
<223> OTHER INFORMATION: Light chain of antibody 3T0611

<400> SEQUENCE: 64

```
Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Arg Pro Gly Gln Ala Pro Val Leu Val Ile Tyr
        35                  40                  45

Lys Asp Ile Glu Arg Pro Ser Gly Ile Pro Glu Arg Tyr Ser Gly Ser
    50                  55                  60
```

Ser Ser Gly Ala Ile Val Thr Leu Thr Ile Ser Gly Ala Gln Ala Glu
65 70 75 80

Asp Glu Ala Asp Tyr Tyr Cys Gln Ser Ser Asp Asn Asn Gly Ser Tyr
85 90 95

Arg Val Met Phe Gly Gly Gly Thr Lys Leu Thr Val Leu
100 105

<210> SEQ ID NO 65
<211> LENGTH: 119
<212> TYPE: PRT
<213> ORGANISM: Homo sapiens
<220> FEATURE:
<223> OTHER INFORMATION: Heavy chain of antibody 3T0650

<400> SEQUENCE: 65

Glu Val Gln Leu Val Gln Ser Gly Gly Gly Leu Val Lys Pro Gly Gly
1 5 10 15

Ser Leu Arg Leu Ser Cys Ala Ala Ser Gly Phe Thr Phe Ser Asn Ala
20 25 30

Trp Met Asn Trp Val Arg Gln Ala Pro Gly Lys Gly Leu Glu Trp Ile
35 40 45

Gly Arg Val Lys Ser Gln Thr Asp Arg Gly Thr Lys Asp Tyr Ala Ala
50 55 60

Pro Val Lys Gly Arg Phe Ser Ile Ser Arg Asp Asp Ser Lys Lys Met
65 70 75 80

Leu Tyr Leu Gln Met Asn Ser Leu Lys Ile Glu Asp Thr Gly Val Tyr
85 90 95

Tyr Cys Val Ala Thr Pro His Ser Trp Ser Val Ala Trp Gly Gln Gly
100 105 110

Thr Leu Val Thr Val Ser Ser
115

<210> SEQ ID NO 66
<211> LENGTH: 112
<212> TYPE: PRT
<213> ORGANISM: Homo sapiens
<220> FEATURE:
<223> OTHER INFORMATION: Light chain of antibody 3T0650

<400> SEQUENCE: 66

Gln Ser Val Leu Thr Gln Pro Pro Ser Val Ser Gly Ala Pro Gly Gln
1 5 10 15

Arg Val Thr Ile Ser Cys Thr Gly Ser Ser Ser Asn Ile Gly Ala Gly
20 25 30

Tyr Asp Val Gln Trp Tyr Gln Gln Phe Pro Gly Thr Ala Pro Lys Leu
35 40 45

Leu Ile Tyr Gly Asn Ile Asn Arg Pro Ser Gly Val Pro Asp Arg Phe
50 55 60

Ser Gly Ser Lys Ser Gly Ser Ser Ala Ser Leu Ala Ile Thr Arg Leu
65 70 75 80

Gln Ala Glu Asp Glu Ala Asp Tyr Tyr Cys Gln Ser Tyr Asp Ser Ser
85 90 95

Leu Arg Asp Gln Trp Val Phe Gly Gly Gly Thr Lys Leu Thr Val Leu
100 105 110

<210> SEQ ID NO 67
<211> LENGTH: 123
<212> TYPE: PRT
<213> ORGANISM: Homo sapiens
<220> FEATURE:
<223> OTHER INFORMATION: Heavy chain of antibody 3T0673

<400> SEQUENCE: 67

```
Glu Val Gln Leu Val Glu Ser Gly Gly Gly Arg Val Lys Pro Gly Gly
1               5                   10                  15

Ser Leu Arg Val Ser Cys Ala Val Ser Gly Ile Thr Phe Thr Asn Ala
            20                  25                  30

Trp Met Thr Trp Val Arg Gln Ala Pro Gly Lys Gly Leu Glu Trp Leu
        35                  40                  45

Gly Arg Ile Lys Ser Arg Ser Asp Gly Gly Gln Ser Asp Leu Ile Ala
    50                  55                  60

Pro Val Lys Gly Arg Phe Thr Ile Ser Arg Asp Asp Ser Lys Asn Ile
65                  70                  75                  80

Leu Tyr Leu Gln Met Asn Asn Leu Lys Thr Glu Asp Thr Gly Leu Tyr
                85                  90                  95

Phe Cys Thr Thr Tyr Tyr Tyr Asp Asn Gly Gly Ser Tyr Ser Asn Pro
            100                 105                 110

Trp Gly Leu Gly Thr Leu Val Thr Val Ser Ser
        115                 120
```

<210> SEQ ID NO 68
<211> LENGTH: 112
<212> TYPE: PRT
<213> ORGANISM: Homo sapiens
<220> FEATURE:
<223> OTHER INFORMATION: Light chain of antibody 3T0673

<400> SEQUENCE: 68

```
Gln Ser Val Leu Thr Gln Pro Pro Ser Val Ser Gly Ala Pro Gly Gln
1               5                   10                  15

Arg Val Thr Ile Ser Cys Thr Gly Ser Tyr Ser Asn Ile Gly Ala Gly
            20                  25                  30

Tyr Asp Val Leu Trp Tyr Gln Gln Leu Pro Gly Thr Ala Pro Lys Leu
        35                  40                  45

Leu Ile Tyr Gly Asn Asn Lys Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Arg
                85                  90                  95

Leu Arg Asp Phe Gly Ile Phe Gly Gly Gly Thr Lys Leu Thr Val Leu
            100                 105                 110
```

<210> SEQ ID NO 69
<211> LENGTH: 120
<212> TYPE: PRT
<213> ORGANISM: Homo sapiens
<220> FEATURE:
<223> OTHER INFORMATION: Heavy chain of antibody 4m0333

<400> SEQUENCE: 69

```
Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Ala Phe Ser Ser Tyr
            20                  25                  30

Ala Met Asn Trp Val Arg Gln Ala Pro Gly Lys Gly Leu Glu Trp Val
        35                  40                  45
```

```
Ser Gly Ile Thr Gly Ser Gly Gly Thr Thr Tyr Tyr Pro Asp Ser Met
    50                  55                  60

Lys Gly Arg Phe Thr Ile Ser Arg Asp Asn Ser Lys Asn Thr Leu Tyr
65                  70                  75                  80

Leu Gln Met Asn Ser Leu Gly Gly Glu Asp Thr Ala Thr Tyr Tyr Cys
                85                  90                  95

Ala Lys Gly Asp Asp Phe Trp Ser Gly Ser Pro Asp Val Trp Gly Gln
            100                 105                 110

Gly Thr Thr Val Thr Val Ser Ser
        115                 120


<210> SEQ ID NO 70
<211> LENGTH: 111
<212> TYPE: PRT
<213> ORGANISM: Homo sapiens
<220> FEATURE:
<223> OTHER INFORMATION: Light chain of antibody 4m0333

<400> SEQUENCE: 70

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Thr Asn
            20                  25                  30

Tyr Val Ser Trp Tyr Gln Gln Leu Pro Gly Ala Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Thr Phe Tyr Val Phe Gly Gly Gly Thr Lys Val Asn Val Leu
            100                 105                 110


<210> SEQ ID NO 71
<211> LENGTH: 116
<212> TYPE: PRT
<213> ORGANISM: Homo sapiens
<220> FEATURE:
<223> OTHER INFORMATION: Heavy chain of antibody 4m0368

<400> SEQUENCE: 71

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Gly Thr
            20                  25                  30

Asn Trp Trp Thr Trp Val Arg Gln Pro Pro Gly Arg Gly Leu Glu Trp
        35                  40                  45

Ile Gly Glu Ile Tyr Tyr Arg Gly Ser Pro Asn Tyr Asn Pro Ser Leu
    50                  55                  60

Lys Ser Arg Val Thr Ile Ser Val Asp Gln Ser Lys Ser Gln Phe Ser
65                  70                  75                  80

Leu Lys Leu Thr Ser Val Thr Ala Ala Asp Thr Ala Val Tyr Tyr Cys
                85                  90                  95

Leu Arg Leu Ser His Tyr Gly Gly Ala Trp Gly Gln Gly Thr Leu Val
            100                 105                 110

Thr Val Ser Ser
        115
```

<210> SEQ ID NO 72
<211> LENGTH: 107
<212> TYPE: PRT
<213> ORGANISM: Homo sapiens
<220> FEATURE:
<223> OTHER INFORMATION: Light chain of antibody 4m0368

<400> SEQUENCE: 72

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Lys Pro Gly Lys Ala Pro Lys Phe Leu Ile
        35                  40                  45

Phe Ser Ala Ser Asn Leu Gln Ser Gly Val Pro Ser Arg Phe Ser Gly
    50                  55                  60

Gly Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Asn Thr Pro Arg
                85                  90                  95

Thr Phe Gly Gln Gly Thr Lys Val Glu Ile Lys
            100                 105
```

<210> SEQ ID NO 73
<211> LENGTH: 122
<212> TYPE: PRT
<213> ORGANISM: Homo sapiens
<220> FEATURE:
<223> OTHER INFORMATION: Heavy chain of antibody 4m0373

<400> SEQUENCE: 73

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp His
            20                  25                  30

Tyr Met Gly Trp Ile Arg Gln Ala Pro Gly Lys Gly Leu Glu Trp Val
        35                  40                  45

Ser Tyr Ile Ser Thr Tyr Ala Thr Thr Ala Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Glu Arg Arg His Gln Val Leu Ser Gly Met Asp Val Trp
            100                 105                 110

Gly Gln Gly Thr Thr Val Thr Val Ser Ser
        115                 120
```

<210> SEQ ID NO 74
<211> LENGTH: 105
<212> TYPE: PRT
<213> ORGANISM: Homo sapiens
<220> FEATURE:
<223> OTHER INFORMATION: Light chain of antibody 4m0373

<400> SEQUENCE: 74

```
Phe Met Thr Gln Ala Pro Ser Ser Leu Ser Val Ser Pro Gly Glu Arg
1               5                   10                  15
```

```
Ala Thr Leu Ser Cys Arg Ala Ser Gln Ser Val Ser Ser Asn Leu Ala
            20                  25                  30

Trp Tyr Gln Gln Lys Pro Gly Gln Ala Pro Arg Leu Leu Ile Tyr Gly
        35                  40                  45

Ala Ser Thr Arg Ala Thr Gly Ile Pro Ala Arg Phe Ser Gly Ser Gly
    50                  55                  60

Ser Gly Thr Glu Phe Thr Leu Thr Ile Ser Ser Leu Gln Ser Glu Asp
65                  70                  75                  80

Phe Gly Val Tyr Tyr Cys Gln Gln Cys Asn Thr Trp Pro Leu Ala Phe
                85                  90                  95

Gly Gly Gly Thr Lys Val Glu Ile Lys
            100                 105


<210> SEQ ID NO 75
<211> LENGTH: 124
<212> TYPE: PRT
<213> ORGANISM: Homo sapiens
<220> FEATURE:
<223> OTHER INFORMATION: Heavy chain of antibody 4T0115

<400> SEQUENCE: 75

Glu Val Gln Leu Val Glu Ser Gly Gly Gly Leu Val Gln Pro Gly Arg
1               5                   10                  15

Ser Leu Arg Leu Ser Cys Val Ala Ser Gly Phe Thr Phe Asp Asn Tyr
            20                  25                  30

Ala Met His Trp Val Arg Gln Ile Pro Gly Lys Gly Leu Glu Trp Val
        35                  40                  45

Ser Thr Ile Thr Trp Asn Ser Gly Arg Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Thr Leu Arg Ala Glu Asp Thr Ala Leu Tyr Tyr Cys
                85                  90                  95

Ala Arg Glu Gly Arg Asp Gly Tyr Asn Leu Pro Tyr Tyr Ala Met Asp
            100                 105                 110

Val Trp Gly Gln Gly Thr Thr Val Thr Val Ser Ser
        115                 120


<210> SEQ ID NO 76
<211> LENGTH: 108
<212> TYPE: PRT
<213> ORGANISM: Homo sapiens
<220> FEATURE:
<223> OTHER INFORMATION: Light chain of antibody 4T0115

<400> SEQUENCE: 76

Asp Ile Gln Leu Thr Gln Ser Pro Ser Ser Leu Ser Ala Ser Ile Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Arg Phe Asn Ser Tyr Pro Ile
                85                  90                  95
```

```
Phe Thr Phe Ala Pro Gly Thr Lys Val Asp Ile Lys
            100                 105


<210> SEQ ID NO 77
<211> LENGTH: 117
<212> TYPE: PRT
<213> ORGANISM: Homo sapiens
<220> FEATURE:
<223> OTHER INFORMATION: Heavy chain of antibody 4T0154

<400> SEQUENCE: 77

Gln Val Gln Leu Val Gln Ser Gly Ala Glu Val Lys Lys Pro Gly Ser
1               5                   10                  15

Ser Val Lys Val Ser Cys Lys Thr Ser Gly Gly Asn Phe Gly Arg Phe
            20                  25                  30

Ser Ile Ser Trp Val Arg Gln Ala Pro Gly Gln Gly Leu Glu Trp Met
        35                  40                  45

Gly Arg Ile Ile Pro Thr Leu Asn Met Arg Asn Phe Ala Gln Arg Phe
    50                  55                  60

Gln Gly Arg Val Thr Ile Thr Ala Asp Lys Ser Thr Ser Thr Ala Tyr
65                  70                  75                  80

Met Glu Val Thr Ser Pro Thr Phe Glu Asp Ser Ala Val Tyr Tyr Cys
                85                  90                  95

Ala Val Glu Met Ala Thr Pro Ser Asp Thr Trp Gly Gln Gly Thr Leu
            100                 105                 110

Val Thr Val Ser Ser
        115


<210> SEQ ID NO 78
<211> LENGTH: 107
<212> TYPE: PRT
<213> ORGANISM: Homo sapiens
<220> FEATURE:
<223> OTHER INFORMATION: Light chain of antibody 4T0154

<400> SEQUENCE: 78

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Phe
            20                  25                  30

Val Ala Trp Phe Gln Gln Lys Pro Gly Lys Val Pro Lys Ser Leu Ile
        35                  40                  45

Tyr Ala Gly Ser Arg Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Ser Thr Tyr Pro Tyr
                85                  90                  95

Thr Phe Gly Gln Gly Thr Lys Leu Glu Ile Lys
            100                 105


<210> SEQ ID NO 79
<211> LENGTH: 114
<212> TYPE: PRT
<213> ORGANISM: Homo sapiens
<220> FEATURE:
<223> OTHER INFORMATION: Heavy chain of antibody 4T0159

<400> SEQUENCE: 79
```

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Thr Ser
            20                  25                  30

Ser His Tyr Trp Gly Trp Ile Arg Gln Pro Pro Gly Lys Gly Leu Glu
        35                  40                  45

Trp Val Gly Thr Arg Ser Asn Ile Gly Asn Thr Tyr Tyr Asn Pro Ser
    50                  55                  60

Leu Lys Ser Arg Val Thr Ile Phe Val Asp Thr Ser Lys Asn Gln Phe
65                  70                  75                  80

Ser Leu Arg Leu Ser Ser Val Thr Ala Ala Asp Thr Ala Val Tyr Tyr
                85                  90                  95

Cys Ala Arg Arg Phe Asp Ser Trp Gly Gln Gly Ile Leu Val Thr Val
            100                 105                 110

Ser Ser


<210> SEQ ID NO 80
<211> LENGTH: 107
<212> TYPE: PRT
<213> ORGANISM: Homo sapiens
<220> FEATURE:
<223> OTHER INFORMATION: Light chain of antibody 4T0159

<400> SEQUENCE: 80

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Phe Gln Gln Lys Pro Gly Gln Ala Pro Arg Leu Leu Ile
        35                  40                  45

Tyr Gly Ala Ser Thr Gly Val Thr Gly Ile Pro Ala Lys Phe Ser Gly
    50                  55                  60

Ser Gly Ser Gly Thr Glu Phe Thr Leu Thr Ile Gly Ser Leu Gln Ser
65                  70                  75                  80

Glu Asp Phe Ala Val Tyr Tyr Cys Gln Gln Tyr Asn Asp Trp Pro Trp
                85                  90                  95

Thr Phe Gly Gln Gly Thr Lys Val Glu Ile Lys
            100                 105


<210> SEQ ID NO 81
<211> LENGTH: 114
<212> TYPE: PRT
<213> ORGANISM: Homo sapiens
<220> FEATURE:
<223> OTHER INFORMATION: Heavy chain of antibody 4T0176

<400> SEQUENCE: 81

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Thr Ile Ser His Ser Gly Ser Thr Tyr Tyr Asn Pro Ser
    50                  55                  60

Leu Gln Ser Arg Val Thr Met Ser Val Asp Thr Ser Lys Asn His Phe
65                  70                  75                  80
```

```
Ser Leu Arg Leu Ser Ser Val Thr Ala Ala Asp Thr Ala Val Tyr Tyr
                85                  90                  95

Cys Val Arg Arg Phe Asp Tyr Trp Gly Gln Gly Thr Leu Val Thr Val
            100                 105                 110

Ser Ser


<210> SEQ ID NO 82
<211> LENGTH: 107
<212> TYPE: PRT
<213> ORGANISM: Homo sapiens
<220> FEATURE:
<223> OTHER INFORMATION: Light chain of antibody 4T0176

<400> SEQUENCE: 82

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Thr Ser Asn
            20                  25                  30

Leu Ala Trp Phe Gln Gln Gln Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Leu Ala Val Tyr Tyr Cys Gln Gln Tyr Asn Lys Trp Pro Trp
                85                  90                  95

Thr Phe Gly Gln Gly Thr Lys Val Glu Ile Lys
            100                 105


<210> SEQ ID NO 83
<211> LENGTH: 127
<212> TYPE: PRT
<213> ORGANISM: Homo sapiens
<220> FEATURE:
<223> OTHER INFORMATION: Heavy chain of antibody 4T0182

<400> SEQUENCE: 83

Gln Val Gln Leu Val Gln Ser Gly Ala Glu Val Lys Lys Pro Gly Ala
1               5                   10                  15

Ser Ile Lys Val Ser Cys Lys Ala Ser Gly Tyr Ile Phe Thr Asp Tyr
            20                  25                  30

Tyr Met His Trp Val Arg Gln Ala Pro Gly Gln Gly Leu Glu Trp Met
        35                  40                  45

Gly Trp Leu Asn Pro Lys Ser Gly Gly Thr Asn Tyr Ala Gln Lys Phe
    50                  55                  60

Gln Gly Arg Val Thr Met Thr Arg Asp Thr Ser Ile Asn Thr Ala Tyr
65                  70                  75                  80

Met Glu Leu Asn Ser Val Arg Ser Asp Asp Thr Ala Val Tyr Tyr Cys
                85                  90                  95

Ala Ala Pro Gly Glu Thr Ile Val Arg Gly Val Ile Tyr His Tyr Tyr
            100                 105                 110

Gly Met Gly Val Trp Gly Gln Gly Thr Ala Val Thr Val Ser Ser
        115                 120                 125


<210> SEQ ID NO 84
<211> LENGTH: 111
<212> TYPE: PRT
<213> ORGANISM: Homo sapiens
<220> FEATURE:
```

<223> OTHER INFORMATION: Light chain of antibody 4T0182

<400> SEQUENCE: 84

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Arg
20 25 30

Asn Gly Tyr Asn Tyr Leu Asp Trp Tyr Leu Gln Lys Pro Gly Gln Ser
35 40 45

Pro Gln Leu Leu Ile Tyr Met Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Ala
85 90 95

Leu Gln Thr Pro Thr Phe Gly Gln Gly Thr Lys Leu Glu Ile Lys
100 105 110

<210> SEQ ID NO 85
<211> LENGTH: 125
<212> TYPE: PRT
<213> ORGANISM: Homo sapiens
<220> FEATURE:
<223> OTHER INFORMATION: Heavy chain of antibody 4T0243

<400> SEQUENCE: 85

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Leu Ser Thr Tyr
20 25 30

Tyr Trp Asn Trp Ile Arg Gln Pro Pro Gly Lys Gly Leu Glu Trp Ile
35 40 45

Gly Tyr Ile Tyr Tyr Ser Ser Leu Pro Lys Tyr Ser Pro Thr Leu Lys
50 55 60

Ser Arg Ile Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Ala Pro Arg Gly Tyr Ser Ser Gly Lys Tyr Asn Tyr Tyr Gly Leu
100 105 110

Asp Val Trp Ser Gln Gly Thr Thr Val Thr Val Ser Ser
115 120 125

<210> SEQ ID NO 86
<211> LENGTH: 108
<212> TYPE: PRT
<213> ORGANISM: Homo sapiens
<220> FEATURE:
<223> OTHER INFORMATION: Light chain of antibody 4T0243

<400> SEQUENCE: 86

Ser Tyr Glu Leu Thr Gln Pro Pro Ser Val Ser Val Ser Pro Gly His
1 5 10 15

Thr Ala Thr Ile Thr Cys Ser Gly Asp Ala Leu Ser Lys Gln Phe Ala
20 25 30

Tyr Trp Tyr Gln Gln Lys Pro Gly Gln Ala Pro Val Leu Val Ile Ser
35 40 45

Lys Asp Thr Glu Arg Pro Ser Gly Ile Pro Gly Arg Phe Ser Gly Ser

```
    50                  55                  60

Ser Ser Gly Pro Thr Ala Thr Leu Thr Ile Ser Gly Val Gln Ala Glu
65                  70                  75                  80

Asp Glu Ala Asp Tyr Tyr Cys Gln Ser Ala Asp Ser Ser Gly Gly Tyr
                85                  90                  95

Tyr Val Phe Gly Ser Gly Thr Arg Val Thr Val Leu
            100                 105


<210> SEQ ID NO 87
<211> LENGTH: 121
<212> TYPE: PRT
<213> ORGANISM: Homo sapiens
<220> FEATURE:
<223> OTHER INFORMATION: Heavy chain of antibody 4T0262

<400> SEQUENCE: 87

Gln Val Gln Leu Val Gln Ser Gly Ala Glu Val Lys Lys Pro Gly Ala
1               5                   10                  15

Ser Val Lys Ile Ala Cys Lys Ala Ser Gly Tyr Thr Phe Arg Asn Tyr
            20                  25                  30

Tyr Met Asn Trp Val Arg Gln Ala Pro Gly Lys Gly Leu Glu Trp Val
        35                  40                  45

Gly Ile Ile Ser Pro Arg Gly Gly Thr Thr Arg Tyr Ala Pro Lys Phe
    50                  55                  60

Gln Gly Arg Val Thr Met Thr Ser Asp Thr Ser Thr Thr Thr Val Phe
65                  70                  75                  80

Met Glu Leu Asn Ser Leu Arg Ser Glu Asp Thr Ala Met Tyr Tyr Cys
                85                  90                  95

Ala Arg Gly Ile Thr Met Ile Arg Asp Gly Trp Phe Asp His Trp Gly
            100                 105                 110

Gln Gly Thr Leu Val Thr Val Ser Ser
        115                 120


<210> SEQ ID NO 88
<211> LENGTH: 108
<212> TYPE: PRT
<213> ORGANISM: Homo sapiens
<220> FEATURE:
<223> OTHER INFORMATION: Light chain of antibody 4T0262

<400> SEQUENCE: 88

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Asn Trp
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Ser Gly Val Pro Ser Arg Phe Ser Gly
    50                  55                  60

Ser Gly Ser Gly Thr Asp Phe Thr Leu Ile Ile Lys Ser Leu Gln Pro
65                  70                  75                  80

Asp Asp Phe Gly Ser Tyr Phe Cys Leu Gln Tyr Ser Ser Ser Ser Pro
                85                  90                  95

Tyr Ser Phe Gly Gln Gly Thr Lys Leu Glu Ile Lys
            100                 105


<210> SEQ ID NO 89
<211> LENGTH: 122
```

<212> TYPE: PRT
<213> ORGANISM: Homo sapiens
<220> FEATURE:
<223> OTHER INFORMATION: Heavy chain of antibody 4T0284

<400> SEQUENCE: 89

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
            20                  25                  30

Gly Ile Ser Trp Leu Arg Gln Ala Pro Gly Gln Gly Leu Glu Trp Met
        35                  40                  45

Gly Trp Ile Ser Thr Tyr Asn Gly Asp Thr Asn Tyr Ala Gln Lys Val
    50                  55                  60

Gln Gly Arg Val Thr Met Thr Thr Asp Thr Ser Ser Thr Thr Ala Tyr
65                  70                  75                  80

Met Glu Leu Arg Ser Leu Arg Ser Asp Asp Thr Ala Val Tyr Phe Cys
                85                  90                  95

Ala Arg Gly Ile Thr Met Val Arg Gly Leu Asp Trp Phe Asp Pro Trp
            100                 105                 110

Gly Gln Gly Thr Leu Val Thr Val Ser Ser
        115                 120
```

<210> SEQ ID NO 90
<211> LENGTH: 107
<212> TYPE: PRT
<213> ORGANISM: Homo sapiens
<220> FEATURE:
<223> OTHER INFORMATION: Light chain of antibody 4T0284

<400> SEQUENCE: 90

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Asn Ile Ser Ser Asn
            20                  25                  30

Leu Ala Trp Tyr Gln Gln Lys Pro Gly Arg Ala Pro Arg Leu Leu Ile
        35                  40                  45

Asp Gly Ala Ser Thr Arg Ala Thr Gly Ile Pro Ala Arg Phe Ser Gly
    50                  55                  60

Ser Gly Ser Gly Thr Glu Phe Thr Leu Ser Ile Ser Ser Leu Gln Ser
65                  70                  75                  80

Glu Asp Ser Thr Val Tyr Tyr Cys Gln Gln Tyr Lys Asn Trp Pro Leu
                85                  90                  95

Thr Phe Gly Gly Gly Thr Lys Val Glu Ile Lys
            100                 105
```

<210> SEQ ID NO 91
<211> LENGTH: 129
<212> TYPE: PRT
<213> ORGANISM: Homo sapiens
<220> FEATURE:
<223> OTHER INFORMATION: Heavy chain of antibody 4T0306

<400> SEQUENCE: 91

```
Gln Val Gln Leu Gln Gln Ser Gly Pro Gly Leu Val Arg Pro Ser Gln
1               5                   10                  15

Thr Leu Ser Leu Ile Cys Ala Ile Ser Gly Asp Ser Val Ser Asp Asn
            20                  25                  30

Asn Ala Ala Trp Asn Trp Ile Arg Gln Ser Pro Ser Arg Gly Leu Glu
```

```
        35                  40                  45

Trp Leu Gly Arg Thr Tyr Phe Arg Ser Arg Trp Tyr Asn Asp Tyr Pro
    50                  55                  60

Glu Ser Leu Lys Gly Arg Val Ile Ile Asn Pro Asp Thr Ala Glu Asn
65                  70                  75                  80

Gln Val Ser Leu Gln Leu Ser Ser Val Thr Pro Gly Asp Thr Ala Val
                85                  90                  95

Tyr Tyr Cys Val Arg Glu Tyr Tyr Asp Leu Trp Asn Gly Phe Tyr Pro
            100                 105                 110

Gly Gly Ala Met Asp Val Trp Gly Gln Gly Thr Thr Val Thr Val Ser
        115                 120                 125

Ser


<210> SEQ ID NO 92
<211> LENGTH: 107
<212> TYPE: PRT
<213> ORGANISM: Homo sapiens
<220> FEATURE:
<223> OTHER INFORMATION: Light chain of antibody 4T0306

<400> SEQUENCE: 92

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Asp Phe
            20                  25                  30

Leu Asn Trp Phe Gln Gln Lys Pro Gly Lys Ala Pro Lys Leu Leu Ile
        35                  40                  45

Tyr Asp Val Ser Lys Leu Ala Arg Gly Val Pro Ser Arg Phe Ser Gly
    50                  55                  60

Ser Ala Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asp Leu Pro Arg
                85                  90                  95

Thr Phe Gly Gln Gly Thr Lys Leu Glu Ile Lys
            100                 105


<210> SEQ ID NO 93
<211> LENGTH: 125
<212> TYPE: PRT
<213> ORGANISM: Homo sapiens
<220> FEATURE:
<223> OTHER INFORMATION: Heavy chain of antibody 4T0344

<400> SEQUENCE: 93

Glu Val Gln Leu Leu Glu Ser Gly Gly Gly Leu Val Gln Pro Gly Gly
1               5                   10                  15

Ser Leu Arg Leu Ser Cys Ala Thr Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ser Ile Gly Asp Thr Gly Gly Ser Lys Tyr Tyr Val Asp Pro Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Gly Ser Trp Pro Arg Thr Thr Val Leu Ser Thr Tyr Tyr Phe
```

100 105 110

Asp Tyr Trp Gly Gln Gly Thr Leu Val Thr Val Ser Ser
115 120 125

<210> SEQ ID NO 94
<211> LENGTH: 107
<212> TYPE: PRT
<213> ORGANISM: Homo sapiens
<220> FEATURE:
<223> OTHER INFORMATION: Light chain of antibody 4T0344

<400> SEQUENCE: 94

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Ser Asn Tyr
20 25 30

Leu Ala Trp Tyr Gln Gln Lys Pro Gly Gln Ser Pro Lys Leu Leu Ile
35 40 45

Tyr Ala Ala Ser Thr Leu Gln Phe Gly Val Pro Thr Arg Phe Ser Gly
50 55 60

Ser Gly Ser Gly Ala Asp Phe Thr Leu Thr Ile Ser Ser Leu Gln Pro
65 70 75 80

Glu Asp Val Ala Thr Tyr Tyr Cys Gln Lys Tyr Asn Gly Ala Pro Trp
85 90 95

Arg Phe Gly Gln Gly Thr Lys Val Glu Ile Lys
100 105

<210> SEQ ID NO 95
<211> LENGTH: 122
<212> TYPE: PRT
<213> ORGANISM: Homo sapiens
<220> FEATURE:
<223> OTHER INFORMATION: Heavy chain of antibody 4T0365

<400> SEQUENCE: 95

Gln Leu Gln Leu Gln Glu Ser Gly Pro Gly Leu Val Lys Ser Ser Glu
1 5 10 15

Thr Leu Ser Leu Thr Cys Thr Val Ser Gly Asp Ser Ile Arg Ser Asp
20 25 30

Ser His Tyr Trp Asp Trp Ile Arg Gln Pro Pro Gly Lys Gly Leu Glu
35 40 45

Trp Ile Gly Asn Ile Tyr Tyr Ser Gly Ser Thr Tyr Tyr Asn Pro Ser
50 55 60

Leu Lys Ser Arg Val Thr Ile Ser Ile Asp Thr Ser Lys Ser Gln Phe
65 70 75 80

Ser Leu Arg Leu Ser Ser Val Thr Ala Ala Asp Thr Ala Leu Tyr Tyr
85 90 95

Cys Ala Thr Ser Ser Arg Gly Ser Val Ser Tyr Tyr Ser Arg Tyr Trp
100 105 110

Gly Gln Gly Thr Leu Val Thr Val Ser Ser
115 120

<210> SEQ ID NO 96
<211> LENGTH: 110
<212> TYPE: PRT
<213> ORGANISM: Homo sapiens
<220> FEATURE:
<223> OTHER INFORMATION: Light chain of antibody 4T0365

<400> SEQUENCE: 96

Gln Ser Val Leu Thr Gln Pro Pro Ser Val Ser Ala Ala Pro Gly Gln
1 5 10 15

Lys Val Thr Ile Ser Cys Ser Gly Ser Ser Ser Asn Ile Gly Leu Asn
20 25 30

Tyr Val Ser Trp Tyr Gln Gln Phe Pro Gly Thr Ala Pro Lys Leu Leu
35 40 45

Ile Tyr Asp Asn Ile Gln Arg Pro Ser Gly Ile Pro Asp Arg Ile Ser
50 55 60

Gly Ser Lys Ser Gly Thr Ser Ser Thr Leu Ala Ile Thr Gly Leu Gln
65 70 75 80

Thr Gly Asp Glu Ala Asp Tyr Phe Cys Ser Val Trp Asp Ser Ser Leu
85 90 95

Gly Ser Arg Val Phe Gly Gly Gly Thr Lys Leu Thr Val Leu
100 105 110

<210> SEQ ID NO 97
<211> LENGTH: 126
<212> TYPE: PRT
<213> ORGANISM: Homo sapiens
<220> FEATURE:
<223> OTHER INFORMATION: Heavy chain of antibody 4T0412

<400> SEQUENCE: 97

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Arg Phe
20 25 30

Gly Leu His Trp Val Arg Gln Val Pro Asp Lys Gly Leu Glu Trp Val
35 40 45

Ala Leu Ile Trp Tyr Asp Gly Asn Asp Arg Tyr Tyr Ala Asp Ser Val
50 55 60

Lys Gly Arg Phe Thr Val Ser Arg Asp Asn Ser Lys Asn Thr Leu Phe
65 70 75 80

Leu Glu Met Asn Ser Leu Arg Ala Glu Asp Thr Ala Val Tyr Tyr Cys
85 90 95

Val Arg Glu Thr Phe Gln Pro Gly Gly Glu Val Pro Pro Leu Trp Tyr
100 105 110

Phe Asp Val Trp Gly Arg Gly Thr Leu Val Thr Val Ser Ser
115 120 125

<210> SEQ ID NO 98
<211> LENGTH: 107
<212> TYPE: PRT
<213> ORGANISM: Homo sapiens
<220> FEATURE:
<223> OTHER INFORMATION: Light chain of antibody 4T0412

<400> SEQUENCE: 98

Asp Ile Gln Leu Thr Gln Ser Pro Ser Ser Leu Ser Ala Ser Val Gly
1 5 10 15

Asp Arg Val Thr Ile Thr Cys Arg Ala Ser Gln Ser Ile Thr Thr Asn
20 25 30

Leu Asn Trp Tyr Gln Gln Lys Pro Gly Lys Ala Pro Asn Leu Leu Ile
35 40 45

Phe Ala Ala Ser Ser Leu Gln Ser Gly Val Pro Ser Arg Phe Ser Gly
50 55 60

Ser Gly Ser Gly Thr Asp Phe Thr Leu Thr Ile Thr Ser Leu Gln Pro

```
65                  70                  75                  80

Glu Asp Phe Ala Thr Tyr Tyr Cys Gln Gln Ser Tyr Gly Thr Pro Arg
                85                  90                  95

Thr Phe Gly Gln Gly Thr Lys Val Glu Ile Lys
            100                 105


<210> SEQ ID NO 99
<211> LENGTH: 123
<212> TYPE: PRT
<213> ORGANISM: Homo sapiens
<220> FEATURE:
<223> OTHER INFORMATION: Heavy chain of antibody 4T0423

<400> SEQUENCE: 99

Glu Val Gln Leu Val Glu Ser Gly Gly Gly Trp Val Gln Pro Gly Arg
1               5                   10                  15

Ser Leu Arg Leu Ser Cys Val Ala Ser Gly Phe Thr Phe Gln Asn Tyr
            20                  25                  30

Ala Met His Trp Val Arg Gln Pro Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Arg Asn Ser Leu Tyr
65                  70                  75                  80

Leu Gln Met Arg Ser Leu Arg Pro Asp Asp Thr Ala Leu Tyr Tyr Cys
                85                  90                  95

Ala Lys Glu Asn Arg Ile Glu Leu Leu Pro Gly Trp Gly Met Asp Val
            100                 105                 110

Trp Gly Gln Gly Thr Thr Val Thr Val Ser Ser
        115                 120


<210> SEQ ID NO 100
<211> LENGTH: 112
<212> TYPE: PRT
<213> ORGANISM: Homo sapiens
<220> FEATURE:
<223> OTHER INFORMATION: Light chain of antibody 4T0423

<400> SEQUENCE: 100

Gln Ser Ala Leu Thr Gln Pro Ala Ser Val Ser Gly Ser Pro Gly Gln
1               5                   10                  15

Ser Ile Thr Ile Ser Cys Thr Gly Pro Ser Ser Asp Val Trp Ser Tyr
            20                  25                  30

Asn Leu Val Ser Trp Tyr Gln Gln Phe Pro Gly Lys Ala Pro Lys Leu
        35                  40                  45

Met Ile Tyr Glu Asp Thr Lys Arg Pro Ser Gly Val Ser Ile Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Phe Cys Cys Ser Tyr Ala Gly Thr
                85                  90                  95

Ser Ala Phe Val Trp Val Phe Gly Gly Gly Thr Lys Leu Thr Val Leu
            100                 105                 110


<210> SEQ ID NO 101
<211> LENGTH: 121
<212> TYPE: PRT
<213> ORGANISM: Homo sapiens
<220> FEATURE:
```

<223> OTHER INFORMATION: Heavy chain of antibody 4T0427

<400> SEQUENCE: 101

Glu Val Gln Leu Val Glu Ser Gly Gly Asp Leu Ile Gln Pro Gly Gly
1 5 10 15

Ser Leu Arg Leu Ser Cys Ala Ala Ser Gly Phe Phe Val Ser Ser Ser
20 25 30

Tyr Met Ser Trp Val Arg Gln Ala Pro Gly Lys Gly Leu Glu Trp Val
35 40 45

Ser Ala Ile Tyr Ser Gly Gly Thr Thr Phe Tyr Val Asp Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Asp Glu Glu Trp Leu Phe Ser Gly Tyr Gly Met Asp Val Trp Gly
100 105 110

Gln Gly Thr Thr Val Thr Val Ser Ser
115 120

<210> SEQ ID NO 102
<211> LENGTH: 110
<212> TYPE: PRT
<213> ORGANISM: Homo sapiens
<220> FEATURE:
<223> OTHER INFORMATION: Light chain of antibody 4T0427

<400> SEQUENCE: 102

Gln Ser Val Leu Thr Gln Pro Pro Ser Thr Ser Gly Thr Pro Gly Gln
1 5 10 15

Arg Val Thr Ile Ser Cys Ser Gly Ser Ser Ser Asn Ile Gly Leu Asn
20 25 30

Tyr Val Tyr Trp Tyr Gln Gln Leu Pro Gly Thr Ala Pro Lys Leu Leu
35 40 45

Ile Tyr Arg Asn Asn Gln Arg Pro Ser Gly Val Pro Asp Arg Phe Ser
50 55 60

Gly Ser Lys Ser Gly Thr Ser Ala Ser Leu Ala Ile Ser Gly Leu Arg
65 70 75 80

Ser Glu Asp Glu Ala Asp Tyr Tyr Cys Ala Ala Trp Asp Asp Ser Leu
85 90 95

Ser Ala Tyr Ile Phe Gly Thr Gly Thr Lys Val Thr Val Leu
100 105 110

<210> SEQ ID NO 103
<211> LENGTH: 116
<212> TYPE: PRT
<213> ORGANISM: Homo sapiens
<220> FEATURE:
<223> OTHER INFORMATION: Heavy chain of antibody 4T0429

<400> SEQUENCE: 103

Gln Val Gln Leu Gln Gln Trp Gly Ala Gly Leu Leu Lys Pro Ser Glu
1 5 10 15

Thr Leu Ser Leu Thr Cys Ala Val Tyr Arg Gly Ser Phe Ile Thr Tyr
20 25 30

Tyr Trp Ser Trp Val Arg Gln Pro Pro Gly Arg Gly Leu Glu Trp Ile
35 40 45

Gly Glu Ile Tyr Lys Asp Gly Ser Ala Ser Tyr Asn Pro Ser Leu Lys

```
    50                  55                  60

Asn Arg Val Thr Ile Ser Leu Asp Met Ser Lys Asn His Phe Ser Leu
65                  70                  75                  80

Asn Leu Asp Ser Val Thr Ala Ala Asp Thr Ala Val Tyr Tyr Cys Ala
                85                  90                  95

Arg His Gly His Thr Gly Met Asp Val Trp Gly Gln Gly Thr Thr Val
            100                 105                 110

Thr Val Ser Ser
        115


<210> SEQ ID NO 104
<211> LENGTH: 110
<212> TYPE: PRT
<213> ORGANISM: Homo sapiens
<220> FEATURE:
<223> OTHER INFORMATION: Light chain of antibody 4T0429

<400> SEQUENCE: 104

Gln Ser Val Leu Thr Gln Pro Pro Ser Thr Ser Gly Thr Pro Gly Gln
1               5                   10                  15

Arg Val Thr Ile Ser Cys Ser Gly Ser Ser Ser Asn Ile Gly Leu Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Ala Tyr Ile Phe Gly Thr Gly Thr Lys Val Thr Val Leu
            100                 105                 110


<210> SEQ ID NO 105
<211> LENGTH: 121
<212> TYPE: PRT
<213> ORGANISM: Homo sapiens
<220> FEATURE:
<223> OTHER INFORMATION: Heavy chain of antibody 4T0434

<400> SEQUENCE: 105

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Leu Arg Asn Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Thr Thr Asn Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Arg Ser Leu Thr Ala Glu Asp Thr Ala Val Tyr Tyr Cys
                85                  90                  95

Ala Arg Asp Val Gly Leu Tyr Asn Thr Gly Trp Ile Asp Tyr Trp Gly
            100                 105                 110

Gln Gly Ala Pro Val Thr Val Ser Ser
        115                 120
```

<210> SEQ ID NO 106
<211> LENGTH: 113
<212> TYPE: PRT
<213> ORGANISM: Homo sapiens
<220> FEATURE:
<223> OTHER INFORMATION: Light chain of antibody 4T0434

<400> SEQUENCE: 106

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Val Leu His Ser
20 25 30

Ser Asn Asn Lys Tyr Tyr Leu Ala Trp Tyr Gln Gln Lys Pro Gly Gln
35 40 45

Pro Pro Lys Leu Leu Ile Tyr Trp Ala Ser Thr Arg Gly Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Gln
85 90 95

Phe Tyr Ser Thr Pro Leu Thr Phe Gly Gly Gly Thr Lys Val Glu Ile
100 105 110

Lys

<210> SEQ ID NO 107
<211> LENGTH: 118
<212> TYPE: PRT
<213> ORGANISM: Homo sapiens
<220> FEATURE:
<223> OTHER INFORMATION: Heavy chain of antibody 4T0444

<400> SEQUENCE: 107

Glu Val Gln Leu Val Val Ser Gly Gly Gly Leu Val Gln Pro Gly Gly
1 5 10 15

Ser Leu Arg Leu Ser Cys Ala Ala Ser Gly Phe Thr Leu Lys Ser Tyr
20 25 30

Asp Ile His Trp Val Arg Gln Arg Pro Gly Glu Gly Leu Glu Trp Val
35 40 45

Ala Ala Ile Gly Ala Ala Gly Asp Thr Tyr Phe Ser Gly Ser Val Lys
50 55 60

Gly Arg Phe Thr Ile Ser Arg Glu Asn Ala Arg Asn Ser Leu Tyr Leu
65 70 75 80

Gln Met Asn Ser Leu Gly Ala Gly Asp Thr Ala Ile Tyr Tyr Cys Ala
85 90 95

Arg Ala Arg Phe Gly Asp Leu Ala Leu Asp Tyr Trp Gly Gln Gly Ile
100 105 110

Leu Val Thr Val Ser Ser
115

<210> SEQ ID NO 108
<211> LENGTH: 108
<212> TYPE: PRT
<213> ORGANISM: Homo sapiens
<220> FEATURE:
<223> OTHER INFORMATION: Light chain of antibody 4T0444

<400> SEQUENCE: 108

Glu Ile Val Leu Thr Gln Ser Pro Gly Thr Leu Ser Leu Ser Pro Gly
1 5 10 15

```
Glu Arg Ala Thr Leu Ser Cys Arg Ser Ser Gln Ser Val Ser Ser Asn
            20                  25                  30

Ser Leu Ala Trp Tyr Gln Gln Lys Pro Gly Gln Ala Pro Arg Leu Leu
        35                  40                  45

Ile Tyr Gly Ala Ser Ser Arg Ala Ala Gly Ile Pro Asp Arg Phe Ser
    50                  55                  60

Gly Ser Gly Ser Gly Thr Asp Phe Thr Leu Thr Ile Ser Arg Leu Gln
65                  70                  75                  80

Pro Glu Asp Phe Ala Val Phe Phe Cys His Gln Tyr Ser Ser Ser Pro
                85                  90                  95

Leu Thr Phe Gly Gly Gly Thr Lys Val Glu Ile Lys
            100                 105


<210> SEQ ID NO 109
<211> LENGTH: 119
<212> TYPE: PRT
<213> ORGANISM: Homo sapiens
<220> FEATURE:
<223> OTHER INFORMATION: Heavy chain of antibody 4T0452

<400> SEQUENCE: 109

Glu Val Gln Leu Val Glu Ser Gly Gly Gly Leu Val Lys Pro Gly Gly
1               5                   10                  15

Ser Leu Arg Ile Ser Cys Ala Ala Ser Gly Phe Ser Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Ser Val Ser Asp Gly Gly Pro Ile His Tyr Ala Ala
    50                  55                  60

Pro Val Lys Gly Arg Phe Thr Ile Ser Arg Asp Asp Ser Lys Lys Met
65                  70                  75                  80

Leu Tyr Leu Gln Met Asn Ser Leu Lys Val Asp Asp Thr Ala Val Tyr
                85                  90                  95

Tyr Cys Ala Thr Glu Pro Arg Gly Tyr Asp Trp Gly Trp Gly Gln Gly
            100                 105                 110

Thr Leu Val Thr Val Ser Ser
        115


<210> SEQ ID NO 110
<211> LENGTH: 112
<212> TYPE: PRT
<213> ORGANISM: Homo sapiens
<220> FEATURE:
<223> OTHER INFORMATION: Light chain of antibody 4T0452

<400> SEQUENCE: 110

Gln Ser Val Leu Thr Gln Pro Pro Ser Val Ser Gly Ala Pro Gly Gln
1               5                   10                  15

Arg Val Thr Ile Ser Cys Thr Gly Ser Tyr Ser Asn Ile Gly Ala Gly
            20                  25                  30

Tyr Asp Val Tyr Trp Tyr Gln Gln Phe Pro Gly Thr Ala Pro Lys Leu
        35                  40                  45

Leu Ile Tyr Gly Asn Thr Asn Arg Pro Ser Gly Val Pro Asp Arg Phe
    50                  55                  60

Ser Gly Ser Arg Ser Gly Thr Ser Ala Ser Leu Ala Ile Thr Gly Leu
65                  70                  75                  80

Gln Ala Glu Asp Glu Ala His Tyr Tyr Cys Gln Ser Tyr Asp Ser Arg
```

```
                85                  90                  95

Leu Arg Asp Asn Trp Val Leu Gly Gly Gly Thr Lys Leu Thr Val Leu
            100                 105                 110


<210> SEQ ID NO 111
<211> LENGTH: 117
<212> TYPE: PRT
<213> ORGANISM: Homo sapiens
<220> FEATURE:
<223> OTHER INFORMATION: Heavy chain of antibody 4T0525

<400> SEQUENCE: 111

Gln Val Gln Leu Val Gln Ser Gly Pro Glu Val Lys Lys Pro Gly Ser
1               5                   10                  15

Ser Val Lys Val Ser Cys Lys Ala Ser Gly Gly Arg Phe Ser Thr Ser
            20                  25                  30

Thr Phe Asn Trp Val Arg Gln Ala Pro Gly Gln Gly Leu Glu Trp Met
        35                  40                  45

Gly Arg Ile Ile Pro Ile Ile Ala Thr Thr Asp Tyr Ala Gln Lys Phe
    50                  55                  60

Gln Gly Arg Val Thr Ile Thr Ala Asp Lys Ser Thr Gly Thr Ala Tyr
65                  70                  75                  80

Met Glu Leu Ser Arg Leu Arg Ser Asp Asp Thr Ala Val Tyr Tyr Cys
                85                  90                  95

Ala Gly Gly Gly Thr Gly Leu Phe Asp Ser Trp Gly Gln Gly Thr Leu
            100                 105                 110

Val Thr Val Ser Ser
        115


<210> SEQ ID NO 112
<211> LENGTH: 107
<212> TYPE: PRT
<213> ORGANISM: Homo sapiens
<220> FEATURE:
<223> OTHER INFORMATION: Light chain of antibody 4T0525

<400> SEQUENCE: 112

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Glu Ala Pro Lys Ser Leu Ile
        35                  40                  45

Tyr Glu Ala Ser Ser Leu Gln Ser Gly Val Pro Ser Lys Phe Ser Gly
    50                  55                  60

Ser Gly Ser Gly Thr Asp Phe Ser Leu Thr Ile Ser Ser Leu Gln Pro
65                  70                  75                  80

Glu Asp Phe Ala Thr Tyr Tyr Cys Gln Gln Tyr Asn Thr Leu Pro Phe
                85                  90                  95

Thr Phe Gly Gly Gly Thr Lys Val Glu Ile Lys
            100                 105


<210> SEQ ID NO 113
<211> LENGTH: 123
<212> TYPE: PRT
<213> ORGANISM: Homo sapiens
<220> FEATURE:
<223> OTHER INFORMATION: Heavy chain of antibody 4T0541

<400> SEQUENCE: 113
```

```
Glu Val Gln Leu Leu Glu Ser Gly Gly Gly Leu Glu Glu Pro Gly Gly
1               5                   10                  15

Ser Leu Arg Leu Ser Cys Thr Val Ser Gly Phe Ser Phe Ser Met Tyr
            20                  25                  30

Thr Met Thr Trp Val Arg Gln Val Pro Gly Lys Gly Leu Glu Trp Val
        35                  40                  45

Ser Ala Val Ser Gly Thr Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Ser Asp Tyr Leu Trp Gly Ser His Arg Tyr Phe Asp Tyr
            100                 105                 110

Trp Gly Gln Gly Thr Leu Val Thr Val Ser Ser
        115                 120


<210> SEQ ID NO 114
<211> LENGTH: 107
<212> TYPE: PRT
<213> ORGANISM: Homo sapiens
<220> FEATURE:
<223> OTHER INFORMATION: Light chain of antibody 4T0541

<400> SEQUENCE: 114

Asp Ile Gln Met Thr Gln Ser Pro Ser Thr Leu Ser Ala Ser Val Gly
1               5                   10                  15

Asp Arg Val Thr Val Thr Cys Arg Ala Ser His Ser Val Ser Gly Arg
            20                  25                  30

Leu Ala Trp Tyr Gln Gln Lys Pro Gly Lys Ala Pro Lys Leu Leu Ile
        35                  40                  45

Ser Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Phe Cys Gln Gln Tyr Asn Ser Tyr Ser Pro
                85                  90                  95

Thr Phe Gly Gln Gly Thr Lys Val Glu Ile Lys
            100                 105


<210> SEQ ID NO 115
<211> LENGTH: 124
<212> TYPE: PRT
<213> ORGANISM: Homo sapiens
<220> FEATURE:
<223> OTHER INFORMATION: Heavy chain of antibody 4T0570

<400> SEQUENCE: 115

Gln Val Gln Leu Val Gln Ser Gly Ala Glu Val Lys Lys Pro Gly Ala
1               5                   10                  15

Ser Ile Lys Val Ser Cys Lys Ala Ser Gly Tyr Thr Phe Val Ser Lys
            20                  25                  30

Tyr Ile His Trp Val Arg Gln Ala Pro Gly Gln Gly Leu Glu Trp Met
        35                  40                  45

Gly Ile Ile Asn Pro Ser Gly Gly Arg Thr Asp Tyr Ala Gln Lys Phe
    50                  55                  60

Gln Gly Arg Val Thr Ile Ser Arg Asp Thr Ser Thr Ser Thr Val Tyr
```

```
65                  70                  75                  80

Met Glu Leu Ser Ser Leu Arg Ser Glu Asp Thr Ala Phe Tyr Tyr Cys
                85                  90                  95

Ala Arg Ala Leu Pro Phe Arg Val Thr Gly Ala Arg Asp Val Phe Asp
            100                 105                 110

Ile Trp Gly Gln Gly Thr Met Val Thr Val Ser Ser
        115                 120


<210> SEQ ID NO 116
<211> LENGTH: 107
<212> TYPE: PRT
<213> ORGANISM: Homo sapiens
<220> FEATURE:
<223> OTHER INFORMATION: Light chain of antibody 4T0570

<400> SEQUENCE: 116

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Thr Asn
            20                  25                  30

Leu Ala Trp Phe Gln Gln Arg Pro Gly Lys Ala Pro Lys Ser Leu Val
        35                  40                  45

Tyr Ala Ala Ser Thr Leu Gln Asn Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Thr Tyr Pro Leu
                85                  90                  95

Thr Phe Gly Gly Gly Thr Lys Val Glu Ile Lys
            100                 105


<210> SEQ ID NO 117
<211> LENGTH: 118
<212> TYPE: PRT
<213> ORGANISM: Homo sapiens
<220> FEATURE:
<223> OTHER INFORMATION: Heavy chain of antibody 4T0578

<400> SEQUENCE: 117

Glu Val Gln Leu Val Glu Ser Gly Gly Ala Leu Val Gln Pro Gly Gly
1               5                   10                  15

Ser Leu Arg Leu Ser Cys Ala Ala Ser Gly Phe Thr Phe Ser Arg Tyr
            20                  25                  30

Asp Ile His Trp Val Arg Gln Ala Ser Gly Lys Gly Leu Glu Trp Val
        35                  40                  45

Ser Ala Ile Gly Lys Ala Gly Asp Ala Tyr Tyr Ala Gly Ser Val Arg
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Ala Ser Phe Gly Asp Leu Tyr Phe Asp Leu Trp Gly Arg Gly Thr
            100                 105                 110

Leu Val Thr Val Ser Ser
        115


<210> SEQ ID NO 118
<211> LENGTH: 113
```

<212> TYPE: PRT
<213> ORGANISM: Homo sapiens
<220> FEATURE:
<223> OTHER INFORMATION: Light chain of antibody 4T0578

<400> SEQUENCE: 118

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu His Ser
            20                  25                  30

Ser Asn Asn Lys Asn Ser Val Ala Trp Tyr Gln Gln Lys Pro Gly Gln
        35                  40                  45

Pro Pro Lys Leu Leu Ile Tyr Trp Ala Ser Thr Arg Glu Phe Gly Val
    50                  55                  60

Pro Asp Arg Phe Ser Gly Ser Gly Ser Gly Thr Asp Phe Ala Leu Thr
65                  70                  75                  80

Ile Ser Ser Leu Gln Ala Glu Asp Val Ala Val Tyr Val Cys Gln Gln
                85                  90                  95

Tyr Tyr Asn Ser Pro Leu Thr Phe Gly Pro Gly Thr Lys Val Asp Ile
            100                 105                 110

Lys
```

<210> SEQ ID NO 119
<211> LENGTH: 121
<212> TYPE: PRT
<213> ORGANISM: Homo sapiens
<220> FEATURE:
<223> OTHER INFORMATION: Heavy chain of antibody 4T0657

<400> SEQUENCE: 119

```
Glu Val Gln Leu Leu Glu Ser Gly Gly Asp Leu Val Gln Pro Gly Gly
1               5                   10                  15

Ser Leu Arg Leu Ser Cys Thr Ala Ser Gly Phe Thr Phe Lys Asp Phe
            20                  25                  30

Ala Met Asn Trp Val Arg Gln Ala Pro Gly Lys Gly Leu Glu Trp Val
        35                  40                  45

Ser Gly Ile Thr Gly Ser Gly Gly Thr Thr Tyr Tyr Ala Asp Ser Val
    50                  55                  60

Lys Gly Arg Phe Thr Ser Ser Arg Asp Asn Ser Lys Asn Thr Leu Asp
65                  70                  75                  80

Leu Gln Met Asn Ser Leu Gly Val Asp Asp Thr Ala Val Tyr Tyr Cys
                85                  90                  95

Ala Lys Asn Asp Asp Phe Trp Gly Gly Pro Thr Phe Asp Tyr Trp Gly
            100                 105                 110

Gln Gly Thr Leu Val Thr Val Ser Ser
        115                 120
```

<210> SEQ ID NO 120
<211> LENGTH: 109
<212> TYPE: PRT
<213> ORGANISM: Homo sapiens
<220> FEATURE:
<223> OTHER INFORMATION: Light chain of antibody 4T0657

<400> SEQUENCE: 120

```
Gln Ser Val Leu Thr Gln Pro Pro Ser Val Ser Ala Ala Pro Gly Gln
1               5                   10                  15

Lys Val Thr Ile Ser Cys Ser Gly Ile Ser Ser Asn Ile Gly Asn Asn
            20                  25                  30
```

Tyr Val Ser Trp Tyr Gln Gln Leu Pro Gly Thr Ala Pro Lys Leu Leu
35 40 45

Ile Tyr Asp Asn Asn Lys Arg Pro Ser Gly Ile Pro Asp Arg Phe Ser
50 55 60

Ala Ser Lys Ser Gly Thr Ser Ala Thr Leu Gly Ile Thr Gly Leu Gln
65 70 75 80

Thr Gly Asp Glu Ala Asp Tyr Tyr Cys Gly Thr Trp Asp Ile Thr Leu
85 90 95

Ser Glu Gly Val Phe Gly Gly Gly Thr Lys Leu Thr Val
100 105

<210> SEQ ID NO 121
<211> LENGTH: 121
<212> TYPE: PRT
<213> ORGANISM: Homo sapiens
<220> FEATURE:
<223> OTHER INFORMATION: Heavy chain of antibody 4T0726

<400> SEQUENCE: 121

Gln Val Gln Leu Val Gln Ser Gly Val Glu Val Lys Glu Pro Gly Ala
1 5 10 15

Ser Val Arg Val Ser Cys Lys Ala Ser Gly Tyr Thr Phe Thr His Tyr
20 25 30

Gly Ile Thr Trp Val Arg Gln Ala Pro Gly Gln Gly Leu Glu Trp Met
35 40 45

Gly Trp Ile Ser Gly Tyr Asn Gly Asn Thr Asp Tyr Ala Gln Lys Phe
50 55 60

Gln Gly Arg Ile Thr Met Thr Thr Asp Thr Ser Thr Ser Thr Ala Tyr
65 70 75 80

Met Glu Leu Gly Arg Leu Thr Ser Asp Asp Thr Ala Val Tyr Tyr Cys
85 90 95

Ala Arg Thr Ile Thr Met Ile Leu Leu Gly Trp Phe Asp Pro Trp Gly
100 105 110

Gln Gly Thr Leu Val Thr Val Ser Ser
115 120

<210> SEQ ID NO 122
<211> LENGTH: 108
<212> TYPE: PRT
<213> ORGANISM: Homo sapiens
<220> FEATURE:
<223> OTHER INFORMATION: Light chain of antibody 4T0726

<400> SEQUENCE: 122

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Asn
20 25 30

Tyr Leu Ala Trp Tyr Gln Gln Lys Pro Gly Gln Ala Pro Arg Leu Leu
35 40 45

Ile Ser Gly Ala Ser Asn Arg Ala Thr Gly Leu Pro Asp Gly Phe Ser
50 55 60

Gly Ser Gly Ser Gly Thr Asp Phe Thr Leu Thr Ile Ser Arg Leu Glu
65 70 75 80

Pro Glu Asp Phe Ala Val Phe Phe Cys Gln Gln Tyr Gly Thr Ser Pro
85 90 95

Leu Thr Phe Gly Pro Gly Thr Lys Val Asp Ile Lys 100 105

<210> SEQ ID NO 123
<211> LENGTH: 116
<212> TYPE: PRT
<213> ORGANISM: Homo sapiens
<220> FEATURE:
<223> OTHER INFORMATION: Heavy chain of antibody 4T0764

<400> SEQUENCE: 123

Gln Val Gln Leu Gln Glu Ser Gly Pro Gly Leu Val Glu Pro Ser Glu
1 5 10 15

Thr Leu Ser Leu Thr Cys Thr Val Ser Gly Ala Ser Ile Ser Ser Leu
20 25 30

Phe Trp Ser Trp Ile Arg Gln Pro Pro Gly Lys Gly Leu Glu Trp Ile
35 40 45

Gly Tyr Ile His Ser Asp Gly Ser Thr Asn Tyr Asn Pro Phe Leu Lys
50 55 60

Ser Arg Val Thr Ile Ser Ile Asp Thr Ser Gln Asn Gln Phe Ser Leu
65 70 75 80

Arg Leu Thr Ser Val Thr Ala Ala Asp Thr Ala Val Tyr Phe Cys Ala
85 90 95

Arg Gly Leu Leu Gly Ser Gln Asp Ser Trp Gly Gln Gly Thr Leu Val
100 105 110

Thr Val Ser Ser
115

<210> SEQ ID NO 124
<211> LENGTH: 111
<212> TYPE: PRT
<213> ORGANISM: Homo sapiens
<220> FEATURE:
<223> OTHER INFORMATION: Light chain of antibody 4T0764

<400> SEQUENCE: 124

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Gly Tyr
20 25 30

Asn Tyr Val Ser Trp Tyr Gln Gln Tyr Pro Gly Lys Ala Pro Lys Leu
35 40 45

Val Ile Tyr Glu Val Thr Asn Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Arg Ala Glu Asp Glu Ala Asp Tyr His Cys Ser Ser Tyr Arg Thr Arg
85 90 95

Asn Thr His Val Ile Phe Gly Gly Gly Thr Lys Leu Thr Val Leu
100 105 110

<210> SEQ ID NO 125
<211> LENGTH: 127
<212> TYPE: PRT
<213> ORGANISM: Homo sapiens
<220> FEATURE:
<223> OTHER INFORMATION: Heavy chain of antibody 4T0784

<400> SEQUENCE: 125

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Thr Tyr
20 25 30

Gly Val His Trp Val Arg Gln Ala Pro Gly Lys Gly Leu Glu Trp Val
35 40 45

Gly Val Ile Trp Tyr Asp Gly Ser Lys Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Ala Ala Val Tyr Arg Cys
85 90 95

Val Arg Gly Gly Asp Leu Leu Leu Leu Pro Asp Ser Ile Asp Tyr Tyr
100 105 110

Gly Met Asp Val Trp Gly Gln Gly Thr Leu Val Thr Val Ser Ser
115 120 125

<210> SEQ ID NO 126
<211> LENGTH: 107
<212> TYPE: PRT
<213> ORGANISM: Homo sapiens
<220> FEATURE:
<223> OTHER INFORMATION: Light chain of antibody 4T0784

<400> SEQUENCE: 126

Lys Asp His Asp Pro Gln Ala Pro Val Ser Leu Ser Ala Ser Val Gly
1 5 10 15

Asp Arg Val Thr Ile Thr Cys Arg Ala Ser Gln Gly Ile Arg Asn Asp
20 25 30

Leu Gly Trp Tyr Gln Gln Lys Pro Gly Lys Ala Pro Lys Arg Leu Ile
35 40 45

Tyr Ala Ala Ser Ser Leu Gln Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Leu Gln His Asn Thr Tyr Pro Phe
85 90 95

Ser Phe Gly Pro Gly Thr Lys Val Asp Ile Lys
100 105

<210> SEQ ID NO 127
<211> LENGTH: 124
<212> TYPE: PRT
<213> ORGANISM: Homo sapiens
<220> FEATURE:
<223> OTHER INFORMATION: Heavy chain of antibody 5T0107

<400> SEQUENCE: 127

Gln Val Gln Leu Val Glu Ser Gly Gly Thr Val Val Gln Pro Gly Arg
1 5 10 15

Ser Leu Arg Leu Ser Cys Ala Ala Ser Gly Phe Met Phe Ser Asp Tyr
20 25 30

Gly Met Asn Trp Val Arg Gln Ala Pro Gly Lys Gly Leu Glu Trp Val
35 40 45

Asn Phe Ile Ser Ser Asp Gly Thr Arg Thr Tyr Phe Ala Asp Ser Val
50 55 60

Lys Gly Arg Leu Thr Ile Ser Arg Asp Asn Ser Lys Asn Met Val Phe
65 70 75 80

Leu Glu Met Asn Ser Leu Arg Pro Glu Asp Thr Ala Ile Tyr Tyr Cys

```
                85                  90                  95

Ala Lys Asp Arg Tyr Cys Asp Ala Gly Thr Cys Ser Gly Ser Leu Asp
            100                 105                 110

Tyr Trp Gly Gln Gly Thr Leu Val Thr Val Ser Ser
        115                 120


<210> SEQ ID NO 128
<211> LENGTH: 112
<212> TYPE: PRT
<213> ORGANISM: Homo sapiens
<220> FEATURE:
<223> OTHER INFORMATION: Light chain of antibody 5T0107

<400> SEQUENCE: 128

Asp Ile Val Met Thr Gln Ser Pro Leu Tyr Leu Pro Val Thr Pro Gly
1               5                   10                  15

Glu Pro Ala Ser Ile Ser Cys Arg Ser Asn Gln Ser Leu Leu His Ser
            20                  25                  30

Asn Gly Asn Lys Tyr Leu Asp Trp Tyr Leu Gln Lys Pro Gly Gln Ser
        35                  40                  45

Pro Gln Leu Leu Ile Tyr Leu Gly Ser Thr Arg Ala Ser Gly Val Ser
    50                  55                  60

Asp Arg Phe Ser Gly Ser Gly Ser Asp Thr Asp Phe Thr Leu Lys Ile
65                  70                  75                  80

Ser Arg Val Glu Ala Asp Asp Val Gly Val Tyr Tyr Cys Met Gln Ser
                85                  90                  95

Leu Ala Ala Arg Pro Thr Phe Gly Gln Gly Thr Lys Val Glu Ile Lys
            100                 105                 110


<210> SEQ ID NO 129
<211> LENGTH: 124
<212> TYPE: PRT
<213> ORGANISM: Homo sapiens
<220> FEATURE:
<223> OTHER INFORMATION: Heavy chain of antibody 5T0180

<400> SEQUENCE: 129

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Gly Asn Ala
            20                  25                  30

Trp Met Asn Trp Val Arg Gln Ala Pro Gly Lys Gly Leu Glu Trp Val
        35                  40                  45

Gly Arg Ile Lys Ser Lys Ser Asp Gly Gly Thr Thr Asp Tyr Ala Ala
    50                  55                  60

Pro Val Lys Asp Arg Phe Ile Ile Ser Arg Asp Asp Ser Lys Lys Thr
65                  70                  75                  80

Leu Tyr Leu Gln Met Asn Ser Leu Arg Arg Glu Asp Thr Ala Val Tyr
                85                  90                  95

Tyr Cys Val Arg Gly Pro Phe Tyr Cys Asp Thr Cys Gly Pro Asn Asp
            100                 105                 110

Tyr Trp Gly Gln Gly Thr Leu Val Thr Val Ser Ser
        115                 120


<210> SEQ ID NO 130
<211> LENGTH: 112
<212> TYPE: PRT
<213> ORGANISM: Homo sapiens
<220> FEATURE:
```

<223> OTHER INFORMATION: Light chain of antibody 5T0180

<400> SEQUENCE: 130

Gln Ser Val Leu Thr Gln Pro Pro Ser Val Ser Gly Ala Pro Gly Gln
1 5 10 15

Arg Val Thr Ile Ser Cys Thr Gly Ser Ser Ser Asn Ile Gly Ala Gly
20 25 30

Tyr Asp Val Gln Trp Tyr Gln Gln Leu Pro Gly Thr Ala Pro Lys Val
35 40 45

Leu Ile Tyr Gly Asn Asn Asn Arg Pro Ser Gly Val Pro Asp Arg Phe
50 55 60

Ser Gly Ser Lys Ser Gly Ser Ser Ala Ser Leu Ala Ile Thr Gly Leu
65 70 75 80

Gln Ala Glu Asp Glu Ala Asp Tyr Tyr Cys Gln Thr Tyr Asp Ser Arg
85 90 95

Leu Arg Asp Gln Trp Val Phe Gly Gly Gly Thr Lys Leu Thr Val Leu
100 105 110

<210> SEQ ID NO 131
<211> LENGTH: 122
<212> TYPE: PRT
<213> ORGANISM: Homo sapiens
<220> FEATURE:
<223> OTHER INFORMATION: Heavy chain of antibody 5T0202

<400> SEQUENCE: 131

Glu Val Gln Leu Val Glu Ser Gly Gly Gly Leu Val Lys Pro Gly Gly
1 5 10 15

Ser Leu Arg Leu Ser Cys Gly Ala Ser Gly Phe Ser Phe Asn Asp Ala
20 25 30

Trp Met Asn Trp Val Arg Gln Ala Pro Gly Lys Gly Leu Glu Trp Val
35 40 45

Gly Arg Ile Lys Ser Lys Ala Asp Gly Gly Gly Ser Asp Thr Ala Ala
50 55 60

Pro Val Lys Gly Arg Phe Ile Ile Ser Arg Asp Asp Ser Lys Asn Thr
65 70 75 80

Leu Phe Leu Gln Met Glu Arg Leu Lys Ser Glu Asp Thr Gly Val Tyr
85 90 95

Tyr Cys Thr Thr Ser Leu Asn Ile Trp Gly Thr Tyr Arg Asp Cys Trp
100 105 110

Gly Gln Gly Thr Leu Val Thr Val Ser Ser
115 120

<210> SEQ ID NO 132
<211> LENGTH: 112
<212> TYPE: PRT
<213> ORGANISM: Homo sapiens
<220> FEATURE:
<223> OTHER INFORMATION: Light chain of antibody 5T0202

<400> SEQUENCE: 132

Gln Ser Val Leu Thr Gln Pro Pro Ser Val Ser Gly Ala Pro Gly Gln
1 5 10 15

Arg Val Thr Ile Ser Cys Thr Gly Ser Tyr Ser Asn Ile Gly Ala Gly
20 25 30

Tyr Asp Val Arg Trp Tyr Gln Gln Leu Pro Glu Thr Ala Pro Lys Leu
35 40 45

Leu Ile Tyr Gly Asn Asn Asn Arg Pro Ser Gly Val Pro Asp Arg Phe 50 55 60

Ser Gly Ser Lys Ser Gly Thr Ser Ala Ser Leu Ala Ile Thr Gly Leu
65 70 75 80

Gln Ala Glu Asp Glu Ala Asp Tyr Tyr Cys Gln Ser Tyr Asp Ser Arg
85 90 95

Leu Arg Asp Ser Trp Val Phe Gly Gly Gly Thr Arg Leu Thr Val Leu
100 105 110

<210> SEQ ID NO 133
<211> LENGTH: 119
<212> TYPE: PRT
<213> ORGANISM: Homo sapiens
<220> FEATURE:
<223> OTHER INFORMATION: Heavy chain of antibody 5T0209

<400> SEQUENCE: 133

Glu Val Gln Leu Val Asp Ser Gly Gly Gly Leu Val Lys Pro Gly Gly
1 5 10 15

Ser Leu Arg Leu Ser Cys Ala Ala Ser Gly Phe Thr Phe Ser Lys Ala
20 25 30

Trp Met Ser Trp Val Arg Gln Ala Pro Gly Lys Gly Leu Glu Trp Val
35 40 45

Gly Arg Ile Lys Ser Arg Thr Asp Gly Gly Thr Thr Asp Tyr Ala Ala
50 55 60

Pro Val Arg Gly Arg Phe Thr Ile Ser Arg Asp Asp Ser Lys Asn Thr
65 70 75 80

Leu Phe Leu Gln Met Asn Ser Leu Lys Pro Glu Asp Thr Ala Ile Tyr
85 90 95

Tyr Cys Ala Thr Asp Tyr Tyr Glu Ser Arg Gly Tyr Trp Gly Gln Gly
100 105 110

Thr Leu Val Thr Val Ser Ser
115

<210> SEQ ID NO 134
<211> LENGTH: 112
<212> TYPE: PRT
<213> ORGANISM: Homo sapiens
<220> FEATURE:
<223> OTHER INFORMATION: Light chain of antibody 5T0209

<400> SEQUENCE: 134

Gln Ser Val Leu Thr Gln Pro Pro Ser Val Ser Gly Ala Pro Gly Gln
1 5 10 15

Arg Val Thr Ile Ser Cys Thr Gly Ser Ser Ser Asn Ile Gly Ala Gly
20 25 30

Tyr Asp Val Asn Trp Tyr Gln Gln Ile Pro Gly Thr Ala Pro Lys Leu
35 40 45

Leu Ile Tyr Gly Asn Asn Lys Arg Pro Ser Gly Val Pro Asp Arg Phe
50 55 60

Ser Gly Ser Lys Ser Gly Thr Ser Val Ser Leu Ala Ile Thr Gly Leu
65 70 75 80

Gln Ala Glu Asp Glu Ala Asp Tyr Tyr Cys Gln Ser Tyr Asp Ser Arg
85 90 95

Leu Ser Asp His Trp Val Phe Gly Gly Gly Thr Lys Leu Thr Val Leu
100 105 110

<210> SEQ ID NO 135
<211> LENGTH: 118

<212> TYPE: PRT
<213> ORGANISM: Homo sapiens
<220> FEATURE:
<223> OTHER INFORMATION: Heavy chain of antibody 5T0223

<400> SEQUENCE: 135

```
Glu Val Gln Leu Val Glu Ser Gly Gly Gly Leu Val Lys Pro Gly Gly
1               5                   10                  15

Ser Leu Arg Leu Ser Cys Glu Ala Ser Gly Phe Thr Phe Arg Asn Thr
            20                  25                  30

Trp Met Asn Trp Val Arg Gln Ala Pro Gly Lys Gly Leu Glu Trp Val
        35                  40                  45

Gly Arg Ile Lys Ser Asn Thr Asp Gly Gly Thr Ala Asp Tyr Ala Ala
    50                  55                  60

Pro Val Lys Gly Arg Phe Thr Ile Ser Arg Asp Asp Ser Lys Ser Thr
65                  70                  75                  80

Leu Phe Leu Glu Met Ile Ser Leu Arg Thr Glu Asp Thr Gly Phe Tyr
                85                  90                  95

Tyr Cys Thr Lys Gly Gly Pro Gly Ala His Ser Trp Gly Leu Gly Thr
            100                 105                 110

Leu Val Thr Val Ser Ser
        115
```

<210> SEQ ID NO 136
<211> LENGTH: 112
<212> TYPE: PRT
<213> ORGANISM: Homo sapiens
<220> FEATURE:
<223> OTHER INFORMATION: Light chain of antibody 5T0223

<400> SEQUENCE: 136

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val Gln Trp Tyr Gln Gln Leu Pro Gly Thr Ala Pro Lys Val
        35                  40                  45

Leu Ile Tyr His Asn Thr Asn Arg Pro Ser Gly Val Pro Asp Arg Phe
    50                  55                  60

Ser Gly Ser Arg Ser Gly Thr Ser Ala Ser Leu Val Ile Thr Gly Leu
65                  70                  75                  80

Gln Ala Glu Asp Glu Ala Asp Tyr Tyr Cys Gln Thr Tyr Asp Ser Arg
                85                  90                  95

Leu Ser Asp His Trp Val Phe Gly Gly Gly Thr Lys Leu Thr Val Leu
            100                 105                 110
```

<210> SEQ ID NO 137
<211> LENGTH: 121
<212> TYPE: PRT
<213> ORGANISM: Homo sapiens
<220> FEATURE:
<223> OTHER INFORMATION: Heavy chain of antibody 5T0257

<400> SEQUENCE: 137

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
```

```
        35                  40                  45

Ser Ala Ile Ser Gly Ser Gly Gly Ser Thr Tyr Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asp Asp Phe Trp Ser Gly Pro Tyr Phe Asp Tyr Trp Gly
            100                 105                 110

Gln Gly Thr Leu Val Thr Val Ser Ser
        115                 120


<210> SEQ ID NO 138
<211> LENGTH: 110
<212> TYPE: PRT
<213> ORGANISM: Homo sapiens
<220> FEATURE:
<223> OTHER INFORMATION: Light chain of antibody 5T0257

<400> SEQUENCE: 138

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Tyr Asn
            20                  25                  30

Tyr Val Ser Trp Tyr Gln Gln Leu Pro Gly Thr Ala Pro Lys Leu Leu
        35                  40                  45

Ile Tyr Glu Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Ser Trp Asp Ser Ser Leu
                85                  90                  95

Ser Thr Gly Val Phe Gly Gly Gly Thr Lys Leu Thr Val Leu
            100                 105                 110


<210> SEQ ID NO 139
<211> LENGTH: 120
<212> TYPE: PRT
<213> ORGANISM: Homo sapiens
<220> FEATURE:
<223> OTHER INFORMATION: Heavy chain of antibody 5T0278

<400> SEQUENCE: 139

Glu Val Gln Leu Val Glu Ser Gly Gly Gly Leu Val Lys Pro Gly Gly
1               5                   10                  15

Ser Leu Arg Val Ser Cys Ala Ala Ser Gly Phe Pro Phe Thr Asp Ala
            20                  25                  30

Trp Met Ser Trp Val Arg Gln Ala Pro Gly Lys Gly Leu Glu Trp Val
        35                  40                  45

Gly Arg Ile Lys Ser Asn Ser Asp Gly Gly Ile Pro Asp Tyr Ala Ala
    50                  55                  60

Pro Val Lys Gly Arg Phe Thr Ile Ser Arg Asp Asp Ser Lys Arg Thr
65                  70                  75                  80

Leu Tyr Leu Gln Met Asn Ser Leu Lys Thr Glu Asp Thr Gly Tyr Tyr
                85                  90                  95

Tyr Cys Tyr Thr Leu Arg Phe Phe Gly Pro Gly Asn Ser Trp Gly Gln
            100                 105                 110
```

Gly Thr Leu Val Thr Val Ser Ser
115 120

<210> SEQ ID NO 140
<211> LENGTH: 112
<212> TYPE: PRT
<213> ORGANISM: Homo sapiens
<220> FEATURE:
<223> OTHER INFORMATION: Light chain of antibody 5T0278

<400> SEQUENCE: 140

Gln Ser Val Leu Thr Gln Pro Pro Ser Val Ser Gly Ala Pro Gly Gln
1 5 10 15

Arg Ile Thr Ile Ser Cys Thr Gly Ser Tyr Ser Asn Ile Gly Ala Gly
20 25 30

Tyr Asp Val Ser Trp His Gln Gln Leu Pro Gly Lys Ala Pro Lys Leu
35 40 45

Leu Ile Tyr Gly Asn Asn Asn Arg Pro Ser Gly Val Pro Asp Arg Phe
50 55 60

Ser Gly Ser Lys Ser Gly Thr Ser Ala Ser Leu Thr Ile Thr Gly Leu
65 70 75 80

Gln Ala Glu Asp Glu Ala Asp Tyr Tyr Cys Gln Ser Tyr Asp Ala Arg
85 90 95

Leu Arg Asp Gln Val Val Phe Gly Gly Gly Thr Lys Leu Thr Val Leu
100 105 110

<210> SEQ ID NO 141
<211> LENGTH: 122
<212> TYPE: PRT
<213> ORGANISM: Homo sapiens
<220> FEATURE:
<223> OTHER INFORMATION: Heavy chain of antibody 5T0337

<400> SEQUENCE: 141

Glu Val Gln Leu Val Glu Ser Gly Gly Gly Leu Val Lys Pro Gly Gly
1 5 10 15

Ser Leu Arg Ile Ser Cys Ala Ala Ser Gly Phe Thr Phe Asn Asn Ala
20 25 30

Trp Met Asn Trp Val Arg Gln Ser Pro Gly Lys Gly Leu Glu Trp Val
35 40 45

Gly Arg Ile Lys Ser Lys Ser Asp Ala Gly Thr Thr Asp Tyr Ala Ala
50 55 60

Pro Val Lys Gly Arg Phe Ile Ile Ser Arg Asp Asp Ser Lys Lys Thr
65 70 75 80

Leu Phe Leu Gln Met Asn Ser Leu Lys Ile Glu Asp Thr Ala Ile Tyr
85 90 95

Phe Cys Met Thr Gly Phe Glu His Thr Tyr Ser Tyr Phe Asp Leu Trp
100 105 110

Gly Arg Gly Thr Gln Val Thr Val Ser Ser
115 120

<210> SEQ ID NO 142
<211> LENGTH: 113
<212> TYPE: PRT
<213> ORGANISM: Homo sapiens
<220> FEATURE:
<223> OTHER INFORMATION: Light chain of antibody 5T0337

<400> SEQUENCE: 142

Gln Ser Val Leu Thr Gln Pro Pro Ser Val Ser Gly Ala Pro Gly Gln 1 5 10 15

Arg Val Ile Ile Ser Cys Ile Gly Gly Ser Ser Asn Ile Gly Ala Gly
20 25 30

Tyr Asp Val Lys Trp Tyr Gln Gln Leu Leu Pro Gly Thr Ala Pro Arg
35 40 45

Leu Leu Ile Tyr Gly Asn Thr Asn Arg Pro Ser Gly Val Pro Asp Arg
50 55 60

Phe Ser Gly Ser Lys Ser Gly Thr Ser Ala Ser Leu Ala Ile Thr Gly
65 70 75 80

Leu Gln Ala Glu Asp Glu Ala Asp Tyr Tyr Cys Gln Ser Tyr Asp Ser
85 90 95

Arg Leu Arg Asp Ala Trp Val Phe Gly Gly Gly Thr Lys Leu Thr Val
100 105 110

Leu

<210> SEQ ID NO 143
<211> LENGTH: 116
<212> TYPE: PRT
<213> ORGANISM: Homo sapiens
<220> FEATURE:
<223> OTHER INFORMATION: Heavy chain of antibody 5T0376

<400> SEQUENCE: 143

Gln Val Gln Leu Gln Glu Ser Gly Pro Gly Leu Val Lys Pro Ser Glu
1 5 10 15

Thr Leu Ser Leu Thr Cys Ser Val Ser Gly Ala Ser Ile Ser Thr Leu
20 25 30

Tyr Trp Ser Trp Ile Arg Gln Pro Pro Gly Lys Gly Leu Glu Trp Ile
35 40 45

Gly Tyr Met His Ser Ser Gly Thr Thr Asn Tyr Asn Pro Ser Leu Glu
50 55 60

Ser Arg Val Thr Met Ser Ile Asp Thr Ser Arg Asn Gln Phe Ser Leu
65 70 75 80

Lys Leu Thr Ser Val Thr Ala Ala Asp Thr Ala Val Tyr Tyr Cys Ala
85 90 95

Arg Gly Leu Leu Gly Pro Gly Asp Ser Trp Gly Gln Gly Thr Leu Val
100 105 110

Thr Val Ser Ser
115

<210> SEQ ID NO 144
<211> LENGTH: 111
<212> TYPE: PRT
<213> ORGANISM: Homo sapiens
<220> FEATURE:
<223> OTHER INFORMATION: Light chain of antibody 5T0376

<400> SEQUENCE: 144

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Gly Tyr
20 25 30

Asn Tyr Val Ser Trp Tyr Gln Gln Tyr Pro Gly Lys Ala Pro Lys Leu
35 40 45

Met Ile Tyr Glu Val Thr Ser Arg Pro Ser Gly Val Ser Asn Arg Phe
50 55 60

Ser Gly Ser Lys Ser Gly Asn Thr Ala Ser Leu Thr Ile Ser Gly Leu 65 70 75 80

Gln Ala Glu Asp Glu Gly Asp Tyr Tyr Cys Ser Ser Tyr Lys Thr Gly
85 90 95

Ser Thr Pro Val Val Phe Gly Gly Gly Thr Lys Leu Thr Val Leu
100 105 110

<210> SEQ ID NO 145
<211> LENGTH: 114
<212> TYPE: PRT
<213> ORGANISM: Homo sapiens
<220> FEATURE:
<223> OTHER INFORMATION: Heavy chain of antibody 5T0378

<400> SEQUENCE: 145

Gln Leu Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Ser
20 25 30

Ser Tyr Tyr Trp Gly Trp Ile Arg Gln Pro Pro Gly Lys Gly Leu Glu
35 40 45

Trp Ile Gly Thr Ile Ser Tyr Ser Gly Ser Thr Tyr Tyr Asn Pro Ser
50 55 60

Leu Lys Ser Arg Val Thr Ile Ser Leu Asp Thr Ser Lys Asn Gln Phe
65 70 75 80

Ser Leu Arg Leu Ser Ser Val Thr Ala Ala Asp Thr Ala Val Tyr Tyr
85 90 95

Cys Ala Arg Arg Phe Asp Tyr Trp Gly Gln Gly Thr Leu Val Thr Val
100 105 110

Ser Ser

<210> SEQ ID NO 146
<211> LENGTH: 107
<212> TYPE: PRT
<213> ORGANISM: Homo sapiens
<220> FEATURE:
<223> OTHER INFORMATION: Light chain of antibody 5T0378

<400> SEQUENCE: 146

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Ser Ser Asn
20 25 30

Leu Ala Trp Tyr Gln Gln Lys Pro Gly Gln Ala Pro Arg Leu Leu Ile
35 40 45

Tyr Gly Ala Ser Thr Arg Ala Thr Gly Ile Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Tyr Asn Asn Trp Pro Trp
85 90 95

Thr Phe Gly Gln Gly Thr Lys Val Glu Ile Lys
100 105

<210> SEQ ID NO 147
<211> LENGTH: 125
<212> TYPE: PRT
<213> ORGANISM: Homo sapiens
<220> FEATURE:
<223> OTHER INFORMATION: Heavy chain of antibody 5T0404

<400> SEQUENCE: 147

```
Gln Val Gln Leu Val Gln Ser Gly Ala Glu Val Lys Lys Pro Gly Ser
1               5                   10                  15

Ser Val Lys Leu Ala Cys Lys Ala Ser Gly Asp Thr Phe Thr Thr Tyr
            20                  25                  30

Pro Ile Thr Trp Val Arg Gln Ala Pro Gly Arg Gly Leu Glu Trp Met
        35                  40                  45

Gly Arg Ile Ile Pro Met Leu Ala Ala Glu Thr Tyr Ala Gln Lys Phe
    50                  55                  60

Leu Gly Arg Leu Ala Ile Thr Ala Asp Lys Ser Thr Asn Thr Val Tyr
65                  70                  75                  80

Met Val Leu Asn Ser Leu Arg Ser Glu Asp Thr Ala Val Tyr Phe Cys
                85                  90                  95

Ala Arg Leu Tyr Cys Ser Ser Ser Ser Cys Ser Ile Tyr Asn Tyr Met
            100                 105                 110

Asp Val Trp Gly Lys Gly Thr Thr Val Thr Val Ser Ser
        115                 120                 125
```

<210> SEQ ID NO 148
<211> LENGTH: 107
<212> TYPE: PRT
<213> ORGANISM: Homo sapiens
<220> FEATURE:
<223> OTHER INFORMATION: Light chain of antibody 5T0404

<400> SEQUENCE: 148

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Ala Lys Ala Pro Glu Leu Leu Ile
        35                  40                  45

Tyr Asp Ala Ser Asn Leu Glu Ala Gly Val Pro Ser Arg Phe Ser Gly
    50                  55                  60

Gly Gly Ser Gly Thr Asp Phe Ser Leu Thr Ile Asn Ser Leu Gln Pro
65                  70                  75                  80

Glu Asp Ile Ala Thr Tyr Tyr Cys Gln Gln Tyr Asp Ser Leu Pro Tyr
                85                  90                  95

Ser Phe Gly Gln Gly Thr Lys Leu Glu Ile Lys
            100                 105
```

<210> SEQ ID NO 149
<211> LENGTH: 126
<212> TYPE: PRT
<213> ORGANISM: Homo sapiens
<220> FEATURE:
<223> OTHER INFORMATION: Heavy chain of antibody 5T0406

<400> SEQUENCE: 149

```
Gln Val Gln Leu Val Gln Ser Gly Pro Glu Val Lys Lys Pro Gly Ser
1               5                   10                  15

Ser Val Arg Val Ser Cys Lys Pro Ser Gly Gly Thr Phe Asn Ser Tyr
            20                  25                  30

Ala Ile Thr Trp Val Arg Gln Ala Pro Gly Gln Gly Leu Glu Trp Met
        35                  40                  45

Gly Gly Ile Ile Pro Ile Phe Asp Thr Pro Lys Tyr Ala Gln Lys Phe
    50                  55                  60
```

Gln Asp Arg Val Thr Leu Thr Ala Asp Glu Ser Thr Thr Thr Thr Tyr
65 70 75 80

Met Glu Leu Asn Ser Leu Arg Ser Glu Asp Thr Ala Val Tyr Phe Cys
85 90 95

Ala Arg Phe Arg Phe Phe Gln Gly Gly Gly Ser Phe Tyr Tyr Tyr Gly
100 105 110

Leu Asp Leu Trp Gly Gln Gly Thr Ala Val Thr Val Ser Ser
115 120 125

<210> SEQ ID NO 150
<211> LENGTH: 112
<212> TYPE: PRT
<213> ORGANISM: Homo sapiens
<220> FEATURE:
<223> OTHER INFORMATION: Light chain of antibody 5T0406

<400> SEQUENCE: 150

Gln Ser Val Leu Thr Gln Pro Pro Ser Ala Ser Gly Thr Pro Gly Gln
1 5 10 15

Arg Val Thr Ile Ser Cys Ser Gly Ser Asn Ser Asn Ile Gly Ser Asn
20 25 30

Pro Val Asn Trp Tyr Gln His Leu Pro Gly Thr Ala Pro Lys Leu Leu
35 40 45

Ile Tyr Ser Asp Asn Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Ala Ala Trp Asp Asp Arg Leu
85 90 95

Asn Gly Pro Gly Tyr Val Phe Gly Thr Gly Thr Thr Val Thr Val Leu
100 105 110

<210> SEQ ID NO 151
<211> LENGTH: 114
<212> TYPE: PRT
<213> ORGANISM: Homo sapiens
<220> FEATURE:
<223> OTHER INFORMATION: Heavy chain of antibody 5T0420

<400> SEQUENCE: 151

Gln Leu Gln Leu Gln Glu Ser Gly Pro Gly Leu Val Lys Pro Ser Glu
1 5 10 15

Thr Leu Ser Leu Val Cys Thr Val Ser Gly Gly Ser Ile Ser Ser Ser
20 25 30

Ser Phe Tyr Trp Gly Trp Ile Arg Gln Pro Pro Gly Lys Gly Leu Glu
35 40 45

Trp Ile Ala Thr Ile Ser Asn Leu Gly Ser Thr Tyr Tyr Asn Pro Ser
50 55 60

Leu Lys Ser Arg Val Thr Ile Ser Val Asp Thr Ser Arg Lys His Leu
65 70 75 80

Ser Leu Lys Leu Asn Ser Val Thr Ala Ala Asp Thr Ala Val Tyr Phe
85 90 95

Cys Ala Arg Arg Phe Asp Leu Trp Gly Arg Gly Thr Leu Val Thr Val
100 105 110

Ser Ser

<210> SEQ ID NO 152

```
<211> LENGTH: 107
<212> TYPE: PRT
<213> ORGANISM: Homo sapiens
<220> FEATURE:
<223> OTHER INFORMATION: Light chain of antibody 5T0420

<400> SEQUENCE: 152

Glu Ile Val Met Thr Gln Ser Pro Ala Thr Leu Ser Val Ser Pro Gly
1               5                   10                  15

Gln Arg Ala Thr Leu Ser Cys Arg Ala Ser Gln Ser Val Gly Thr Asn
            20                  25                  30

Leu Ala Trp Phe Gln Gln Lys Pro Gly Gln Ala Pro Arg Leu Leu Ile
        35                  40                  45

Tyr Gly Glu Ser Thr Arg Ala Thr Asp Ile Pro Ala Arg Phe Ser Gly
    50                  55                  60

Ser Gly Ser Gly Thr Asp Phe Thr Leu Thr Ile Thr Ser Leu Gln Ser
65                  70                  75                  80

Glu Asp Phe Ala Val Tyr Tyr Cys Gln Gln Tyr Asn Ile Trp Pro Trp
                85                  90                  95

Thr Phe Gly Gln Gly Thr Lys Val Glu Ile Lys
            100                 105


<210> SEQ ID NO 153
<211> LENGTH: 123
<212> TYPE: PRT
<213> ORGANISM: Homo sapiens
<220> FEATURE:
<223> OTHER INFORMATION: Heavy chain of antibody 5T0451

<400> SEQUENCE: 153

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Asn Ala
            20                  25                  30

Trp Met Asn Trp Val Arg Gln Ala Pro Gly Lys Gly Leu Glu Trp Ile
        35                  40                  45

Gly Arg Ile Lys Ser Lys Gly Asp Gly Gly Thr Ala Asp His Ala Ala
    50                  55                  60

Pro Val Arg Gly Arg Phe Ile Ile Ser Arg Asp Asp Ser Lys Gln Met
65                  70                  75                  80

Leu Tyr Leu Gln Met Thr Gly Leu Lys Ser Asp Asp Thr Ala Val Tyr
                85                  90                  95

Tyr Cys Thr Arg Gly Pro Tyr Asp Asn Phe Ser Gly Trp Arg Asp Tyr
            100                 105                 110

Trp Gly Gln Gly Thr Leu Val Thr Val Ser Ser
        115                 120


<210> SEQ ID NO 154
<211> LENGTH: 112
<212> TYPE: PRT
<213> ORGANISM: Homo sapiens
<220> FEATURE:
<223> OTHER INFORMATION: Light chain of antibody 5T0451

<400> SEQUENCE: 154

Gln Ser Val Leu Thr Gln Pro Pro Ser Val Ser Gly Ala Pro Gly Gln
1               5                   10                  15

Arg Val Thr Ile Ser Cys Thr Gly Ser Gly Ser Asn Ile Gly Ala Gly
            20                  25                  30
```

```
Tyr Asp Val Gln Trp Tyr Gln Gln His Pro Gly Thr Ala Pro Lys Val
        35                  40                  45

Leu Ile Tyr Gly Asn Asn Lys Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala His Tyr Tyr Cys Gln Ser Tyr Asp Ala Arg
                85                  90                  95

Leu Arg Asp Ser Trp Val Phe Gly Gly Gly Thr Gln Leu Thr Val Leu
            100                 105                 110


<210> SEQ ID NO 155
<211> LENGTH: 119
<212> TYPE: PRT
<213> ORGANISM: Homo sapiens
<220> FEATURE:
<223> OTHER INFORMATION: Heavy chain of antibody 5T0465

<400> SEQUENCE: 155

Gln Val Gln Leu Val Gln Ser Gly Ala Glu Val Arg Glu Pro Gly Ala
1               5                   10                  15

Ser Val Arg Ile Ser Cys Lys Ala Ser Gly Tyr Thr Phe Thr Ser Ala
            20                  25                  30

Ser Ile His Trp Val Arg Gln Ala Pro Gly Gln Gly Leu Glu Trp Met
        35                  40                  45

Gly Ile Ile Asp Pro Val Val Gly Lys Thr Arg Ser Glu Arg Lys Phe
    50                  55                  60

Asn Gly Arg Leu Ile Met Thr Arg Asp Thr Pro Thr Ser Thr Val Tyr
65                  70                  75                  80

Met Glu Leu Asn Ser Leu Arg Ser Asp Asp Thr Ala Met Tyr Tyr Cys
                85                  90                  95

Ala Arg Ser Gly Tyr Tyr Pro Arg Gly Met Asp Val Trp Gly Gln Gly
            100                 105                 110

Thr Thr Val Thr Val Ser Ser
        115


<210> SEQ ID NO 156
<211> LENGTH: 107
<212> TYPE: PRT
<213> ORGANISM: Homo sapiens
<220> FEATURE:
<223> OTHER INFORMATION: Light chain of antibody 5T0465

<400> SEQUENCE: 156

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Glu Tyr Val
            20                  25                  30

Ser Trp Tyr Gln Gln Lys Pro Gly Gln Ser Pro Val Leu Val Ile Ser
        35                  40                  45

Arg Asp Thr Arg Arg Ser Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Val
                85                  90                  95

Val Phe Gly Gly Gly Thr Lys Leu Thr Val Leu
            100                 105
```

<210> SEQ ID NO 157
<211> LENGTH: 2142
<212> TYPE: DNA
<213> ORGANISM: Artificial Sequence
<220> FEATURE:
<223> OTHER INFORMATION: Nucleotide sequence of EBOV delta TM

<400> SEQUENCE: 157
atgggtgtta caggaatatt gcagttacct cgtgatcgat tcaagaggac atcattcttt 60
ctttgggtaa ttatcctttt ccaaagaaca ttttccatcc cgcttggagt tatccacaat 120
agtacattac aggttagtga tgtcgacaaa ctagtttgtc gtgacaaact gtcatccaca 180
aatcaattga gatcagttgg actgaatctc gaggggaatg gagtggcaac tgacgtgcca 240
tctgcgacta aaagatgggg cttcaggtcc ggtgtcccac caaaggtggt caattatgaa 300
gctggtgaat gggctgaaaa ctgctacaat cttgaaatca aaaaacctga cgggagtgag 360
tgtctaccag cagcgccaga cgggattcgg ggcttccccc ggtgccggta tgtgcacaaa 420
gtatcaggaa cgggaccatg tgccggagac tttgccttcc acaaagaggg tgctttcttc 480
ctgtatgatc gacttgcttc cacagttatc taccgaggaa cgactttcgc tgaaggtgtc 540
gttgcatttc tgatactgcc ccaagctaag aaggacttct tcagctcaca ccccttgaga 600
gagccggtca atgcaacgga ggacccgtcg agtggctatt attctaccac aattagatat 660
caggctaccg gttttggaac taatgagaca gagtacttgt tcgaggttga caatttgacc 720
tacgtccaac ttgaatcaag attcacacca cagtttctgc tccagctgaa tgagacaata 780
tatgcaagtg ggaagaggag caacaccacg ggaaaactaa tttggaaggt caaccccgaa 840
attgatacaa caatcgggga gtgggccttc tgggaaacta aaaaaaacct cactagaaaa 900
attcgcagtg aagagttgtc tttcacagct gtatcaaacg gacccaaaaa catcagtggt 960
cagagtccgg cgcgaacttc ttccgaccca gagaccaaca caacaaatga agaccacaaa 1020
atcatggctt cagaaaattc ctctgcaatg gttcaagtgc acagtcaagg aaggaaagct 1080
gcagtgtcgc atctgacaac ccttgccaca atctccacga gtcctcaacc tcccacaacc 1140
aaaacaggtc cggacaacag cacccataat acacccgtgt ataaacttga catctctgag 1200
gcaactcaag ttggacaaca tcaccgtaga gcagacaacg acagcacagc ctccgacact 1260
ccccccgcca cgaccgcagc cggaccctta aaagcagaga acaccaacac gagtaagagc 1320
gctgactccc tggacctcgc caccacgaca agcccccaaa actacagcga gactgctggc 1380
aacaacaaca ctcatcacca agataccgga gaagagagtg ccagcagcgg gaagctaggc 1440
ttaattacca atactattgc tggagtagca ggactgatca caggcgggag aaggactcga 1500
agagaagtaa ttgtcaatgc tcaacccaaa tgcaacccca atttacatta ctggactact 1560
caggatgaag gtgctgcaat cggattggcc tggataccat atttcgggcc agcagccgaa 1620
ggaatttaca cagaggggct aatgcacaac caagatggtt taatctgtgg gttgaggcag 1680
ctggccaacg aaacgactca agctctccaa ctgttcctga gagccacaac tgagctgcga 1740
accttttcaa tcctcaaccg taaggcaatt gacttcctgc tgcagcgatg ggtggcaca 1800 tgccacattt tgggaccgga ctgctgtatc gaaccacatg attggaccaa gaacataaca 1860
gacaaaattg atcagattat tcatgatttt gttgataaaa cccttccgga ccagggggac 1920
aatgacaatt ggtggacagg atggagacaa atgaaacaga tagaggacaa gatagaagag 1980
atcttaagca aaatctacca tattgaaaat gagatcgcac ggataaaaaa actgatcggt 2040
gaggtcgcat caagctccat cgaggggcgg ggcagccacc accatcatca ccacggtctg 2100
aacgacatct tcgaggctca gaaaatcgaa tggcacgaat ag 2142

<210> SEQ ID NO 158
<211> LENGTH: 713
<212> TYPE: PRT
<213> ORGANISM: Artificial Sequence
<220> FEATURE:
<223> OTHER INFORMATION: Protein sequence of EBOV delta TM

<400> SEQUENCE: 158

Met Gly Val Thr Gly Ile Leu Gln Leu Pro Arg Asp Arg Phe Lys Arg
1 5 10 15

Thr Ser Phe Phe Leu Trp Val Ile Ile Leu Phe Gln Arg Thr Phe Ser
20 25 30

Ile Pro Leu Gly Val Ile His Asn Ser Thr Leu Gln Val Ser Asp Val
35 40 45

Asp Lys Leu Val Cys Arg Asp Lys Leu Ser Ser Thr Asn Gln Leu Arg
50 55 60

Ser Val Gly Leu Asn Leu Glu Gly Asn Gly Val Ala Thr Asp Val Pro
65 70 75 80

Ser Ala Thr Lys Arg Trp Gly Phe Arg Ser Gly Val Pro Pro Lys Val
85 90 95

Val Asn Tyr Glu Ala Gly Glu Trp Ala Glu Asn Cys Tyr Asn Leu Glu
100 105 110

Ile Lys Lys Pro Asp Gly Ser Glu Cys Leu Pro Ala Ala Pro Asp Gly
115 120 125

Ile Arg Gly Phe Pro Arg Cys Arg Tyr Val His Lys Val Ser Gly Thr
130 135 140

Gly Pro Cys Ala Gly Asp Phe Ala Phe His Lys Glu Gly Ala Phe Phe
145 150 155 160

Leu Tyr Asp Arg Leu Ala Ser Thr Val Ile Tyr Arg Gly Thr Thr Phe
165 170 175

Ala Glu Gly Val Val Ala Phe Leu Ile Leu Pro Gln Ala Lys Lys Asp
180 185 190

Phe Phe Ser Ser His Pro Leu Arg Glu Pro Val Asn Ala Thr Glu Asp
195 200 205

Pro Ser Ser Gly Tyr Tyr Ser Thr Thr Ile Arg Tyr Gln Ala Thr Gly
210 215 220

Phe Gly Thr Asn Glu Thr Glu Tyr Leu Phe Glu Val Asp Asn Leu Thr
225 230 235 240

Tyr Val Gln Leu Glu Ser Arg Phe Thr Pro Gln Phe Leu Leu Gln Leu
245 250 255

Asn Glu Thr Ile Tyr Ala Ser Gly Lys Arg Ser Asn Thr Thr Gly Lys
260 265 270

Leu Ile Trp Lys Val Asn Pro Glu Ile Asp Thr Thr Ile Gly Glu Trp
275 280 285

Ala Phe Trp Glu Thr Lys Lys Asn Leu Thr Arg Lys Ile Arg Ser Glu
290 295 300

Glu Leu Ser Phe Thr Ala Val Ser Asn Gly Pro Lys Asn Ile Ser Gly
305 310 315 320

Gln Ser Pro Ala Arg Thr Ser Ser Asp Pro Glu Thr Asn Thr Thr Asn
325 330 335

Glu Asp His Lys Ile Met Ala Ser Glu Asn Ser Ser Ala Met Val Gln
340 345 350

-continued

```
Val His Ser Gln Gly Arg Lys Ala Ala Val Ser His Leu Thr Thr Leu
        355                 360                 365

Ala Thr Ile Ser Thr Ser Pro Gln Pro Pro Thr Thr Lys Thr Gly Pro
    370                 375                 380

Asp Asn Ser Thr His Asn Thr Pro Val Tyr Lys Leu Asp Ile Ser Glu
385                 390                 395                 400

Ala Thr Gln Val Gly Gln His His Arg Arg Ala Asp Asn Asp Ser Thr
                405                 410                 415

Ala Ser Asp Thr Pro Pro Ala Thr Thr Ala Ala Gly Pro Leu Lys Ala
            420                 425                 430

Glu Asn Thr Asn Thr Ser Lys Ser Ala Asp Ser Leu Asp Leu Ala Thr
        435                 440                 445

Thr Thr Ser Pro Gln Asn Tyr Ser Glu Thr Ala Gly Asn Asn Asn Thr
    450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
                485                 490                 495

Arg Arg Thr Arg Arg Glu Val Ile Val Asn Ala Gln Pro Lys Cys Asn
            500                 505                 510

Pro Asn Leu His Tyr Trp Thr Thr Gln Asp Glu Gly Ala Ala Ile Gly
        515                 520                 525

Leu Ala Trp Ile Pro Tyr Phe Gly Pro Ala Ala Glu Gly Ile Tyr Thr
    530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
    610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Met Lys Gln Ile Glu Asp
                645                 650                 655

Lys Ile Glu Glu Ile Leu Ser Lys Ile Tyr His Ile Glu Asn Glu Ile
            660                 665                 670

Ala Arg Ile Lys Lys Leu Ile Gly Glu Val Ala Ser Ser Ser Ile Glu
        675                 680                 685

Gly Arg Gly Ser His His His His His His Gly Leu Asn Asp Ile Phe
    690                 695                 700

Glu Ala Gln Lys Ile Glu Trp His Glu
705                 710
```

ANTIBODIES AGAINST INFECTIOUS PATHOGENS AND METHOD FOR PRODUCTION THEREOF

CROSS REFERENCE TO RELATED APPLICATIONS

This application claims priority to PCT/EP2020/078109, filed on Oct. 7, 2020, which claims the benefit of European Application No. 19201736.6, filed on Oct. 7, 2019, the entire contents of which are incorporated by reference herein.

SEQUENCE LISTING

The instant application contains a Sequence Listing which has been submitted electronically in ASCII format and is hereby incorporated by reference in its entirety. Said ASCII copy, created on Apr. 1, 2022, is named SequenceListing.txt and is 172,000 bytes in size.

TECHNICAL FIELD

The present invention relates to a method for obtaining monoclonal human antibodies directed against an infectious pathogen, monoclonal human antibodies or binding fragments thereof which are directed against an infectious pathogen as obtained by the method of the invention, a pharmaceutical composition comprising such monoclonal human antibodies, a kit comprising such antibodies, and the monoclonal human antibodies or binding fragments thereof, the pharmaceutical composition and the kit for use as a medicament and for use in the treatment or prevention of a disease caused by the infectious pathogen.

BACKGROUND OF THE INVENTION

*Ebolaviruses* can cause severe infections in humans leading to unpredictable epidemics with mortality rates up to 90%. The devastating outbreak in West Africa (2013-2016) caused >11,000 confirmed deaths. The severe and since 2018 ongoing outbreak in the Democratic Republic of the Congo (DRC) highlights the significant impact of Ebola virus disease (EVD) and the critical need for efficacious countermeasures.

Different *Ebolavirus* species can cause symptomatic infection in humans. These are Sudan *Ebolavirus* (SUDV), Bundibugyo *Ebolavirus* (BDBV), and Zaire *Ebolavirus* (EBOV), of which the latter accounts for the 2018-2019 outbreak in the DRC. Studies in animal models demonstrated that neutralizing antibodies can prevent infection and are effective for post-exposure prophylaxis.

Therefore, monoclonal antibodies have been evaluated in clinical trials and administered to patients suffering from EVD. For instance, a combination of three antibodies obtained from immunized mice (REGN-EB3) was tested in a phase I clinical trial (Sivapalasingam, S. et al. *The Lancet Infectious Diseases* 18, 884-893, doi:10.1016/s1473-3099(18)30397-9 (2018). Moreover, the neutralizing antibody mAb114 that was isolated from an EVD survivor has been tested in a clinical trial and demonstrated a preferential pharmacokinetic and safety profile (Gaudinski, M. R. et al. *The Lancet*, doi:10.1016/s0140-6736(19)30036-4 (2019).

Until recently, efficacy data in humans were mostly limited to the ZMapp cocktail comprising three human-mouse chimeric antibodies called 13C6, C2G4, and C4G7. During the 2013-2016 epidemic, ZMapp was tested in EVD patients, reducing fatality rates from 37% to 22% (Davey, R. T., Jr. et al. *N Engl J Med* 375, 1448-1456, doi:10.1056/NEJMoa1604330 (2016).

More promising results were very recently reported for REGN-EB3 and mAb114 that were administered to EVD patients in a multicenter, randomized controlled clinical trial. In an interim analysis from 499 participants, lethal outcome was markedly reduced from 67% to 29% and 34% for REGN-EB3 and mAb114, respectively (Kupferschmidt, K. *Science* Latest News, doi:10.1126/science.aaz1032 (2019).

In addition to passive immunotherapy, several vaccine candidates have been developed. Among them, the recombinant vesicular stomatitis virus (VSV)-based vector carrying the EBOV glycoprotein (rVSV-ZEBOV) is the most advanced vaccine and has been administered to >180,000 individuals. rVSV-ZEBOV has been demonstrated to be protective against lethal EBOV challenges in rodents and NHPs.

Moreover, results of two ring vaccination trials estimate vaccine efficiency to be around 97%. As a vaccine candidate with efficacy, rVSV-ZEBOV has been designated as a lead candidate for administration in current and future EVD outbreaks. However, despite its broad application, a detailed understanding of the rVSV-ZEBOV immune response is still limited and no analysis has been performed to elucidate the molecular composition of the induced antibody response.

To date, only a very limited number of functional antibodies against infectious pathogens such as the Ebola virus are available of which only a very small percentage is monoclonal and of a human origin, thus having excellent expected tolerability when administered to human patients.

Additional monoclonal antibodies of a human origin against evasive and highly infectious pathogens, such as viruses including Ebola virus, HI virus and others, are difficult to obtain and highly sought after. Such antibodies could allow a treatment of infected patients, prevention of large outbreaks or contraction of the disease by subjects at risk and could thus serve to additionally reduce the high mortality rate observed in EVD patients and other patients suffering from or at risk or contracting infectious diseases associated with a high mortality.

Prior investigations have exclusively focused on extracting potentially functional and specific antibodies against infectious pathogens from surviving patients, as is the case for known and established functional human Ebola antibodies.

This, however, poses the problem of an extremely limited availability of antibody sources in form of rare survivors of the diseases caused by infectious pathogens. The cases of mAb100 and mAb114 which are accepted for administration either in combination or as mAb114 monotherapy for EVD patients exemplify the difficulty of obtaining additional and novel antibodies from human survivors.

Both of mAb100 and mAb114 have been recovered from the same, single individual after over twenty years after recovery from Ebola infection. This alone already shows the difficulties and time which may be required after infection to successfully obtain additional functional antibodies from disease survivors as antibody sources.

Most of all, the strategy of obtaining antibodies from human survivors has two other significant disadvantages.

First, it must be possible for humans to survive an infection and/or develop immunity against the pathogen to be able to serve as potential sources for such antibodies. This can be extremely difficult for various diseases including inter alia Ebola, Marburg, Rabies or Lassa viruses but not limited thereto. This means that survivors can be extremely difficult or even impossible to find as useful sources for human antibodies for certain diseases.

Second, aiming at survivors of a disease caused by an infectious pathogen as a source for functional human antibodies necessarily requires human subjects, which have contracted that disease and suffer or have suffered from the diseases' symptoms. This also means that an endemic or an epidemic involving numerous sick or dying patients has to necessarily precede the option of obtaining new treatment possibilities.

Both disadvantages are sought to be overcome in the search for novel human monoclonal antibodies directed against infectious pathogens, such as Ebola virus.

Thus, it is an object of the present invention to provide a novel method for obtaining additional human monoclonal antibodies against infectious pathogens, which does not require finding patients having survived the disease caused by such infectious pathogens. Furthermore, it is another object of the present invention to provide novel human monoclonal antibodies against such diseases caused by infectious pathogens.

SUMMARY OF THE INVENTION

These objects have been solved by the aspects of the present invention as specified hereinafter.

According to the first aspect of the present invention, a method for obtaining human antibodies directed against an infectious pathogen, preferably against a virus, is provided, wherein the method comprises vaccination of a human subject with a vaccine comprising an antigenic protein derived from the infectious pathogen, preferably an antigenic protein ordinarily expressed on the surface of the infectious pathogen, isolating B lymphocytes exhibiting antibodies directed against the infectious pathogen on their cell surface and/or antibodies directed against the infectious pathogen from vaccinated subjects, identifying B lymphocytes expressing antibodies directed against the infectious pathogen and/or antibodies directed against the infectious pathogen, preferably on a single cell- or single antibody-basis, and expressing monoclonal antibodies directed against the infectious pathogen.

According to a preferred embodiment of the first aspect of the present invention, the vaccination is an intentional vaccination of a human subject.

According to another preferred embodiment of the first aspect of the present invention, the infectious pathogen is a virus from the family Filoviridae, more preferably from the genus *Ebolavirus* or *Marburgvirus*, even more preferably from the genus *Ebolavirus*, and/or wherein the antigenic protein derived from the infectious pathogen is an *Ebolavirus* glycoprotein.

According to yet another preferred embodiment of the first aspect of the present invention, the antigenic protein is present in the vaccine as part of an attenuated virus, which is different from the infectious pathogen, more preferably as part of an attenuated recombinant vesicular stomatitis virus.

According to a specifically preferred embodiment of the first aspect of the present invention, the vaccine comprises rVSV-ZEBOV.

According to one preferred embodiment of the first aspect of the present invention, the step of isolating B lymphocytes exhibiting antibodies directed against the infectious pathogen on their cell surface and/or antibodies directed against the infectious pathogen comprises first extracting B lymphocytes of the vaccinated subject, and then carrying out serial limiting dilutions, more preferably to single cell level.

According to another preferred embodiment of the first aspect of the present invention, the step of isolating B lymphocytes exhibiting antibodies directed against the infectious pathogen on their cell surface and/or antibodies directed against the infectious pathogen comprises first extracting B lymphocytes of the vaccinated subject and then contacting the extracted B lymphocytes with a component of the infectious pathogen to allow selective sorting of the extracted B lymphocytes which exhibit antibodies directed against the infectious pathogen on their cell surface, more preferably wherein selective sorting comprises fluorescence-activated cell sorting (FACS), magnetic-activated cell sorting (MACS) or chromatographic separation.

According to a more preferred embodiment of the previous preferred embodiment of the first aspect of the present invention, B lymphocytes exhibiting antibodies directed against the infectious pathogen on their cell surface and/or antibodies directed against the infectious pathogen are isolated from vaccinated subjects by contacting extracted B lymphocytes with a component of the infectious pathogen labelled with a fluorescence marker, and isolating B lymphocytes exhibiting antibodies directed against the infectious pathogen on their cell surface by fluorescence-activated cell sorting (FACS), even more preferably in a single cell-manner.

According to a preferred embodiment of the first aspect of the present invention, the step of identifying B lymphocytes exhibiting antibodies directed against the infectious pathogen on their cell surface and/or antibodies directed against the infectious pathogen, more preferably on a single cell- or single antibody-basis, comprises amplifying nucleotide sequences coding for light and heavy chains of each individual antibody, and sequencing the amplified nucleotide sequences of said light and heavy chains.

According to another preferred embodiment of the first aspect of the present invention, the step of expressing a monoclonal antibody directed against the infectious pathogen comprises cloning of the light and heavy chain sequences into a mAb expression vector, transfecting the mAb expression vector into a suitable host cell, culturing the suitable host cell, and harvesting the expressed monoclonal antibody from the host cell supernatant.

According to the second aspect of the present invention, a monoclonal human antibody or binding fragment thereof is provided which is directed against an infectious pathogen, wherein the human antibody is obtained by the method according to the first aspect of the present invention.

According to a preferred embodiment of the second aspect of the present invention, the infectious pathogen is a virus from the family Filoviridae, more preferably from the genus *Ebolavirus* or *Marburgvirus*, even more preferably from the genus *Ebolavirus*.

According to another preferred embodiment of the second aspect of the present invention, the monoclonal human antibody comprises an amino acid sequence encoded by the heavy chain V gene segment IGHV3-15 or an amino acid sequence being at least 80% identical thereto, and an amino acid sequence encoded by the light chain V gene segment IGLV1-40 or an amino acid sequence being at least 80% identical thereto.

According to one preferred embodiment of the second aspect of the present invention, the monoclonal human antibody or binding fragment thereof exhibits reactivity with more than one virus from the family Filoviridae, more preferably with at least two selected from the group comprising Bundibugyo virus, Marburg virus, Sudan virus, and Zaire *Ebolavirus*.

According to another preferred embodiment of the second aspect of the present invention, the monoclonal human antibody or binding fragment thereof exhibits neutralization of *Ebolavirus* in a neutralization assay at a concentration of 1 μg/mL or less, preferably at 0.74 μg/mL or less, more preferably at 0.05 μg/mL or less, even more preferably at 0.01 μg/mL or less.

According to one preferred embodiment of the second aspect of the present invention, the monoclonal human antibody or binding fragment thereof exhibits superior neutralization of *Ebolavirus* in a neutralization assay in comparison to mAb100.

According to a preferred embodiment of the second aspect of the present invention, the antibody or binding fragment thereof comprises the heavy chain CDR1 to CDR3 and the light chain CDR1 to CDR3 amino acid sequence of one antibody from the group comprising 1T0129 (consisting of the heavy chain amino acid sequence of SEQ ID No. 1 and the light chain amino acid sequence of SEQ ID No. 2), 1T0139 (consisting of the heavy chain amino acid sequence of SEQ ID No. 3 and the light chain amino acid sequence of SEQ ID No. 4), 1T0201 (consisting of the heavy chain amino acid sequence of SEQ ID No. 5 and the light chain amino acid sequence of SEQ ID No. 6), 1T0221 (consisting of the heavy chain amino acid sequence of SEQ ID No. 7 and the light chain amino acid sequence of SEQ ID No. 8), 1T0225 (consisting of the heavy chain amino acid sequence of SEQ ID No. 9 and the light chain amino acid sequence of SEQ ID No. 10), 1T0227 (consisting of the heavy chain amino acid sequence of SEQ ID No. 11 and the light chain amino acid sequence of SEQ ID No. 12), 1T0248 (consisting of the heavy chain amino acid sequence of SEQ ID No. 13 and the light chain amino acid sequence of SEQ ID No. 14), 1T0321 (consisting of the heavy chain amino acid sequence of SEQ ID No. 15 and the light chain amino acid sequence of SEQ ID No. 16), 1T0325 (consisting of the heavy chain amino acid sequence of SEQ ID No. 17 and the light chain amino acid sequence of SEQ ID No. 18), 1T0371 (consisting of the heavy chain amino acid sequence of SEQ ID No. 19 and the light chain amino acid sequence of SEQ ID No. 20), 1T0451 (consisting of the heavy chain amino acid sequence of SEQ ID No. 21 and the light chain amino acid sequence of SEQ ID No. 22), 1T0455 (consisting of the heavy chain amino acid sequence of SEQ ID No. 23 and the light chain amino acid sequence of SEQ ID No. 24), 1T0465 (consisting of the heavy chain amino acid sequence of SEQ ID No. 25 and the light chain amino acid sequence of SEQ ID No. 26), 1T0473 (consisting of the heavy chain amino acid sequence of SEQ ID No. 27 and the light chain amino acid sequence of SEQ ID No. 28), 1T0552 (consisting of the heavy chain amino acid sequence of SEQ ID No. 29 and the light chain amino acid sequence of SEQ ID No. 30), 1T0655 (consisting of the heavy chain amino acid sequence of SEQ ID No. 31 and the light chain amino acid sequence of SEQ ID No. 32), 3T0123 (consisting of the heavy chain amino acid sequence of SEQ ID No. 33 and the light chain amino acid sequence of SEQ ID No. 34), 3T0202 (consisting of the heavy chain amino acid sequence of SEQ ID No. 35 and the light chain amino acid sequence of SEQ ID No. 36), 3T0215 (consisting of the heavy chain amino acid sequence of SEQ ID No. 37 and the light chain amino acid sequence of SEQ ID No. 38), 3T0245 (consisting of the heavy chain amino acid sequence of SEQ ID No. 39 and the light chain amino acid sequence of SEQ ID No. 40), 3T0253 (consisting of the heavy chain amino acid sequence of SEQ ID No. 41 and the light chain amino acid sequence of SEQ ID No. 42), 3T0258 (consisting of the heavy chain amino acid sequence of SEQ ID No. 43 and the light chain amino acid sequence of SEQ ID No. 44), 3T0265 (consisting of the heavy chain amino acid sequence of SEQ ID No. 45 and the light chain amino acid sequence of SEQ ID No. 46), 3T0331 (consisting of the heavy chain amino acid sequence of SEQ ID No. 47 and the light chain amino acid sequence of SEQ ID No. 48), 3T0338 (consisting of the heavy chain amino acid sequence of SEQ ID No. 49 and the light chain amino acid sequence of SEQ ID No. 50), 3T0350 (consisting of the heavy chain amino acid sequence of SEQ ID No. 51 and the light chain amino acid sequence of SEQ ID No. 52), 3T0405 (consisting of the heavy chain amino acid sequence of SEQ ID No. 53 and the light chain amino acid sequence of SEQ ID No. 54), 3T0415 (consisting of the heavy chain amino acid sequence of SEQ ID No. 55 and the light chain amino acid sequence of SEQ ID No. 56), 3T0468 (consisting of the heavy chain amino acid sequence of SEQ ID No. 57 and the light chain amino acid sequence of SEQ ID No. 58), 3T0478 (consisting of the heavy chain amino acid sequence of SEQ ID No. 59 and the light chain amino acid sequence of SEQ ID No. 60), 3T0553 (consisting of the heavy chain amino acid sequence of SEQ ID No. 61 and the light chain amino acid sequence of SEQ ID No. 62), 3T0611 (consisting of the heavy chain amino acid sequence of SEQ ID No. 63 and the light chain amino acid sequence of SEQ ID No. 64), 3T0650 (consisting of the heavy chain amino acid sequence of SEQ ID No. 65 and the light chain amino acid sequence of SEQ ID No. 66), 3T0673 (consisting of the heavy chain amino acid sequence of SEQ ID No. 67 and the light chain amino acid sequence of SEQ ID No. 68), 4m0333 (consisting of the heavy chain amino acid sequence of SEQ ID No. 69 and the light chain amino acid sequence of SEQ ID No. 70), 4m0368 (consisting of the heavy chain amino acid sequence of SEQ ID No. 71 and the light chain amino acid sequence of SEQ ID No. 72), 4m0373 (consisting of the heavy chain amino acid sequence of SEQ ID No. 73 and the light chain amino acid sequence of SEQ ID No. 74), 4T0115 (consisting of the heavy chain amino acid sequence of SEQ ID No. 75 and the light chain amino acid sequence of SEQ ID No. 76), 4T0154 (consisting of the heavy chain amino acid sequence of SEQ ID No. 77 and the light chain amino acid sequence of SEQ ID No. 78), 4T0159 (consisting of the heavy chain amino acid sequence of SEQ ID No. 79 and the light chain amino acid sequence of SEQ ID No. 80), 4T0176 (consisting of the heavy chain amino acid sequence of SEQ ID No. 81 and the light chain amino acid sequence of SEQ ID No. 82), 4T0182 (consisting of the heavy chain amino acid sequence of SEQ ID No. 83 and the light chain amino acid sequence of SEQ ID No. 84), 4T0243 (consisting of the heavy chain amino acid sequence of SEQ ID No. 85 and the light chain amino acid sequence of SEQ ID No. 86), 4T0262 (consisting of the heavy chain amino acid sequence of SEQ ID No. 87 and the light chain amino acid sequence of SEQ ID No. 88), 4T0284 (consisting of the heavy chain amino acid sequence of SEQ ID No. 89 and the light chain amino acid sequence of SEQ ID No. 90), 4T0306 (consisting of the heavy chain amino acid sequence of SEQ ID No. 91 and the light chain amino acid sequence of SEQ ID No. 92), 4T0344 (consisting of the heavy chain amino acid sequence of SEQ ID No. 93 and the light chain amino acid sequence of SEQ ID No. 94), 4T0365 (consisting of the heavy chain amino acid sequence of SEQ ID No. 95 and the light chain amino acid sequence of SEQ ID No. 96), 4T0412 (consisting of the heavy chain amino acid sequence of SEQ ID No. 97 and the light chain amino acid sequence of SEQ ID No. 98), 4T0423 (consisting of the heavy chain amino acid sequence of SEQ ID No. 99 and the light chain amino acid sequence of SEQ ID No. 100), 4T0427 (consisting of the heavy chain amino acid sequence of SEQ ID No. 101 and the light chain amino acid sequence of SEQ ID No. 102), 4T0429 (consisting of the heavy chain amino acid sequence of SEQ ID No. 103 and the light chain amino acid sequence of SEQ ID No. 104), 4T0434 (consisting of the heavy chain amino acid sequence of SEQ ID No. 105 and the light chain amino acid sequence of SEQ ID No. 106), 4T0444 (consisting of the heavy chain amino acid sequence of SEQ ID No. 107 and the light chain amino acid sequence of SEQ ID No. 108), 4T0452 (consisting of the heavy chain amino acid sequence of SEQ ID No. 109 and the light chain amino acid sequence of SEQ ID No. 110), 4T0525 (consisting of the heavy chain amino acid sequence of SEQ ID No. 111 and the light chain amino acid sequence of SEQ ID No. 112), 4T0541 (consisting of the heavy chain amino acid sequence of SEQ ID No. 113 and the light chain amino acid sequence of SEQ ID No. 114), 4T0570 (consisting of the heavy chain amino acid sequence of SEQ ID No. 115 and the light chain amino acid sequence of SEQ ID No. 116), 4T0578 (consisting of the heavy chain amino acid sequence of SEQ ID No. 117 and the light chain amino acid sequence of SEQ ID No. 118), 4T0657 (consisting of the heavy chain amino acid sequence of SEQ ID No. 119 and the light chain amino acid sequence of SEQ ID No. 120), 4T0726 (consisting of the heavy chain amino acid sequence of SEQ ID No. 121 and the light chain amino acid sequence of SEQ ID No. 122), 4T0764 (consisting of the heavy chain amino acid sequence of SEQ ID No. 123 and the light chain amino acid sequence of SEQ ID No. 124), 4T0784 (consisting of the heavy chain amino acid sequence of SEQ ID No. 125 and the light chain amino acid sequence of SEQ ID No. 126), 5T0107 (consisting of the heavy chain amino acid sequence of SEQ ID No. 127 and the light chain amino acid sequence of SEQ ID No. 128), 5T0180 (consisting of the heavy chain amino acid sequence of SEQ ID No. 129 and the light chain amino acid sequence of SEQ ID No. 130), 5T0202 (consisting of the heavy chain amino acid sequence of SEQ ID No. 131 and the light chain amino acid sequence of SEQ ID No. 132), 5T0209 (consisting of the heavy chain amino acid sequence of SEQ ID No. 133 and the light chain amino acid sequence of SEQ ID No. 134), 5T0223 (consisting of the heavy chain amino acid sequence of SEQ ID No. 135 and the light chain amino acid sequence of SEQ ID No. 136), 5T0257 (consisting of the heavy chain amino acid sequence of SEQ ID No. 137 and the light chain amino acid sequence of SEQ ID No. 138), 5T0278 (consisting of the heavy chain amino acid sequence of SEQ ID No. 139 and the light chain amino acid sequence of SEQ ID No. 140), 5T0337 (consisting of the heavy chain amino acid sequence of SEQ ID No. 141 and the light chain amino acid sequence of SEQ ID No. 142), 5T0376 (consisting of the heavy chain amino acid sequence of SEQ ID No. 143 and the light chain amino acid sequence of SEQ ID No. 144), 5T0378 (consisting of the heavy chain amino acid sequence of SEQ ID No. 145 and the light chain amino acid sequence of SEQ ID No. 146), 5T0404 (consisting of the heavy chain amino acid sequence of SEQ ID No. 147 and the light chain amino acid sequence of SEQ ID No. 148), 5T0406 (consisting of the heavy chain amino acid sequence of SEQ ID No. 149 and the light chain amino acid sequence of SEQ ID No. 150), 5T0420 (consisting of the heavy chain amino acid sequence of SEQ ID No. 151 and the light chain amino acid sequence of SEQ ID No. 152), 5T0451 (consisting of the heavy chain amino acid sequence of SEQ ID No. 153 and the light chain amino acid sequence of SEQ ID No. 154), 5T0465 (consisting of the heavy chain amino acid sequence of SEQ ID No. 155 and the light chain amino acid sequence of SEQ ID No. 156), more preferably of one antibody from the group comprising 1T0325, 1T0451, 1T0473, 1T0655, 3T0123, 3T0253, 3T0553, 4T0243, 4T0306, 4T0570, 4T0726, 4T0764, 4T0784, 5T0180, 5T0223, 5T0278, 5T0337, 5T0451.

According to another preferred embodiment of the second aspect of the present invention, the antibody or binding fragment thereof comprises the combination of the heavy chain and the light chain of one antibody selected from the group comprising 1T0129 (SEQ ID No. 1 and 2), 1T0139 (SEQ ID No. 3 and 4), 1T0201 (SEQ ID No. 5 and 6),1T0221 (SEQ ID No. 7 and 8), 1T0225 (SEQ ID No. 9 and 10), 1T0227 (SEQ ID No. 11 and 12), 1T0248 (SEQ ID No. 13 and 14), 1T0321 (SEQ ID No. 15 and 16), 1T0325 (SEQ ID No. 17 and 18), 1T0371 (SEQ ID No. 19 and 20), 1T0451 (SEQ ID No. 21 and 22), 1T0455 (SEQ ID No. 23 and 24), 1T0465 (SEQ ID No. 25 and 26), 1T0473 (SEQ ID No. 27 and 28), 1T0552 (SEQ ID No. 29 and 30), 1T0655 (SEQ ID No. 31 and 32), 3T0123 (SEQ ID No. 33 and 34), 3T0202 (SEQ ID No. 35 and 36), 3T0215 (SEQ ID No. 37 and 38), 3T0245 (SEQ ID No. 39 and 40), 3T0253 (SEQ ID No. 41 and 42), 3T0258 (SEQ ID No. 43 and 44), 3T0265 (SEQ ID No. 45 and 46), 3T0331 (SEQ ID No. 47 and 48), 3T0338 (SEQ ID No. 49 and 50), 3T0350 (SEQ ID No. 51 and 52), 3T0405 (SEQ ID No. 53 and 54), 3T0415 (SEQ ID No. 55 and 56), 3T0468 (SEQ ID No. 57 and 58), 3T0478 (SEQ ID No. 59 and 60), 3T0553 (SEQ ID No. 61 and 62), 3T0611 (SEQ ID No. 63 and 64), 3T0650 (SEQ ID No. 65 and 66), 3T0673 (SEQ ID No. 67 and 68), 4m0333 (SEQ ID No. 69 and 70), 4m0368 (SEQ ID No. 71 and 72), 4m0373 (SEQ ID No. 73 and 74), 4T0115 (SEQ ID No. 75 and 76), 4T0154 (SEQ ID No. 77 and 78), 4T0159 (SEQ ID No. 79 and 80), 4T0176 (SEQ ID No. 81 and 82), 4T0182 (SEQ ID No. 83 and 84), 4T0243 (SEQ ID No. 85 and 86), 4T0262 (SEQ ID No. 87 and 88), 4T0284 (SEQ ID No. 89 and 90), 4T0306 (SEQ ID No. 91 and 92), 4T0344 (SEQ ID No. 93 and 94), 4T0365 (SEQ ID No. 95 and 96), 4T0412 (SEQ ID No. 97 and 98), 4T0423 (SEQ ID No. 99 and 100), 4T0427 (SEQ ID No. 101 and 102), 4T0429 (SEQ ID No. 103 and 104), 4T0434 (SEQ ID No. 105 and 106), 4T0444 (SEQ ID No. 107 and 108), 4T0452 (SEQ ID No. 109 and 110), 4T0525 (SEQ ID No. 111 and 112), 4T0541 (SEQ ID No. 113 and 114), 4T0570 (SEQ ID No. 115 and 116), 4T0578 (SEQ ID No. 117 and 118), 4T0657 (SEQ ID No. 119 and 120), 4T0726 (SEQ ID No. 121 and 122), 4T0764 (SEQ ID No. 123 and 124), 4T0784 (SEQ ID No. 125 and 126), 5T0107 (SEQ ID No. 127 and 128), 5T0180 (SEQ ID No. 129 and 130), 5T0202 (SEQ ID No. 131 and 132), 5T0209 (SEQ ID No. 133 and 134), 5T0223 (SEQ ID No. 135 and 136), 5T0257 (SEQ ID No. 137 and 138), 5T0278 (SEQ ID No. 139 and 140), 5T0337 (SEQ ID No. 141 and 142), 5T0376 (SEQ ID No. 143 and 144), 5T0378 (SEQ ID No. 145 and 146), 5T0404 (SEQ ID No. 147 and 148), 5T0406 (SEQ ID No. 149 and 150), 5T0420 (SEQ ID No. 151 and 152), 5T0451 (SEQ ID No. 153 and 154), 5T0465 (SEQ ID No. 155 and 156), more preferably of one antibody from the group comprising 1T0325, 1T0451, 1T0473, 1T0655, 3T0123, 3T0253, 3T0553, 4T0243, 4T0306, 4T0570, 4T0726, 4T0764, 4T0784, 5T0180, 5T0223, 5T0278, 5T0337, 5T0451.

According to one preferred embodiment of the second aspect of the present invention, the antibody or binding fragment thereof comprises the heavy chain CDR1 to CDR3 and the light chain CDR1 to CDR3 amino acid sequence of one of the antibodies selected from 3T0331 (consisting of the heavy chain amino acid sequence of SEQ ID No. 47 and the light chain amino acid sequence of SEQ ID No. 48) or 4T0243 (consisting of the heavy chain amino acid sequence of SEQ ID No. 85 and the light chain amino acid sequence of SEQ ID No. 86), more preferably of antibody 3T0331.

According to a preferred embodiment of the second aspect of the present invention, the antibody or binding fragment thereof comprises the combination of the heavy chain and the light chain of one of the antibodies selected from 3T0331 (SEQ ID No. 47 and 48) or 4T0243 (SEQ ID No. 85 and 86), more preferably of 3T0331.

According to the third aspect of the present invention, a pharmaceutical composition is provided comprising a monoclonal human antibody or binding fragment thereof according to the second aspect of the present invention, and at least one pharmaceutically acceptable excipient.

According to a preferred embodiment of the third aspect of the present invention, the pharmaceutical composition is a vaccination composition for a human subject.

According to the fourth aspect of the present invention, a kit is provided comprising a monoclonal human antibody or binding fragment thereof according to the second aspect of the present invention, and a container.

According to the fifth aspect of the present invention, a monoclonal human antibody or binding fragment thereof according to the second aspect of the invention, a pharmaceutical composition according to the third aspect of the invention, or a kit according to the fourth aspect of the invention are provided for use as a medicament, preferably for use as a vaccine.

According to the sixth aspect of the present invention, a monoclonal human antibody or binding fragment thereof according to the second aspect of the invention, a pharmaceutical composition according to the third aspect of the invention, or a kit according to the fourth aspect of the invention are provided for use in the treatment or prevention of a disease caused by the infectious pathogen in human subjects, preferably for use in the treatment or prevention of *Ebolavirus*-caused disease in human subjects.

According to another aspect of the present invention, a method is provided for obtaining human antibodies directed against an infectious pathogen, wherein the method comprises identifying in an isolate taken from a human subject previously vaccinated with a vaccine comprising an antigenic protein derived from the infectious pathogen, wherein the isolate is an isolate of B lymphocytes exhibiting antibodies directed against the infectious pathogen on their cell surface and/or antibodies directed against the infectious pathogen from vaccinated subjects, those B lymphocytes expressing antibodies directed against the infectious pathogen and/or antibodies directed against the infectious pathogen, preferably on a single cell- or single antibody-basis, and expressing monoclonal antibodies directed against the infectious pathogen. According to a preferred embodiment of this aspect, the method is carried out in vitro.

DETAILED DESCRIPTION OF THE INVENTION

The present inventors have dedicated themselves to solving the problem of the present invention and were successful to find a novel method for obtaining human monoclonal antibodies against infectious pathogens, in particular against the Ebola virus, which overcomes the disadvantages of the prior art strategies, and were further successful in providing novel and useful human monoclonal antibodies against the Ebola virus that have been obtained by said method.

When setting out to make the present invention, the present inventors have initially analysed serum samples of subjects vaccinated with a vaccine against Ebola virus. These serum samples of vaccinated patients have then been compared against serum samples of surviving Ebola patients with regard to serum reactivity and binding to the EBOV glycoprotein in ELISAs.

Figure 1:
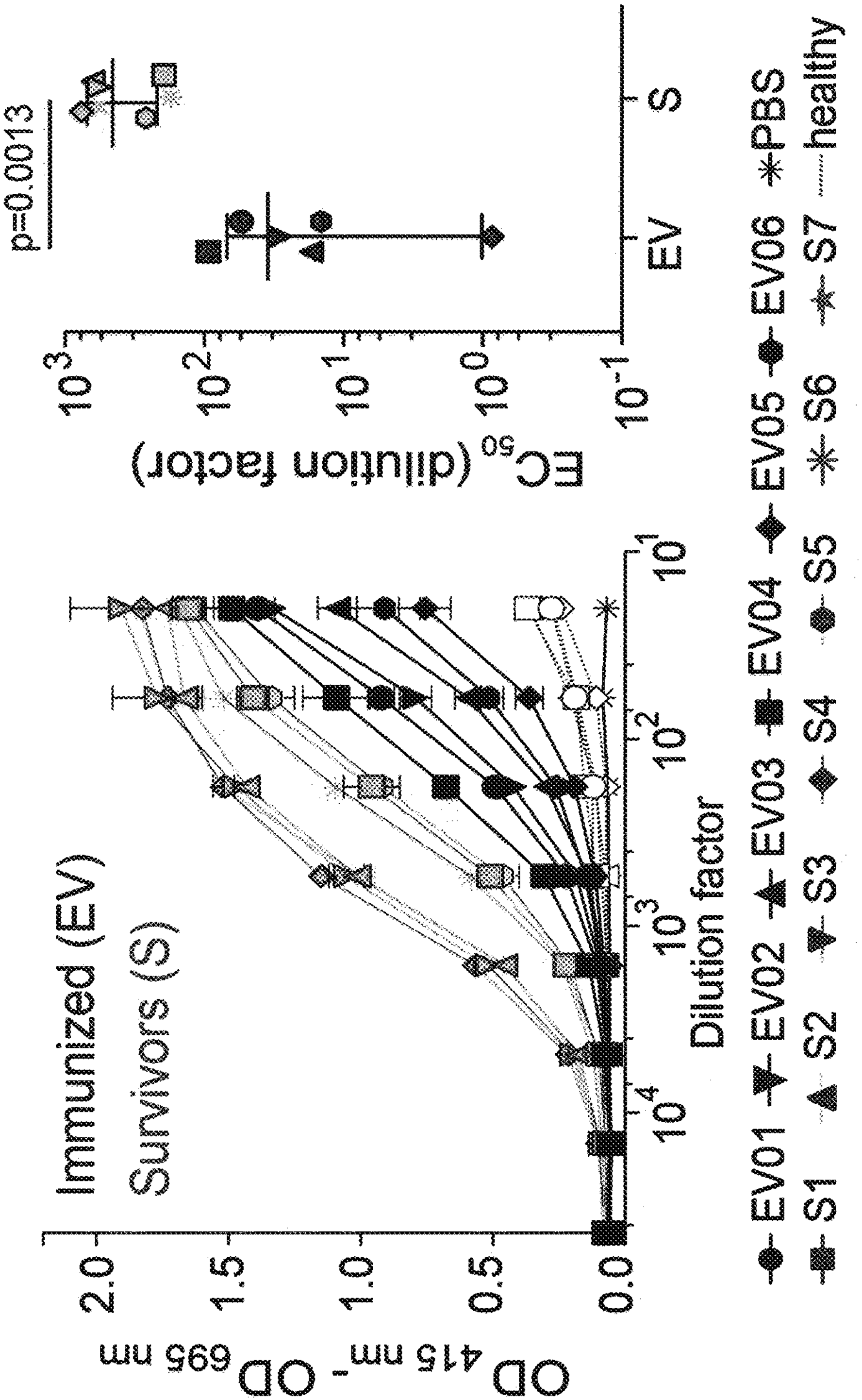
FIG. 1 shows a comparison of serum reactivity of survivors and vaccinated individuals. For this serum reactivity to EBOV GPΔTM (Makona) measured by ELISA in rVSV-ZEBOV-immunized subjects (black) is compared to EVD survivors (S1-S7, gray, left panel). Error bars show standard deviation (SD) of means of technical duplicates. Lines indicate means of calculated $EC_{50}$ dilution factors, which are 35 and 456 for vaccines and survivors, respectively (n=6 [EV] and 7 [S] independent samples, p=0.0013, right panel). PBS and healthy serum samples were used as negative controls. Significance was tested by a two-tailed unpaired t-test.

Interestingly, serum samples of vaccinated subjects showed a significantly lower activity in comparison to serum samples of survivors (FIG. 1). This finding initially pointed away from any expectation of success in finding novel and useful monoclonal antibodies directed against Ebola virus in vaccinated individuals and would have pointed to rather employing disease survivors as antibody sources instead.

Nevertheless, the present inventors proceeded with their approach and successfully completed the invention of a novel and useful method for obtaining human monoclonal antibodies against infectious pathogens, in particular against Ebola virus, and of novel and useful monoclonal, human antibodies against such infectious pathogens.

Figure 2:
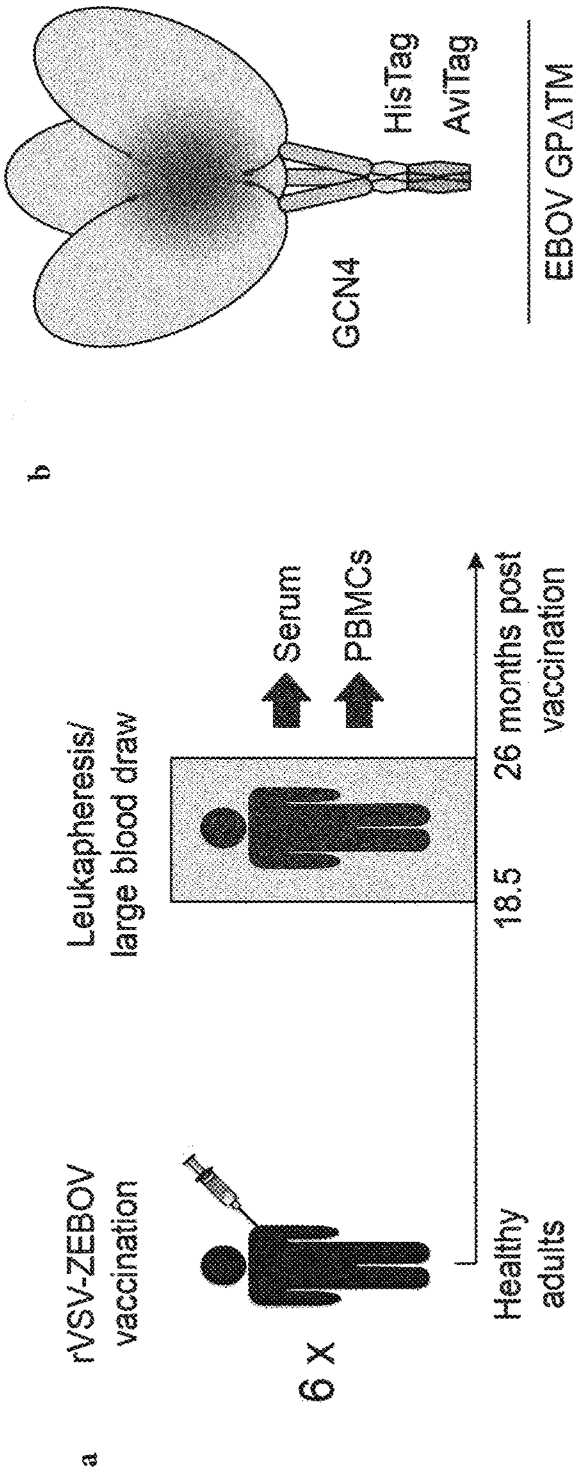
FIG. 2 shows a schematic overview of the sample collection as well as the schematic structure of the EBOV GP used for B lymphocyte sorting, wherein according to (a) sample collection from rVSV-ZEBOV-immunized donors (EV01-EV06) was performed between 18.5 to 26 months after single dose vaccination. Serum was collected and PBMC samples were obtained after leukapheresis or large blood draw. Part (b) shows the design of EBOV GPΔTM construct with GCN4 trimerization domain, His- and Avi-Tag, as well as covalent labeling with fluorophore DyLight 488 (dark gray).

Thus, the present invention provides a method for obtaining human antibodies directed against an infectious pathogen, wherein the method comprises vaccination of a human subject with a vaccine comprising an antigenic protein derived from the infectious pathogen (FIG. 2), preferably an antigenic protein ordinarily expressed on the surface of the infectious pathogen, isolating B lymphocytes exhibiting antibodies directed against the infectious pathogen on their cell surface and/or antibodies directed against the infectious pathogen from vaccinated subjects (FIG. 3), identifying B lymphocytes expressing antibodies directed against the infectious pathogen and/or antibodies directed against the infectious pathogen, preferably on a single cell- or single antibody-basis, and expressing monoclonal antibodies directed against the infectious pathogen.

Figure 4:
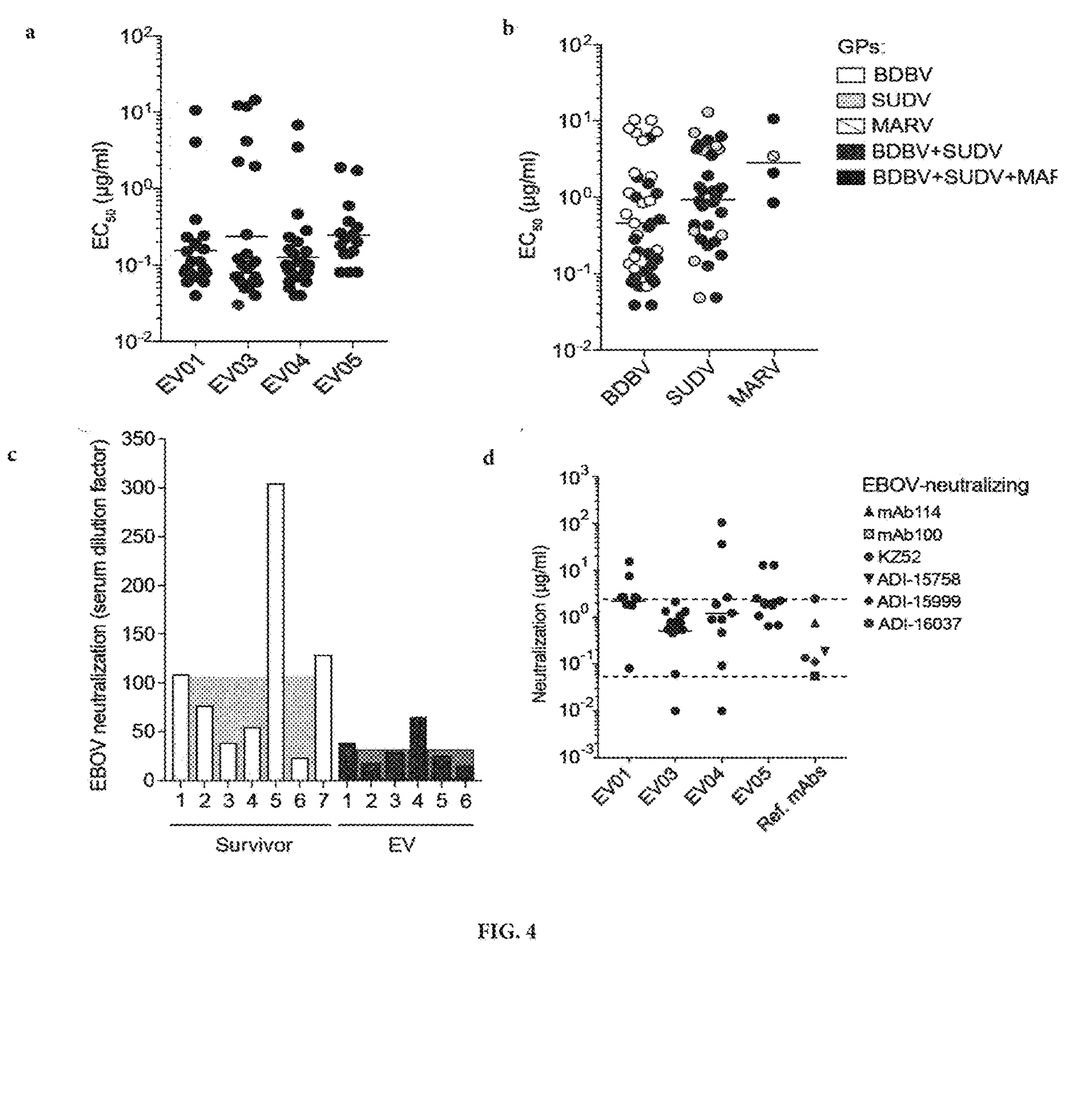
FIG. 4 shows the binding activity and cross-reactivity of antibodies isolated from vaccinated individuals as well as their ability to neutralize EBOV. (a) ELISA binding analysis of mAbs isolated from rVSV-ZEBOV-vaccinated individuals (EV01, EV03-EV05) against EBOV GPΔTM. Shown are $EC_{50}$ values of binding mAbs [n=21 (EV01), 23 (EV03), 29 (EV04) and 16 (EV05)]. (b) $EC_{50}$ values [n=42 (BDBV), 32 (SUDV) and 4 (MARV) of EBOV GPΔTM-specific mAbs with cross-reactivity against GPs from different filoviruses determined by ELISA. mAbs specific for GPs of EBOV plus one other filovirus are shown in white or light gray colors and mAbs specific for GPs of EBOV plus 2 or 3 other filovirus species are shown in dark gray or black, respectively. (a-b) Means are indicated by lines. (c) Analysis of serum neutralizing activity of EVD survivors (light gray) and rVSV-ZEBOV-immunized donors (EV; black). Shown are dilution factors yielding full neutralization of EBOV Mayinga. Colored background areas indicate means. Significance was tested by two-tailed unpaired t-test (n=7 (survivor) and n=6 (EV) biologically independent samples, p=0.089). (d) Antibody concentrations (μg/mL) required to achieve full neutralization. mAbs obtained from rVSV-ZEBOV-immunized subjects [dark gray; n=9 (EV01), 14 (EV03), 10 (EV04), 9 (EV05)] compared to published antibodies (light gray; KZ52, mAb114, mAb100, ADI-15758, ADI-15999, and ADI-16037). Background area illustrates neutralization range of reference antibodies. Means are indicated by lines. Neutralization experiments were performed in quadruplicates.

Preferably within the present invention, the antibodies directed against an infectious pathogen are directed against a virus. More preferably, the antibodies are directed against a virus from the family Filoviridae, even more preferably against a virus from the genus *Ebolavirus* or *Marburgvirus*, particularly preferably from the genus *Ebolavirus* (FIGS. 4*a* and *b*).

According to a preferred embodiment, an antibody directed against an infectious pathogen means an antibody binding to the infectious pathogen, or a protein or proteinaceous component of the infectious pathogen with an at least 10-fold, more preferably at least 50-fold, particularly preferably at least 100-fold increased affinity compared to unrelated infectious pathogens, proteins or proteinaceous components thereof.

According to another preferred embodiment, an antibody directed against an infectious pathogen means an antibody binding to an epitope of the infectious pathogen with an at least 10-fold, more preferably at least 50-fold, particularly preferably more at least 100-fold increased affinity compared to epitopes of unrelated infectious pathogens. Within the context of the above, unrelated infectious pathogens mean infectious pathogens from a different family or higher taxonomic rank.

In a preferred embodiment of the present invention, the vaccination of a human subject is an intentional vaccination. This vaccination may be carried out according to established principles for vaccinating human patients, as for example described in Vaccines (Eds. Plotkin, S. A., et al., 7$^{th}$ Edition, Elsevier Health Sciences Division, 2017, ISBN 978-0-323-35761-6).

The vaccination of a human subject is carried out with a vaccine comprising an antigenic protein derived from the infectious pathogen. Such antigenic protein will serve as an immunogen for the generation of autologous antibodies by the immune system of the vaccinated subject. With the aim of obtaining antibodies, which are most suitable for administration to human patients, production and isolation of human antibodies is clearly advantageous to generation of antibodies in other species. Advantages of such antibodies may include increased longevity, long half-life after being administered to the subject, no or minor side effects and other desirable properties.

According to a preferred embodiment, the antigenic protein derived from the infectious pathogen is ordinarily expressed on the surface of the infectious pathogen. In the context of the present invention, an antigenic protein being ordinarily expressed on the surface of the infectious pathogen means a protein which is expressed in this way when being in its natural environment and part of the infectious pathogen as it occurs in nature.

For the sake of being used for vaccination of a human subject, the antigenic protein may preferably be present in the vaccine as part of an attenuated virus different from the infectious pathogen. In this way, the antigenic protein can be presented to the patient in order to provoke an immune response without the apparent risk of causing unwanted or dangerous disease symptoms. More preferably, the antigenic protein may be part of an attenuated recombinant vesicular stomatitis virus.

According to one preferred embodiment, the antigenic protein derived from the infectious pathogen as used in the method of the invention is an *Ebolavirus* glycoprotein, more preferably the envelope glycoprotein of the Zaire *Ebolavirus* (strain Kikwit-95) having the UniProt accession number P87666. Alternatively preferably, proteins of other infectious pathogens may be integrated in a heterologous carrier to be used as vaccines for human subjects.

In the case of viruses as infectious pathogens, it may be preferable to use an envelope glycoprotein of the infectious pathogen and introduce it into a heterologous virus as a replacement for the proprietary envelope glycoprotein of the carrier virus. In particular, it is preferred that an envelope glycoprotein of a virus as the infectious pathogen is used as replacement for the envelope glycoprotein (UniProt accession number P03522) of the attenuated recombinant vesicular stomatitis virus used as carrier virus.

In a particularly preferred embodiment of the present invention, the vaccine comprises rVSV-ZEBOV. This vaccine has previously been used to vaccinate patients at risk of developing EVD symptoms and is described inter alia in Monath, T P et al. Vaccine: X, Volume 1, 2019, 100009, ISSN 2590-1362, and the references cited therein. To date, more than 180,000 people have been actively immunized using this vaccine and could serve as potential sources for obtaining monoclonal, human antibodies using the method of the present invention.

Figure 3:
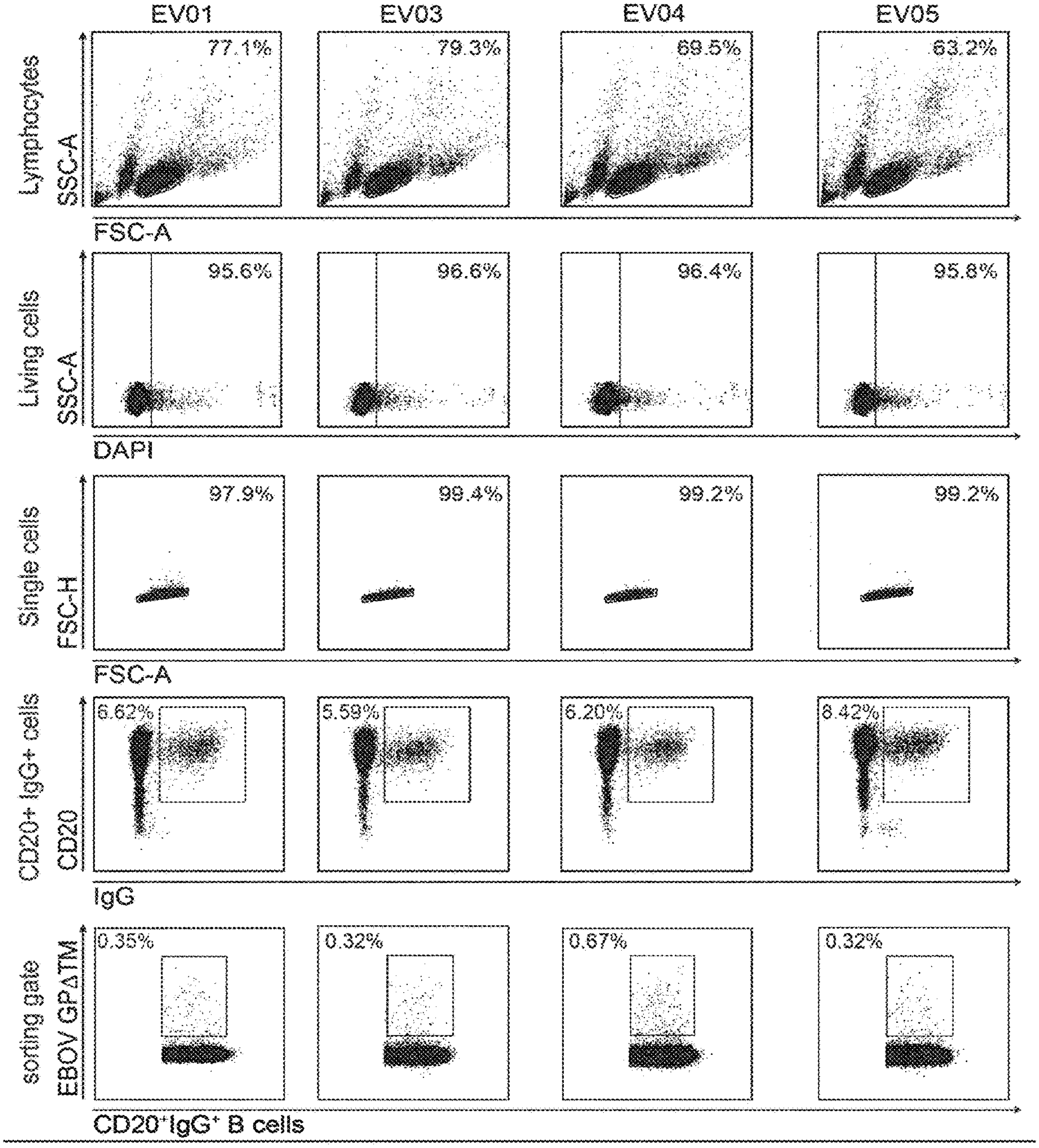
FIG. 3 shows the gating strategy for flow cytometric analysis and B lymphocyte sorting. CD19-enriched (MACS) PBMCs of rVSV-ZEBOV-vaccinated donors (EV01, EV03-EV05) were gated for lymphocytes→live cells→single cells. $CD20^{+}IgG^{+}$ B lymphocytes were selected for sort of EBOV-specific B lymphocytes. One of two independent experiments with similar results is shown.

The method of the present invention further involves a step of isolating B lymphocytes exhibiting antibodies directed against the infectious pathogen on their cell surface from vaccinated subjects and/or isolating antibodies directed against the infectious pathogen from vaccinated subjects (FIG. 3). Preferably, this step is a step of isolating B lymphocytes exhibiting antibodies directed against the infectious pathogen on their cell surface from vaccinated subjects. More preferably, this step involves collecting peripheral blood mononuclear cells (PBMC) from vaccinated individuals as an initial separation step.

According to a preferred embodiment, peripheral blood mononuclear cells (PBMC) are enriched for B lymphocytes, preferably by enrichment of B lymphocytes via magnetic cell separation (MACS), more preferably by use of magnetic cell separation (MACS) using CD19-microbeads. According to another preferred embodiment, B lymphocytes of the vaccinated subject are subjected to serial limiting dilutions which is followed by identification of B lymphocytes expressing antibodies directed against the infectious pathogen. Preferably, serial limiting dilutions are carried out to statistically obtain not more than three cells per well upon plating, more preferably not more than two cells per well upon plating, particularly preferably a single cell per well upon plating. Also preferably, a step of identifying the B lymphocytes obtained or the antibodies secreted by said lymphocytes is carried out following the serial limiting dilutions.

According to one preferred embodiment, the step of isolating B lymphocytes exhibiting antibodies directed against the infectious pathogen on their cell surface comprises contacting the extracted B lymphocytes with a component of the infectious pathogen to allow selective sorting of the B lymphocytes of interest from the extracted B lymphocytes. Preferably, selective sorting of the B lymphocytes of interest comprises fluorescence-activated cell sorting (FACS), magnetic-activated cell sorting (MACS) or chromatographic separation.

According to a preferred embodiment of the present invention, the step of isolating B lymphocytes may further comprise contacting the cells with additional markers to allow selective sorting of $CD20^+$ and/or $IgG^+$ cells (FIG. 3). According to one preferred embodiment, B lymphocytes exhibiting antibodies directed against the infectious pathogen on their cell surface are isolated from vaccinated subjects by contacting the extracted B lymphocytes with a component of the infectious pathogen labelled with a fluorescence marker, and isolating the B lymphocytes of interest by fluorescence-activated cell sorting (FACS) (FIG. 3).

Preferably therein, the B lymphocytes are contacted with components of the infectious pathogen ordinarily expressed on the surface of the infectious pathogen, more preferably envelope glycoproteins of viruses lacking the transmembrane domain. In preferable embodiments of the invention relating to *Ebolavirus*, the B lymphocytes are contacted with *Ebolavirus* glycoprotein lacking the transmembrane domain, more preferably with recombinant *Ebolavirus* GP constructs lacking the transmembrane domain residues 651-676.

According to a particularly preferred embodiment, the B lymphocytes are contacted with a protein of SEQ ID No. 158 (peptide sequence of EBOV GPΔTM), alternatively preferably by a protein encoded by SEQ ID No. 157 (nucleotide sequence of EBOV GPΔTM). The construct EBOV GPΔTM which displays the envelope protein of Ebola virus for binding to antibodies specific for said protein is able to selectively associate with antibodies directed against Ebola virus. Since EBOV GPΔTM further comprises a fluorescent marker, the step of contacting allows selective marking of specific antibodies for fluorescence-activated cell sorting (FACS).

Within the context of the present invention, it is also well possible to use other components of infectious pathogens which are bound by specific antibodies extracted from vaccinated human subjects in a selective manner. Also, other markers aside from the fluorescent marker employed in EBOV GPΔTM are also encompassed by the present invention to be fused to components of infectious pathogens, be it other fluorescent markers or specifically binding molecules which allow specific sorting by other methods.

According to a preferred embodiment of the present invention, the step of identifying B lymphocytes exhibiting antibodies directed against the infectious pathogen on their cell surface and/or antibodies directed against the infectious pathogen comprises amplifying nucleotide sequences coding for light and heavy chains of each individual antibody and sequencing the amplified nucleotide sequences of said light and heavy chains.

According to one preferred embodiment, the step of identifying B lymphocytes of interest comprises carrying out single cell PCR, more preferably using sequential, semi-nested PCRs. Single cell PCR may preferably be carried out as previously described by Tiller, T. et al. *Journal of Immunological Methods,* 329, 112-124 (2008). or by von Boehmer, L. et al. *Nat Protoc* 11, 1908-1923 (2016).

Preferably, after the nucleotide sequences coding for the light and heavy chains have been sequenced and identified, a step of expressing each monoclonal antibody directed against the infectious pathogen is carried out which comprises cloning of the light and heavy chain nucleotide sequences into a mAb expression vector, more preferably using sequence- and ligation-independent cloning (SLIC) as previously described by by von Boehmer, L. et al. *Nat Protoc* 11, 1908-1923 (2016).

Furthermore, the resulting plasmids are preferably transfected into suitable host cells, more preferably into HEK293E cells. Transfected cells are then preferably cultured in selective media to select for successfully transfected cells. The supernatant of said cells are preferably collected and antibodies were isolated from the supernatant, preferably by using protein G sepharose.

According to the present invention, the step of isolating B lymphocytes exhibiting antibodies directed against the infectious pathogen on their cell surface may also be understood as isolating a population of B lymphocytes including such B lymphocytes from the vaccinated subject. Further preferably, the method for obtaining human antibodies according to the present invention should be carried out by performing steps a), b), c) and d) in this order.

According to the the second aspect of the present invention, a monoclonal human antibody or binding fragment thereof is provided which is directed against an infectious pathogen, wherein the human antibody is preferably obtained by the method according to the first aspect of the present invention.

As already laid out above, monoclonal antibodies of human origin are difficult to obtain by using the standard immunological toolkit. Antibody sources for the production of monoclonal antibodies are limited and isolation and identification of specifically binding antibodies which neutralize Ebola virus are challenging. Therefore, it would have been a very high burden for the skilled person to identify and generate additional antibodies able to neutralize Ebola virus.

The present inventors however succeeded in this task and herewith provide novel antibodies which neutralize Ebola virus and other infectious pathogens with unexpected properties. These antibodies have been obtained by the method of the present invention.

Within the context of the present invention, the antibodies, which have been generated and described herein, may be used and claimed as the complete monoclonal human antibody or as any functional or binding fragment thereof. Preferably, the monoclonal human antibody or any kind of functional or binding fragment thereof should comprise the complementarity determining regions (CDR) 1 to 3 of the heavy chain and of the light chain of the human monoclonal antibody.

The CDR regions of the antibody sequences described herein are preferably defined according to the numbering scheme of IMGT which is an adaptation of the numbering scheme of Chothia (ImMunoGeneTics information system; Lefranc et al., NAR 27:209-212 (1999);).

In one preferred embodiment, the antibody is a monoclonal antibody or a fragment thereof that retains binding specificity and ability to neutralize infectious pathogen. In one preferred embodiment, the antibody is an IgG1, IgG2, IgG3, or IgG4 antibody. For example, the antibody may be an antibody comprising an Fc domain of any human IgG isotype (e.g. IgG1, IgG2, IgG3, or IgG4).

Optionally, the antigen-binding compound consists of or comprises a Fab, Fab', Fab'-SH, $F(ab)_2$, Fv, a diabody, single-chain antibody fragment, or a multispecific antibody comprising multiple different antibody fragments.

According to a preferred embodiment, the monoclonal antibody or binding fragment thereof directed against an infectious pathogen is directed against a virus from the family Filoviridae, more preferably from the genus *Ebolavirus* or *Marburgvirus*, particularly preferably from the genus *Ebolavirus* (FIGS. 4*a* and *b*).

According to one preferred embodiment, the monoclonal human antibody or binding fragment thereof exhibits cross-reactivity against a broad range of infectious pathogens, more preferably against a range of infectious pathogens within the same species, even more preferably within the same genus, particularly preferably within the same family (FIG. 4*b*).

According to one specific preferred embodiment, the monoclonal human antibody or binding fragment thereof exhibits reactivity with more than one virus from the family Filoviridae, preferably with at least two selected from the group comprising Bundibugyo virus, Marburg virus, Sudan virus, and Zaire *Ebolavirus*. Antibodies which exhibit such reactivity are antibodies 1T0129, 1T0221, 1T0225, 1T0321, 1T0325, 1T0371, 1T0451, 1T0465, 1T0473, 1T0552, 1T0655, 3T0123, 3T0215, 3T0253, 3T0350, 3T0405, 3T0415, 3T0553, 4m0333, 4m0373, 4T0115, 4T0154, 4T0159, 4T0176, 4T0182, 4T0243, 4T0262, 4T0284, 4T0306, 4T0344, 4T0365, 4T0412, 4T0423, 4T0427, 4T0434, 4T0525, 4T0541, 4T0570, 4T0657, 4T0726, 4T0764, 4T0784, 5T0107, 5T0180, 5T0223, 5T0257, 5T0278, 5T0337, 5T0378, 5T0404, 5T0406, 5T0420 and 5T0451.

Figure 5:
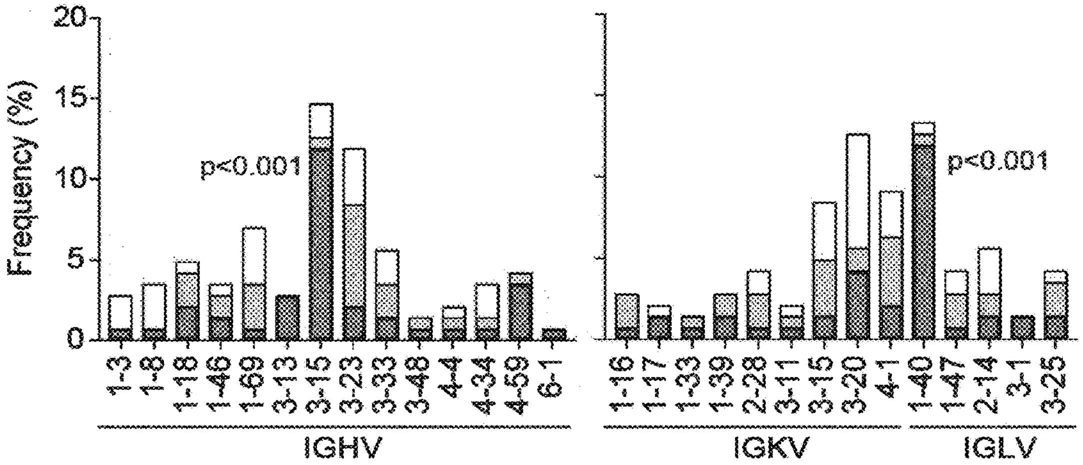
FIG. 5 shows the importance of the monoclonal antibodies with the V gene combination of IGHV3-15 and IGLV1-40 for the EBOV neutralization activity in the vaccinated individuals. (a) Frequency of heavy chain (left) and light chain (right) V genes in rVSV-ZEBOV-induced antibodies that neutralize EBOV Mayinga (dark gray), bind (light gray) or do not bind EBOV GPΔTM (white; n=143). Shown are V genes with at least one neutralizing antibody. Significant changes in V gene frequency of neutralizing antibodies were tested using a binominal test under the null hypothesis of equal frequency, α=0.05, and Bonferroni correction. Only IGHV3-15 and IGLV1-40 increases were highly significant with $p=2.2\times10^{-9}$. (b) Frequency of neutralizing IGHV3-15-carrying antibodies. Slices represent antibodies of unrelated clones from individual donors (left) and corresponding light chains (right).
Figure 5:
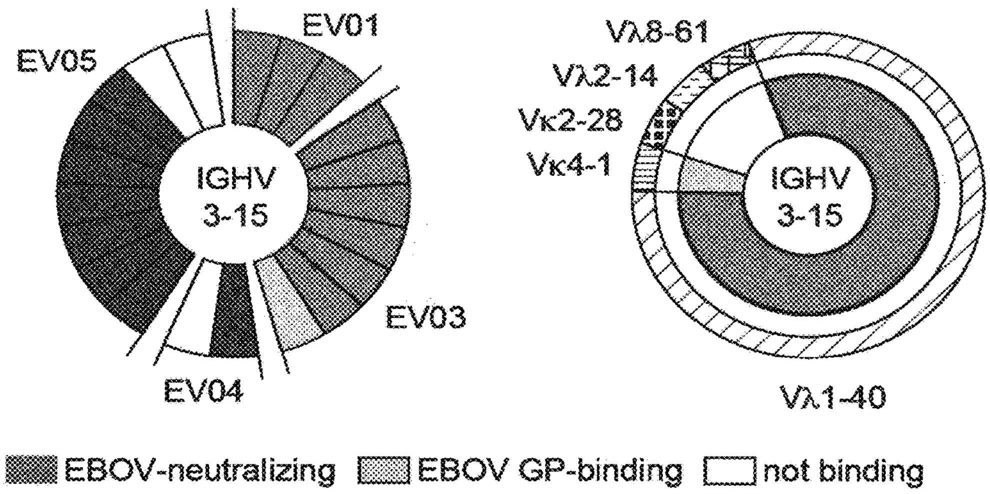

According to another preferred embodiment, the monoclonal human antibody comprises an amino acid sequence encoded by the heavy chain V gene segment IGHV3-15 or an amino acid sequence being at least 80% identical thereto, and an amino acid sequence encoded by the light chain V gene segment IGLV1-40 or an amino acid sequence being at least 80% identical thereto (FIG. 5). Antibodies, which are exhibiting such a distinct combination of V gene segments and successfully neutralize Ebola virus are 1T0201, 1T0227, 1T0455, 3T0245, 3T0253, 3T0265, 3T0338, 3T0650, 3T0673, 4T0452, 5T0180, 5T0202, 5T0209, 5T0223, 5T0278, 5T0337 and 5T0451.

It was surprising to find that a high percentage of the antibodies which were identified as potent neutralizers to the Ebola virus possess the combination of the heavy chain V gene segment IGHV3-15 and the light chain V gene segment IGLV1-40 (FIG. 5). It appears as if this combination alone may be suitable to act as Ebola virus neutralizing antibody. Small variations and mutations of the sequence of the antibody may be tolerated without negatively influencing the activity of the claimed antibodies. Thus, amino acid sequences of the antibodies described herein are considered to be encompassed by the present invention as long as they exhibit an identity ratio of 80% to the disclosed sequences.

The determination of percent identity between two sequences is accomplished according to the present invention by using the mathematical algorithm of Karlin and Altschul (Proc. Natl. Acad. Sci. USA (1993) 90: 5873-5877). Such an algorithm is the basis of the BLASTN and BLASTP programs of Altschul et al. (J. Mol. Biol. (1990) 215: 403-410). BLAST nucleotide searches are performed with the BLASTN program. To obtain gapped alignments for comparative purposes, Gapped BLAST is utilized as described by Altschul et al. (Nucleic Acids Res. (1997) 25: 3389-3402). When utilizing BLAST and Gapped BLAST programs, the default parameters of the respective programs are used.

According to a preferred embodiment of the present invention, amino acid sequences form part of the invention which consist of or comprise a nucleic acid sequence being at least 85% identical to the individualized aptamer sequences which are disclosed herein, more preferably at least 90% identical, even more preferred at least 95% identical.

According to another preferred embodiment, the monoclonal human antibody or binding fragment thereof exhibits neutralization of *Ebolavirus* in a neutralization assay at a concentration of 15 μg/mL or less, preferably at 5 μg/mL or less, more preferably at 0.1 μg/mL or less, even more preferably at 0.05 μg/mL or less (FIGS. 4*c* and *d*).

The neutralization assay to be used for determining the values given above is carried out as follows:

Antibodies (starting at a concentration of 100 μg/ml [antibodies]) were serially diluted in 96-well culture plates in Dulbecco's Modified Eagle's Medium (DMEM, Thermo Fisher Scientific) supplemented with 2% fetal calf serum, penicillin (50 units/m1), streptomycin (50 μg/ml) and L-glutamine (2 mM).

100 $TCID_{50}$ units of EBOV Mayinga (GenBank: NC_002549) and SUDV Boniface (GenBank: FJ968794.1) were added to the serum or antibody dilutions. Following incubation at 37° C. for 1 hour, Vero C1008 cells (ATCC® CRL-1586™; 10,000 cells per well) were added. Plates were then incubated at 37° C. with 5% $CO_2$ and cytopathic effects (CPE) were evaluated at day 7 post infection as previously reported in Cutts et al. *Scientific Reports* (2019) 9:6590 | https://doi.org/10.1038/s41598-019-42386-5.

Neutralization may be defined as visibly recognizable reduction of CPE in serum or antibody dilutions compared to positive controls. Neutralization titers were calculated of four replicates as geometric mean concentrations in the case of monoclonal antibodies (GMC). The cut-off of the assay is determined by the first dilution of the respective serum or antibody.

According to one preferred embodiment, the concentrations of antibody required for neutralization mean the concentrations used on 100 $TCID_{50}$ units of a virus which prevents development of cytopathic effects of the virus on human or NHP cells. According to a specific embodiment, side-by-side comparison of the neutralization assay may be carried out with positive and negative controls to determine neutralization.

Antibodies which exhibit neutralization at a concentration of more than 15 μg/mL in the neutralization assay described above are 1T0130 and 1T0221, antibodies which exhibit neutralization at a concentration of 15 μg/mL or less and more than 5 μg/mL are 1T0139, 5T0180, 5T0376 and 1T0248, antibodies which exhibit neutralization at a concentration of 5 μg/mL or less and more than 0.1 μg/mL are 4m0368, 3T0265, 4T0578, 3T0123, 3T0202, 3T0673, 3T0245, 5T0278, 5T0465, 3T0650, 3T0478, 3T0611, 4T0452, 4T0764, 5T0451, 3T0338, 4T0444, 3T0253, 3T0553, 1T0455, 5T0209, 1T0227, 4T0784, 5T0223, 3T0468, 5T0337, 1T0451, 5T0202, 4T0726, 1T0201, 1T0325 and 1T0473, antibodies which exhibit neutralization at a concentration of 0.1 μg/mL or less and more than 0.05 μg/mL are 3T0258, 1T0655, 4T0570, antibodies which exhibit neutralization at a concentration of 0.05 μg/mL or less are 3T0331 and 4T0243.

As examined in the neutralization assay, it could be experimentally verified that the following antibodies show neutralization at the following concentrations: 3T0331 (0.011 μg/mL), 4T0243 (0.011 μg/mL), 3T0258 (0.06 μg/mL), 1T0655 (0.08 μg/mL), 4T0570 (0.09 μg/mL), 4m0368 (0.13 μg/mL), 3T0265 (0.44 μg/mL), 4T0578 (0.45 μg/mL), 3T0123 (0.52 μg/mL), 3T0202 (0.53 μg/mL), 3T0673 (0.53 μg/mL), 3T0245 (0.63 μg/mL), 5T0278 (0.63 μg/mL), 5T0465 (0.66 μg/mL), 3T0650 (0.74 μg/mL), 3T0478 (0.78 μg/mL), 3T0611 (0.78 μg/mL), 4T0452 (0.88 μg/mL), 4T0764 (0.88 μg/mL), 5T0451 (1.05 μg/mL), 3T0338 (1.06 μg/mL), 4T0444 (1.2 μg/mL), 3T0253 (1.31 μg/m L), 3T0553 (1.31 μg/mL), 1T0455 (1.77 μg/mL), 5T0209 (1.77 μg/mL), 1T0227 (1.86 μg/mL), 4T0784 (1.86 μg/mL), 5T0223 (1.86 μg/mL), 3T0468 (2.1 μg/mL), 5T0337 (2.21 μg/mL), 1T0451 (2.5 μg/mL), 5T0202 (2.5 μg/mL), 4T0726 (2.56 μg/mL), 1T0201 (2.63 μg/mL), 1T0325 (2.63 μg/mL), 1T0473 (2.63 μg/mL), 1T0139 (7.44 μg/mL), 5T0180 (12,5 μg/mL), 5T0376 (12.5 μg/mL), 1T0248 (14.8 μg/mL), 4T0429 (35 μg/mL), 4T0306 (100 μg/mL).

As a reference value, it may be mentioned that the antibody mAb114, which is presently administered to Ebola patients, exhibits neutralization at a concentration of 0.744 μg/mL (FIG. 4*d*).

According to a preferred embodiment of the present invention, the monoclonal human antibody or binding fragment thereof is or may be derived from one antibody from the group comprising 1T0325, 1T0451, 1T0473, 1T0655, 3T0123, 3T0253, 3T0553, 4T0243, 4T0306, 4T0570, 4T0726, 4T0764, 4T0784, 5T0180, 5T0223, 5T0278, 5T0337, 5T0451. More preferably the monoclonal human antibody or binding fragment thereof is or may be derived from the antibody 4T0243 or 3T0331, even more preferably from the antibody 3T0331.

In the description of the present application, antibody designations may be used. It is pointed out that the antibodies consist of heavy and light chains which also form part of the present description. If reference is made to an antibody by its designation or to a SEQ ID No., it should be understood that these ways of reference are interchangeable.

In this regard, the following antibodies under their designation are herewith disclosed to be made up of the following heavy and light chains:

1T0129 (consisting of the heavy chain amino acid sequence of SEQ ID No. 1 and the light chain amino acid sequence of SEQ ID No. 2), 1T0139 (heavy chain SEQ ID No. 3 and the light chain SEQ ID No. 4), 1T0201 (heavy chain SEQ ID No. 5 and the light chain SEQ ID No. 6), 1T0221 (heavy chain SEQ ID No. 7 and the light chain SEQ ID No. 8), 1T0225 (heavy chain SEQ ID No. 9 and the light chain SEQ ID No. 10), 1T0227 (heavy chain SEQ ID No. 11 and the light chain SEQ ID No. 12), 1T0248 (heavy chain SEQ ID No. 13 and the light chain SEQ ID No. 14), 1T0321 (heavy chain SEQ ID No. 15 and the light chain SEQ ID No. 16), 1T0325 (heavy chain SEQ ID No. 17 and the light chain SEQ ID No. 18), 1T0371 (heavy chain SEQ ID No. 19 and the light chain SEQ ID No. 20), 1T0451 (heavy chain SEQ ID No. 21 and the light chain SEQ ID No. 22), 1T0455 (heavy chain SEQ ID No. 23 and the light chain SEQ ID No. 24), 1T0465 (heavy chain SEQ ID No. 25 and the light chain SEQ ID No. 26), 1T0473 (heavy chain SEQ ID No. 27 and the light chain SEQ ID No. 28), 1T0552 (heavy chain SEQ ID No. 29 and the light chain SEQ ID No. 30), 1T0655 (heavy chain SEQ ID No. 31 and the light chain SEQ ID No. 32), 3T0123 (heavy chain SEQ ID No. 33 and the light chain SEQ ID No. 34), 3T0202 (heavy chain SEQ ID No. 35 and the light chain SEQ ID No. 36), 3T0215 (heavy chain SEQ ID No. 37 and the light chain SEQ ID No. 38), 3T0245 (heavy chain SEQ ID No. 39 and the light chain SEQ ID No. 40), 3T0253 (heavy chain SEQ ID No. 41 and the light chain SEQ ID No. 42), 3T0258 (heavy chain SEQ ID No. 43 and the light chain SEQ ID No. 44), 3T0265 (heavy chain SEQ ID No. 45 and the light chain SEQ ID No. 46), 3T0331 (heavy chain SEQ ID No. 47 and the light chain SEQ ID No. 48), 3T0338 (heavy chain SEQ ID No. 49 and the light chain SEQ ID No. 50), 3T0350 (heavy chain SEQ ID No. 51 and the light chain SEQ ID No. 52), 3T0405 (heavy chain SEQ ID No. 53 and the light chain SEQ ID No. 54), 3T0415 (heavy chain SEQ ID No. 55 and the light chain SEQ ID No. 56), 3T0468 (heavy chain SEQ ID No. 57 and the light chain SEQ ID No. 58), 3T0478 (heavy chain SEQ ID No. 59 and the light chain SEQ ID No. 60), 3T0553 (heavy chain SEQ ID No. 61 and the light chain SEQ ID No. 62), 3T0611 (heavy chain SEQ ID No. 63 and the light chain SEQ ID No. 64),
3T0650 (heavy chain SEQ ID No. 65 and the light chain SEQ ID No. 66),
3T0673 (heavy chain SEQ ID No. 67 and the light chain SEQ ID No. 68),
4m0333 (heavy chain SEQ ID No. 69 and the light chain SEQ ID No. 70),
4m0368 (heavy chain SEQ ID No. 71 and the light chain SEQ ID No. 72),
4m0373 (heavy chain SEQ ID No. 73 and the light chain SEQ ID No. 74),
4T0115 (heavy chain SEQ ID No. 75 and the light chain SEQ ID No. 76),
4T0154 (heavy chain SEQ ID No. 77 and the light chain SEQ ID No. 78),
4T0159 (heavy chain SEQ ID No. 79 and the light chain SEQ ID No. 80),
4T0176 (heavy chain SEQ ID No. 81 and the light chain SEQ ID No. 82),
4T0182 (heavy chain SEQ ID No. 83 and the light chain SEQ ID No. 84),
4T0243 (heavy chain SEQ ID No. 85 and the light chain SEQ ID No. 86),
4T0262 (heavy chain SEQ ID No. 87 and the light chain SEQ ID No. 88),
4T0284 (heavy chain SEQ ID No. 89 and the light chain SEQ ID No. 90),
4T0306 (heavy chain SEQ ID No. 91 and the light chain SEQ ID No. 92),
4T0344 (heavy chain SEQ ID No. 93 and the light chain SEQ ID No. 94),
4T0365 (heavy chain SEQ ID No. 95 and the light chain SEQ ID No. 96),
4T0412 (heavy chain SEQ ID No. 97 and the light chain SEQ ID No. 98),
4T0423 (heavy chain SEQ ID No. 99 and the light chain SEQ ID No. 100),
4T0427 (heavy chain SEQ ID No. 101 and the light chain SEQ ID No. 102),
4T0429 (heavy chain SEQ ID No. 103 and the light chain SEQ ID No. 104),
4T0434 (heavy chain SEQ ID No. 105 and the light chain SEQ ID No. 106),
4T0444 (heavy chain SEQ ID No. 107 and the light chain SEQ ID No. 108),
4T0452 (heavy chain SEQ ID No. 109 and the light chain SEQ ID No. 110),
4T0525 (heavy chain SEQ ID No. 111 and the light chain SEQ ID No. 112),
4T0541 (heavy chain SEQ ID No. 113 and the light chain SEQ ID No. 114),
4T0570 (heavy chain SEQ ID No. 115 and the light chain SEQ ID No. 116),
4T0578 (heavy chain SEQ ID No. 117 and the light chain SEQ ID No. 118),
4T0657 (heavy chain SEQ ID No. 119 and the light chain SEQ ID No. 120),
4T0726 (heavy chain SEQ ID No. 121 and the light chain SEQ ID No. 122),
4T0764 (heavy chain SEQ ID No. 123 and the light chain SEQ ID No. 124),
4T0784 (heavy chain SEQ ID No. 125 and the light chain SEQ ID No. 126),
5T0107 (heavy chain SEQ ID No. 127 and the light chain SEQ ID No. 128),
5T0180 (heavy chain SEQ ID No. 129 and the light chain SEQ ID No. 130),
5T0202 (heavy chain SEQ ID No. 131 and the light chain SEQ ID No. 132),
5T0209 (heavy chain SEQ ID No. 133 and the light chain SEQ ID No. 134),
5T0223 (heavy chain SEQ ID No. 135 and the light chain SEQ ID No. 136),
5T0257 (heavy chain SEQ ID No. 137 and the light chain SEQ ID No. 138),
5T0278 (heavy chain SEQ ID No. 139 and the light chain SEQ ID No. 140),
5T0337 (heavy chain SEQ ID No. 141 and the light chain SEQ ID No. 142),
5T0376 (heavy chain SEQ ID No. 143 and the light chain SEQ ID No. 144),
5T0378 (heavy chain SEQ ID No. 145 and the light chain SEQ ID No. 146),
5T0404 (heavy chain SEQ ID No. 147 and the light chain SEQ ID No. 148),
5T0406 (heavy chain SEQ ID No. 149 and the light chain SEQ ID No. 150),
5T0420 (heavy chain SEQ ID No. 151 and the light chain SEQ ID No. 152),
5T0451 (heavy chain SEQ ID No. 153 and the light chain SEQ ID No. 154),
5T0465 (heavy chain SEQ ID No. 155 and the light chain SEQ ID No. 156)

The present invention further relates to a pharmaceutical composition comprising a monoclonal human antibody or binding fragment thereof according to the invention as defined and further described herein and at least one pharmaceutically acceptable excipient. Preferably, the pharmaceutical composition is a vaccination composition for a human subject.

The present invention also encompasses a kit comprising a monoclonal human antibody or binding fragment thereof according to the invention as defined and further described herein and a container.

In one aspect, the present invention is also directed to the monoclonal human antibody or binding fragment thereof according to the invention as defined and further described herein, the pharmaceutical composition as described herein and the kit for use as a medicament, preferably for use as a vaccine.

In another aspect, the present invention is also directed to the monoclonal human antibody or binding fragment thereof according to the invention as defined and further described wherein, the pharmaceutical composition as described herein and the kit for use in the treatment or prevention of a disease caused by the infectious pathogen in a human subject, preferably for use in the treatment or prevention of *Ebolavirus*-caused disease in human subjects.

In one other aspect, the present invention is also directed to a method of treatment of a patient suffering from a disease caused by an infectious pathogen, preferably *Ebolavirus*-caused disease, wherein the patient is administered an effective amount of the monoclonal human antibody or binding fragment thereof according to the invention or a pharmaceutical composition of the invention.

In another aspect, the present invention is also directed to the use of the monoclonal human antibody or binding fragment thereof according to the invention or a pharmaceutical composition of the invention in the manufacture of a medicament for treatment of a disease caused by an infectious pathogen, preferably *Ebolavirus*-caused disease.

All embodiments of the present invention as described herein are deemed to be combinable in any combination, unless the skilled person considers such a combination to not make any technical sense.

EXAMPLES rVSV-ZEBOV-GP-Vaccinated Individuals and Sample Collection

Individuals participating in this study were previously enrolled in the Phase I Trial to Assess the Safety, Tolerability and Immunogenicity of an Ebola Virus Vaccine (rVSV4G-ZEBOV-GP, NCT02283099) and were vaccinated with either $3\times10^5$ or $3\times10^6$ plaque forming units (pfu).

From this cohort, four individuals were enrolled in an observational study (INA; 16-054) at the University Hospital of Cologne to collect PBMC and serum samples. The protocol was approved by the Institutional Review Board (IRB) of the University of Cologne, Germany. From all participants, serum or plasma samples, and EDTA blood or leukapheresis samples were collected and peripheral blood mononuclear cells (PBMC) were purified from EDTA blood or leukapheresis by density gradient centrifugation using HistoPaque and stored in FBS containing 10% DMSO at −150° C. Serum and plasma samples were stored at −80° C.

All enrolled subjects provided written informed consent before participation in the study and all aspects of study conduct were in accordance with Good Clinical Practice. Sera of Ebola virus survivors were collected in the context of the project EVIDENT (Ebola Virus Disease: Correlates of Protection, Determinants of Outcome, and Clinical Management) after obtaining informed consent and provided to use as control samples for anti-EBOV IgG titer and neutralizing activity.

Expression and Purification of *Ebolavirus* GPs

Recombinant *Ebolavirus* GP constructs lacking the TM domain (Δ651-676, EBOV Makona (GenBank: KJ660347, EBOV Mayinga (GenBank: AF086833.2, BDBV (GenBank: FJ217161, SUDV Gulu (GenBank: AY729654.1) or TM and MLD domain [Δ313-464, EBOV Makona (GenBank: KJ660347)] as well as sGP (GenBank: KJ660347) were cloned into the pCAGGS backbone (Mittler, Schudt et al. 2018).

GP constructs were further modified to carry an Avi-tag as well as a His-tag for purification, and, except sGP, a GCN4 domain for GP complex formation at the C-terminal end (Corti, Misasi et al. 2016). HEK293F cells were maintained in FreeStyle Medium at 37° C. with 6% $CO_2$, shaking at 110 rpm. At a concentration of $0.8\times10^6$ cells/ml transfection was performed using 25 kDa polyethylenimine (PEI) with 1 μg DNA/ml cell suspension.

After incubating for 7 days, supernatant was harvested, filtered (0.45 μm filter) and incubated with Protino Ni-NTA (nitrilotriacetic acid) agarose beads overnight. Beads were pelleted, transferred into a column and washed 1× with NPI-10 ($H_2O$, 50 mM $NaH_2PO_4$, 300 mM NaCl, 10 mM imidazole, pH=8) and 1× with NPI-20 (H2O, 50 mM $NaH_2PO_4$, 300 mM NaCl, 20 mM imidazole, pH=8) buffer. His-tagged glycoproteins were eluted by addition of NPI-100 (H2O, 50 mM $NaH_2PO_4$, 300 mM NaCl, 100 mM imidazole, pH=8) and buffer was exchanged to PBS using centrifugal filter units. All glycoproteins were sterile-filtered and stored at −80° C.

Single Cell Sort of EBOV GPΔTM-Specific $IgG^+$ B Cells

Peripheral blood mononuclear cells (PBMCs) were enriched for B lymphocytes by magnetic cell separation (MACS) with CD19-microbeads according to manufacturer's instruction. MACS LS separation columns (Miltenyi Biotec) were used to enrich labeled cells. B cells were spun and suspended in PBS with 2% FBS and 2 mM EDTA and subjected to fluorescence staining with DAPI, anti-huCD20-Alexa Fluor 700 (BD), anti-hulgG-APC, and EBOV GPΔTM-DyLight 488 (SEQ ID No. 158; Microscale Antibody Kit).

Cells were stained for 20 min at 4° C. and live CD20+ IgG+ EBOV GP+ cells were sorted using a FACSAriaIII according to the manufacturer's instructions in a single cell manner into 96-well plates. All wells contained 4 μl lysis buffer (0.5×PBS, 0.5 U/μl RNAsin, 0.5 U/μl RNaseOUT, and 10 mM DTT. After sorting, plates were immediately stored at −80° C. until further processing.

Ig Heavy/Light Chain Amplification

Procedure for PCR amplification was performed as previously described (Tiller, Meffre et al. 2008, von Boehmer, Liu et al. 2016) but with various adjustments. Briefly, Random Hexamers, NP-40, and RNAseOUT were added to sorted cells in lysis buffer. The reaction was incubated for 1 min at 65° C. and cooled down for at least 2 min on ice. Afterwards, 1× Superscript IV RT buffer, 50 U/rxn SuperScript IV Reverse Transcriptase, dNTPs, DTT, RNAseOUT and RNasin were added and incubated 15 min at RT, 10 min at 50° C. and 10 min at 80° C.

cDNA was used to amplify light and heavy chains using PlatinumTaq HotStart polymerase according to manufacturer's protocol with 6% KB extender and 4 μl cDNA template. Amplification was achieved by sequential semi-nested PCRs using optimized and newly developed primer sets (Kreer, Döring et al., manuscript submitted). The results of the PCRs were analyzed by gel electrophoresis and products of correct sizes were subjected to Sanger sequencing.

Sequence Analysis

Sequencing chromatograms were filtered for a mean Phred score of 28 and a minimal length of 240 nt. Remaining sequences were annotated with IgBLAST (Ye, Ma et al. 2013) and trimmed to extract only the variable region from FWR1 to the end of the J gene. Base calls within the variable region with a Phred score below 16 were masked and sequences with more than 15 masked nucleotides, stop codons, or frameshifts were excluded from further analyses.

In order to identify clonally related sequences within a single subject, we grouped all productive heavy chain sequences of that particular subject by identical $V_H$ genes, determined the pairwise Levenshtein distance for their CDRH3s, and assigned an individual clone-number to sequence groups that share the same $V_H$ gene and have a minimal CDRH3 identity of 75% (with respect to the shortest CDRH3).

100 rounds of input sequence randomization and clonal assignment were performed and the result with the lowest number of remaining unassigned (non-clonal) sequences was selected for downstream analyses. All clones were cross-validated by the investigators taking also into account shared mutations.

Cloning and Production of EBOV GP-Specific mAbs

Selected antibody sequences were cloned into mAb expression vectors by sequence- and ligation-independent cloning (SLIC) as previously described (von Boehmer, Liu et al. 2016). Briefly, amplicons for cloning were produced by PCR-amplification using Q5 High Fidelity polymerase (NEB) by standard PCR protocols and previously described primers (Tiller, Meffre et al. 2008). PCR products were purified (GeneJET Gel Extraction and DNA Cleanup Micro Kit, Macherey Nagel), cloned into expression vectors by SLIC reaction using T4 DNA polymerase (NEB) and transduced into *E. coli* DH5α. 4-8 colonies were evaluated by PCR and gel electrophoresis, and forwarded to Sanger sequencing. Plasmids with correct antibody sequences were amplified by midi preparation according to manufacturer's protocol and stored at 4° C. (short term) or −20° C.

Heavy and light chain-encoding plasmids were co-transfected into HEK293E cells with PEI reagent as described above. Cultures were harvested after 7 days, cell-free supernatants were filtered, and incubated with Protein G sepharose at 4° overnight. Beads were transferred to columns, washed 3× with PBS and antibodies were eluted with 0.1 M Glycine (pH=3). Subsequently, pH of eluate was neutralized with 1 M Tris-HCl (pH=8). Buffer was exchanged to PBS as described above.

ELISA Analysis to Determine Antibody Binding Activity to GPs

ELISAs were conducted in high binding 96-well ELISA plates. Plates were coated with 2.5 μg/ml GPs at 4° C. overnight, washed 3× with PBST (PBS, 0.05% Tween-20) and blocked with PBST/2% BSA for 60 min at RT. mAbs were tested at 4- or 6-fold dilutions (1:3 or 1:5) with starting concentrations of 10 μg/ml. After incubation for 90 min at RT, plates were washed 3× and incubated with horseradish peroxidase-conjugated goat anti-human IgG antibody (1:2500 in PBST/2% BSA) for 60 min at RT.

Reaction was started with 2,2'-azino-bis(3-ethylResults-benzothiazoline-6-sulphonic acid) solution (ABTS) and absorbance (OD 415 nm-695 nm) was measured with absorbance reader after fixed incubation times. For analysis, time points with overlapping standards curves were selected and ODs as well as $EC_{50}$ were determined. Antibodies were considered GP-reactive, if OD was above 0.2 at a 10 μg/ml mAb concentration and $EC_{50}$ did not exceed 15 μg/ml.

For assessment of EBOV GP-specificity of antibodies, EBOV GPΔTM was used to coat ELISA plates. To evaluate cross-reactivity, also GPs of Filoviruses BDBV, SUDV and MARV were tested.

Neutralization Assays

Antibodies (starting at a concentration of 100 μg/ml) were serially diluted in 96-well culture plates in Dulbecco's Modified Eagle's Medium supplemented with 2% fetal calf serum, penicillin (50 units/ml), streptomycin (50 μg/ml) and L-glutamine (2 mM). 100 $TCID_{50}$ units of EBOV Mayinga (GenBank: NC_002549) and SUDV Boniface (GenBank: FJ968794.1) were added to the serum or antibody dilutions. Following incubation at 37° C. for 1 hour, Vero C1008 cells (ATCC® CRL-1586™; 10,000 cells per well) were added. Plates were then incubated at 37° C., 5% $CO_2$ and cytopathic effects (CPE) evaluated at day 7 post infection.

Neutralization was defined as clear reduction of CPE in serum or antibody dilutions compared to positive controls. Neutralization titers were calculated of four replicates as geometric mean titers (GMT; reciprocal value) or geometric mean concentrations in the case of monoclonal antibodies (GMC). The cut-off of the assay is determined by the first dilution of the respective serum or antibody. Neutralization assays were performed in the BSL-4 laboratory of the Institute of Virology, Philipps-University Marburg, Germany.

REFERENCES

Bornholdt, Z. A., et al. (2016). "Isolation of potent neutralizing antibodies from a survivor of the 2014 Ebola virus outbreak." *Science* 351(6277): 1078-1083.

Corti, D., et al. (2016). "Protective monotherapy against lethal Ebola virus infection by a potently neutralizing antibody." *Science* 351(6279): 1339-1342.

Gaebler, C., et al. (2013). "Isolation of HIV-1-reactive antibodies using cell surface-expressed gp160Deltac (BaL.)." *J Immunol Methods* 397(1-2): 47-54.

Maruyama, T., et al. (1999). "Ebola Virus can be effectively neutralized by antibody produced in natural human infection." *J Virol.*

Mittler, E., et al. (2018). "A Fluorescently Labeled Marburg Virus Glycoprotein as a New Tool to Study Viral Transport and Assembly." *J Infect Dis* 218(suppl_5): S318-S326.

Tiller, T., et al. (2008). "Efficient generation of monoclonal antibodies from single human B cells by single cell RT-PCR and expression vector cloning." *Journal of Immunological Methods* 329(1-2): 112-124.

von Boehmer, L., et al. (2016). "Sequencing and cloning of antigen-specific antibodies from mouse memory B cells." *Nat Protoc* 11(10): 1908-1923.

Ye, J., et al. (2013). "IgBLAST: an immunoglobulin variable domain sequence analysis tool." *Nucleic Acids Res* 41(Web Server issue): W34-40.

The invention claimed is:

1. A monoclonal human antibody or binding fragment directed against an infectious pathogen, wherein the infectious pathogen is a virus from the genus *Ebolavirus*, wherein the antibody or binding fragment thereof comprises the heavy chain amino acid sequence of CDR1 to CDR3 of SEQ ID NO: 47 and the light chain amino acid sequence of CDR1 to CDR3 of SEQ ID NO: 48.

2. The monoclonal human antibody or binding fragment of claim 1, wherein the monoclonal human antibody or binding fragment thereof is monoclonal antibody 3T0331.

3. A monoclonal human antibody or binding fragment directed against an infectious pathogen, wherein the infectious pathogen is a virus from the genus *Ebolavirus*, wherein the antibody or binding fragment thereof comprises the heavy chain amino acid sequence of CDR1 to CDR3 of SEQ ID NO: 85 and the light chain amino acid sequence of CDR1 to CDR3 of SEQ ID NO: 86.

4. The monoclonal human antibody or binding fragment of claim 3, wherein the monoclonal human antibody or binding fragment thereof is monoclonal antibody 4T0243.

5. A pharmaceutical composition comprising a monoclonal human antibody or binding fragment thereof according to claim 1 and at least one pharmaceutically acceptable excipient, wherein the pharmaceutical composition is a vaccination composition for a human subject.

6. A pharmaceutical composition comprising a monoclonal human antibody or binding fragment thereof according to claim 3 and at least one pharmaceutically acceptable excipient, wherein the pharmaceutical composition is a vaccination composition for a human subject.

7. A monoclonal human antibody or binding fragment directed against an infectious pathogen, wherein the infectious pathogen is a virus from the genus *Ebolavirus*, wherein the antibody or binding fragment thereof comprises the heavy chain amino acid sequence of SEQ ID NO: 47 and the light chain amino acid sequence of SEQ ID NO: 48.

8. The monoclonal human antibody or binding fragment of claim 7, wherein the monoclonal human antibody or binding fragment thereof is monoclonal antibody 3T0331.

9. A monoclonal human antibody or binding fragment directed against an infectious pathogen, wherein the infectious pathogen is a virus from the genus *Ebolavirus*, wherein the antibody or binding fragment thereof comprises the heavy chain amino acid sequence of SEQ ID NO: 85 and the light chain amino acid sequence of SEQ ID NO: 86.

10. The monoclonal human antibody or binding fragment of claim 9, wherein the monoclonal human antibody or binding fragment thereof is monoclonal antibody 4T0243.

11. A pharmaceutical composition comprising a monoclonal human antibody or binding fragment thereof according to claim 7 and at least one pharmaceutically acceptable excipient, wherein the pharmaceutical composition is a vaccination composition for a human subject.

12. A pharmaceutical composition comprising a monoclonal human antibody or binding fragment thereof according to claim 9 and at least one pharmaceutically acceptable excipient, wherein the pharmaceutical composition is a vaccination composition for a human subject.

* * * * *